United States Patent
Hockerman et al.

(12) 
(10) Patent No.: US 6,583,299 B1
(45) Date of Patent: Jun. 24, 2003

(54) α-AMINO-β-SULFONYL HYDROXAMIC ACID COMPOUNDS

(75) Inventors: Susan L Hockerman, Chicago, IL (US); Daniel P. Becker, Glenview, IL (US); Louis J Bedell, Mt. Prospect, IL (US); Gary A DeCrescenzo, St. Charles, MO (US); John N Freskos, Clayton, MO (US); Daniel P Getman, Chesterfield, MO (US); Robert M Heintz, Ballwin, MO (US); Madeleine H Li, Vernon Hills, MO (US); Brent V Mischke, Defiance, MO (US); Clara I Villamil, Glenview, IL (US); Thomas E Barta, Evanston, IL (US)

(73) Assignee: G.D. Searle & Co., Skokie, IL (US)

( * ) Notice: Subject to any disclaimer, the term of this patent is extended or adjusted under 35 U.S.C. 154(b) by 0 days.

(21) Appl. No.: 09/572,019

(22) Filed: May 16, 2000

Related U.S. Application Data

(60) Provisional application No. 60/134,996, filed on May 20, 1999.

(51) Int. Cl.⁷ .................... C07D 315/00; C07C 239/00; C07C 259/04
(52) U.S. Cl. ................ 549/419; 560/312; 562/800
(58) Field of Search .............. 564/306; 549/419; 560/312; 562/800

(56) References Cited

U.S. PATENT DOCUMENTS

| | | | |
|---|---|---|---|
| 4,595,700 A | | 6/1986 | Donald et al. |
| 5,516,936 A | * | 5/1996 | Phillips et al. |

FOREIGN PATENT DOCUMENTS

| | | | |
|---|---|---|---|
| EP | 0 780 386 A1 | 6/1997 | |
| JP | 62221675 | * 1/1998 | |
| WO | WO 9218003 | * 10/1992 | |
| WO | WO 93/20047 | 10/1993 | |
| WO | WO 94/02466 | 2/1994 | |
| WO | WO 94/24140 | 10/1994 | |
| WO | WO 95/09841 | 4/1995 | |
| WO | WO 95/12389 | 5/1995 | |
| WO | WO 96/06074 | 2/1996 | |
| WO | WO 96/11209 | 4/1996 | |
| WO | WO 97/20824 | 6/1997 | ......... C07D/241/04 |
| WO | WO 97/24117 | 7/1997 | |
| WO | WO 9749679 | * 12/1997 | |
| WO | WO 9803164 | * 1/1998 | |
| WO | WO 9902146 | * 1/1999 | |

OTHER PUBLICATIONS

Lappin et. al., "Metabolism of 2, 3, 5, 6–tetrachloronitrobenzene (tecnazene) in a rat", Xenobiotica, vol. 26(1), pp. 65–77, 1996.*

Mayring et. al., "Reference metabolites of sulfur–containing derivitives of the fungicides pentachloronitrobenzene and hexachlorobenzene. II. Synthesis and analytical data", Chemosphere (1986), 15(2), pp. 105–113, 1986.*

CA 65:2179b, "Cinnamanilides", vol. 65, Column 2179b, 1966.*

CA 58:4460g, "Potential anticancer agents –(LXXIX) aromatic N mustards derived from cysteine", vol. 53, 1963.*

CA 53:14959h, "Heterogeneous Polymerization of alpha–N–carboxyamino acid anhydrides", vol. 53, col. 14959 h, 1959.*

CA52:1927b, "Synthesis with Tertiary Mannic bases—(XII) condensations with dimethylaminomethylocetaminomalonic ester methiodides–condensation reactions of quaternary ammonium salts", col. 1927b, vol. 52, 1996.*

Mitchell et al., Cloning, Expression, and Type II Collagenolytic Activity of Matrix Metalloproteinase–13 from Human Osteoarthritic Cartilage, J. Clin. Invest., vol. 97, No. 3, Feb. 1996, 761–768.

Reboul et al., The New Collagenase, Collagenase–3, Is Expressed and Synthesized by Human Chondrocytes but not by Synoviocytes, J. Clin. Invest., vol. 97, No. 9, May 1996, 2011–2019.

Gearing et al., Processing of tumour necrosis factor–∂ precursor by metalloproteinases, Nature, vol. 370, Aug. 18, 1994; 555–557.

McGeehan, et al., Regulation of tumour necrosis factor–∂ precursor by metalloproteinases inhibitor, Nature, vol. 370, Aug. 18, 1994; 558–561.

Schwartz and Van Wart, 8 Synthetic Inhibitors of Bacterial and Mammalian Interstitial Collagenases, Progress in Medicinal Chemistry—vol. 29, 271–334 (1992).

Rasmussen and McCann, Matrix Metalloproteinase Inhibition as a Novel Anticancer Strategy: A Review with Special Focus on Batimastar and Marimastar, Pharmacol. Th. vol. 75, No. 1, pp. 69–75, 1997.

Denis and Verweij, Matrix metalloproteinase inhibitors: Present achievements and future prospects, Investigational New Drugs 15: 175–185, 1997.

* cited by examiner

*Primary Examiner*—Alan L. Rotman
(74) *Attorney, Agent, or Firm*—David M. Gryte, Esq.; Harness, Dickey & Pierce, P.L.C.

(57) ABSTRACT

A family of molecules is disclosed that inhibit matrix metalloprotease (MMP) activity, and particularly inhibit the activity of one or more of MMP-2, MMP-9, or MMP-13, while generally exhibiting little activity against MMP-1. A contemplated compound also exhibits little inhibition of the production of TNF. A contemplated compound is an α-amino-β-sulfonyl carbocyclo, heterocyclo, aryl, or heteroaryl hydroxamic acid. Also disclosed are processes for preparing a contemplated compound and for treating a mammal having a condition associated with pathological matrix metalloprotease activity.

76 Claims, No Drawings

α-AMINO-β-SULFONYL HYDROXAMIC ACID COMPOUNDS

CROSS-REFERENCE TO RELATED PATENT APPLICATIONS

This patent claims priority to U.S. Provisional Patent Application No. 60/134,996 (filed May 20, 1999). The entire text of U.S. Provisional Patent Application No. 60/134,996 is hereby incorporated by reference into this patent.

TECHNICAL FIELD

This invention is directed to proteinase (protease) inhibitors, and more particularly to α-amino-β-sulfonyl carbocyclo, heterocyclo, aryl, or heteroaryl hydroxamic acid compounds that, inter alia, inhibit the activity of matrix metalloproteinases, compositions of those inhibitors, intermediates for the syntheses of those compounds, processes for the preparation of the compounds and processes for treating pathological conditions associated with pathological matrix metalloproteinase activity.

BACKGROUND OF THE INVENTION

Connective tissue, extracellular matrix constituents and basement membranes are required components of all mammals. These components are the biological materials that provide rigidity, differentiation, attachments and, in some cases, elasticity to biological systems including human beings and other mammals. Connective tissues components include, for example, collagen, elastin, proteoglycans, fibronectin and laminin. These biochemicals makeup, or are components of structures, such as skin, bone, teeth, tendon, cartilage, basement membrane, blood vessels, cornea and vitreous humor.

Under normal conditions, connective tissue Turnover and/or repair processes are controlled and in equilibrium. The loss of this balance for whatever reason leads to a number of disease states. Inhibition of the enzymes responsible loss of equilibrium provides a control mechanism for this tissue decomposition and, therefore, a treatment for these diseases.

Degradation of connective tissue or connective tissue components is carried out by the action of proteinase enzymes released from resident tissue cells and/or invading inflammatory or tumor cells. A major class of enzymes involved in this function is the zinc metalloproteinases (metalloproteases, or MMPs).

The metalloprotease enzymes are divided into classes with some members having several different names in common use. Examples are: collagenase I (MMP-1, fibroblast collagenase; EC 3.4.24.3); collagenase II (MMP-8, neutrophil collagenase; EC 3.4.24.34), collagenase III (MMP-13), stromelysin 1 (MMP-3; EC 3.4.24.17), stromelysin 2 (MMP-10; EC 3.4.24.22), proteoglycanase, matrilysin (MMP-7), gelatinase A (MMP-2, 72 kDa gelatinase, basement membrane collagenase; EC 3.4.24.24), gelatinase B (MMP-9, 92 kDa gelatinase; EC 3.4.24.35), stromelysin 3 (MMP-11), metalloelastase (MMP-12, HME, human macrophage elastase) and membrane MMP (MMP-14). MMP is an abbreviation or acronym representing the term Matrix Metalloprotease with the attached numerals providing differentiation between specific members of the MMP group.

The uncontrolled breakdown of connective tissue by metalloproteases is a feature of many pathological conditions. Examples include rheumatoid arthritis, osteoarthritis, septic arthritis; corneal, epidermal or gastric ulceration; tumor metastasis, invasion or angiogenesis; periodontal disease; proteinuria; Alzheimer's Disease; coronary thrombosis and bone disease. Defective injury repair processes can also occur. This can produce improper wound healing leading to weak repairs, adhesions and scarring. These latter defects can lead to disfigurement and/or permanent disabilities as with post-surgical adhesions.

Matrix metalloproteases are also involved in the biosynthesis of tumor necrosis factor (TNF) and inhibition of the production or action of TNF and related compounds is an important clinical disease treatment mechanism. TNF-α, for example, is a cytokine that at present is thought to be produced initially as a 28 kD cell-associated molecule. It is released as an active, 17 kD form that can mediate a large number of deleterious effects in vitro and in vivo. For example, TNF can cause and/or contribute to the effects of inflammation, rheumatoid arthritis, autoimmune disease, multiple sclerosis, graft rejection, fibrotic disease, cancer, infectious diseases, malaria, mycobacterial infection, meningitis, fever, psoriasis, cardiovascular/pulmonary effects such as post-ischemic reperfusion injury, congestive heart failure, hemorrhage, coagulation, hyperoxic alveolar injury, radiation damage and acute phase responses like those seen with infections and sepsis and during shock such as septic shock and hemodynamic shock. Chronic release of active TNF can cause cachexia and anorexia. TNF can be lethal.

TNF-α convertase is a metalloproteinase involved in the formation of active TNF-α. Inhibition of TNF-α convertase inhibits production of active TNF-α. Compounds that inhibit both MMPs activity have been disclosed in WIPO International Publication Nos. WO 94/24140, WO 94/02466, WO 97/20824 and EP 0 780 386 A1. There remains a need for effective MMP and TNF-α convertase inhibiting agents. Compounds that inhibit MMPs such as collagenase, stromelysin and gelatinase have been shown to inhibit the release of TNF (Gearing et al. Nature 376, 555–557 (1994), McGeehan et al., Nature 376, 558–561 (1994)).

MMPs are involved in other biochemical processes in mammals as well. Included is the control of ovulation, post-partum uterine involution, possibly implantation, cleavage of APP (β-Amyloid Precursor Protein) to the amyloid plaque and inactivation of $\alpha_1$-protease inhibitor ($\alpha_1$-PI). Inhibition of these metalloproteases permits the control of fertility and the treatment or prevention of Alzheimers Disease. In addition, increasing and maintaining the levels of an endogenous or administered serine protease inhibitor drug or biochemical such as $\alpha_1$-PI supports the treatment and prevention of diseases such as emphysema, pulmonary diseases, inflammatory diseases and diseases of aging such as loss of skin or organ stretch and resiliency.

Inhibition of selected MMPs can also be desirable in other instances. Treatment of cancer and/or inhibition of metastasis and/or inhibition of angiogenesis are examples of approaches to the treatment of diseases wherein the selective inhibition of stromelysin (MMP-3), gelatinase (MMP-2), gelatinase B (MMP-9) or collagenase III (MMP-13) are the relatively most important enzyme or enzymes to inhibit especially when compared with collagenase I (MMP-1). A drug that does not inhibit collagenase I can have a superior therapeutic profile.

Osteoarthritis, another prevalent disease wherein it is believed that cartilage degradation in inflamed joints is at least partially caused by MMP-13 released from cells such as stimulated chrondrocytes, may be best treated by administration of drugs one of whose modes of action is inhibition of MMP-13. See, for example, Mitchell et al., *J. Clin. Invest.*, 97:761–768 (1996) and Reboul et al., *J. Clin. Invest.*, 97:2011–2019 (1996).

Inhibitors of metalloproteases are known. Examples include natural biochemicals such as tissue inhibitor of metalloproteinase (TIMP), $\alpha_2$-macroglobulin and their analogs or derivatives. These are high molecular weight protein molecules that form inactive complexes with metalloproteases. A number of smaller peptide-like compounds that inhibit metalloproteases have been described. Mercaptoamide peptidyl derivatives have shown ACE inhibition in vitro and in vivo. Angiotensin converting enzyme (ACE) aids in the production of angiotensin II, a potent pressor substance in mammals and inhibition of this enzyme leads to the lowering of blood pressure.

Thiol group-containing amide or peptidyl amide-based metalloprotease (MMP) inhibitors are known as is shown in, for example, WO95/12389, WO96/11209 and U.S. Pat. No. 4,595,700. Hydroxamate group-containing MMP inhibitors are disclosed in a number of published patent applications such as WO 95/29892, WO 97/24117, WO 97/49679 and EP 0 780 386 that disclose carbon back-boned compounds, and WO 90/05719, WO 93/20047, WO 95/09841 and WO 96/06074 that disclose hydroxamates that have a peptidyl back-bones or peptidomimetic back-bones, as does the article by Schwartz et al., *Progr. Med. Chem.*, 29:271–334 (1992) and those of Rasmussen et al., *Pharmacol. Ther.*, 75(1): 69–75 (1997) and Denis et al., *Invest. New Drugs*, 15(3): 175–185 (1997).

One possible problem associated with known MMP inhibitors is that such compounds often exhibit the same or similar inhibitory effects against each of the MMP enzymes. For example, the peptidomimetic hydroxamate known as batimastat is reported to exhibit $IC_{50}$ values of about 1 to about 20 nanomolar (nM) against each of MMP-1, MMP-2, MMP-3, MMP-7, and MMP-9. Marimastat, another peptidomimetic hydroxamate was reported to be another broad-spectrum MMP inhibitor with an enzyme inhibitory spectrum very similar to batimastat, except that marimastat exhibited an $IC_{50}$ value against MMP-3 of 230 nM. Rasmussen et al., *Pharmacol. Ther.*, 75(1): 69–75 (1997).

Meta analysis of data from Phase I/II studies using marimastat in patients with advanced, rapidly progressive, treatment-refractory solid tumor cancers (colorectal, pancreatic, ovarian, prostate) indicated a dose-related reduction in the rise of cancer-specific antigens used as surrogate markers for biological activity. Although marimastat exhibited some measure of efficacy via these markers, toxic side effects were noted. The most common drug-related toxicity of marimastat in those clinical trials was musculoskeletal pain and stiffness, often commencing in the small joints in the hands, spreading to the arms and shoulder. A short dosing holiday of 1–3 weeks followed by dosage reduction permits treatment to continue. Rasmussen et al., *Pharmacol. Ther.*, 75(1): 69–75 (1997). It is thought that the lack of specificity of inhibitory effect among the MMPs may be the cause of that effect.

In view of the importance of hydroxamate MMP inhibitor compounds in the treatment of several diseases and the lack of enzyme specificity exhibited by two of the more potent drugs now in clinical trials, it would be a great benefit if hydroxamates of greater enzyme specificity could be found. This would be particularly the case if the hydroxamate inhibitors exhibited strong inhibitory activity against one or more of MMP-2, MMP-9 or MMP-13 that are associated with several pathological conditions, while at the same time exhibiting limited inhibition of MMP-1, an enzyme that is relatively ubiquitous and as yet not associated with any pathological condition. It would also be beneficial if a compound that inhibited one or more of the above MMPs, while sparing MMP-1, also did not inhibit production of TNF. The disclosure that follows describes one family of hydroxamate MMP inhibitors that exhibit those desirable activities.

BRIEF SUMMARY OF THE INVENTION

The present invention is directed to a family of molecules that among other properties inhibit matrix metalloprotease (MMP) activity, and particularly inhibit the activity of one or more of MMP-2, MMP-9, or MMP-13, while generally exhibiting little activity against MMP-1. A contemplated compound also exhibits little inhibition of the production of TNF. The present invention is also directed to processes for preparing a contemplated compound and for treating a mammal having a condition associated with pathological matrix metalloprotease activity.

Briefly, one embodiment of the present invention is directed to an α-amino-β-sulfonyl carbocyclo, heterocyclo, aryl, or heteroaryl hydroxamic acid compound that is active as a matrix metalloprotease enzyme inhibitor. That compound corresponds in structure to Formula A.

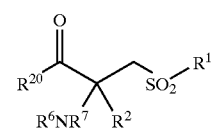

wherein $R^2$ is selected from the group consisting of a hydrido, $C_1$–$C_4$ hydrocarbyl, hydroxy-$C_1$–$C_4$ hydrocarbyl, $C_1$–$C_4$ hydrocarbyloxy, halo-$C_1$–$C_4$ hydrocarbyl, $C_1$–$C_4$ hydrocarbyloxymethyl, aryl, aryl $C_1$–$C_4$ hydrocarbyl, aminomethyl, (N—$C_1$–$C_3$ hydrocarbyl) aminomethyl, (N,N-di-$C_1$–$C_3$ hydrocarbyl) aminomethyl, (N-morpholino)methyl, (N-pyrrolidino) methyl, or (N-thiomorpholino)methyl group. $R^2$ is preferably a hydrido, hydroxy, hydroxymethyl, methoxymethyl or methyl-N-morpholinyl group.

$R^1$ is a substituent that contains an optionally substituted 5- or 6-membered carbocyclo, heterocyclo, aryl or heteroaryl radical bonded directly to the depicted $SO_2$— group that has a length of an extended pentyl group and less than about that of an extended eicosyl group, and preferably having a length that is longer than an extended hexyl group and less than that of an extended stearyl group. In addition, $R^1$ defines a three-dimensional volume upon rotation about an axis drawn through the $SO_2$-bonded 1-position and the 4-position of a 6-membered ring radical or drawn through the $SO_2$-bonded 1-position and the center of 3,4-bond of a 5-membered ring radical, whose widest dimension in a direction transverse to the axis of rotation is about that of one furanyl ring to about that of two phenyl rings.

$R^6$ and $R^7$ are independently selected from the group consisting of a hydrido, alkylcarbonyl, alkoxycarbonyl, arylcarbonyl, aralkylcarbonyl, carboxyalkyl, carboxyalkylcarbonyl, alkoxycarbonylaminoalkylcarbonyl, heterocyclocarbonyl, heterocycloalkylcarbonyl, aryloxycarbonylaminoalkylcarbonyl, aralkyloxycarbonylaminoalkylcarbonyl, perfluoroalkylcarbonyl, trifluoromethylalkylcarbonyl, alkylthioalkylcarbonyl, arylthioalkylcarbonyl, aralkylthioalkylcarbonyl, heteroaralkylthioalkylcarbonyl, or a sulfoxide or sulfone of any of said thio substituents, alkylsulfonyl, arylsulfonyl, and an aminocarbonylalkyl or aminocarbonylalkylcarbonyl group
  wherein the aminocarbonylalkyl or aminocarbonylalkylcarbonyl nitrogen is (i) unsubstituted, or (ii) is the reacted amine of an amino acid, or (iii) substituted with one or two radicals selected from the group consisting of an alkyl, hydroxyalkyl, hydroxyheteroaralkyl, cycloalkyl, aralkyl, trifluoromethylalkyl, heterocycloalkyl, benzofused heterocycloalkyl, benzofused heterocycloalkyl, benzofused cycloalkyl, and an N,N-dialkylsubstituted-alkylaminoalkyl group, or (iv) that carboxamido nitrogen and two substituents bonded thereto together form a 5- to 8-membered heterocyclo, heteroaryl or benzofused heterocycloalkyl ring that is itself unsubstituted or substituted with one or two radicals independently selected from the group consisting of an alkyl, alkoxycarbonyl, nitro, heterocycloalkyl, hydroxy, hydroxycarbonyl, aryl, aralkyl, heteroaralkyl and an amino group, or $R^6$ and $R^7$ together with the depicted nitrogen atom form a saturated or unsaturated cyclic imide substituent in which the ring contains five to eight atoms.

$R^{20}$ is (a) —O—$R^{21}$, where $R^{21}$ is selected from the group consisting of a hydrido, $C_1$–$C_6$-alkyl, aryl, ar-$C_1$–$C_6$-alkyl group and a pharmaceutically acceptable cation, (b) —$NR^{13}$—O—$R^{22}$ wherein $R^{22}$ is a selectively removable protecting group such as a 2-tetrahydropyranyl, benzyl, p-methoxybenzyl (MOZ), carbonyl-$C_1$–$C_6$-alkoxy, trisubstituted silyl group or o-nitrophenyl group, peptide synthesis resin and the like, wherein trisubstituted silyl group is substituted with $C_1$–$C_6$-alkyl, aryl, or ar-$C_1$–$C_6$-alkyl, and $R^{13}$ is a hydrido, $C_1$–$C_6$-alkyl or benzyl group, or (c) —$NR^{13}$—O—$R^{14}$, where $R^{13}$ is as before and $R^{14}$ is a hydrido, a pharmaceutically acceptable cation or C(W)$R^{15}$ group, where W is O or S and $R^{15}$ is selected from the group consisting of an $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, ar-$C_1$–$C_6$-alkoxy, ar-$C_1$–$C_6$-alkyl, heteroaryl and amino $C_1$–$C_6$-alkyl group wherein the aminoalkyl nitrogen is (i) unsubstituted or (ii) substituted with one or two substituents independently selected from the group consisting of an $C_1$–$C_6$-alkyl, aryl, ar-$C_1$–$C_6$-alkyl, $C_3$–$C_8$-cycloalkyl-$C_1$–$C_6$-alkyl, ar-$C_1$–$C_6$-alkoxycarbonyl, $C_1$–$C_6$-alkoxycarbonyl, and $C_1$–$C_6$-alkanoyl radical, or (iii) wherein the amino $C_1$–$C_6$-alkyl nitrogen and two substituents attached thereto form a 5- to 8-membered heterocyclo or heteroaryl ring.

A 5- or 6-membered carbocyclo, heterocyclo, aryl or heteroaryl radical bonded directly to the depicted $SO_2$-group that constitutes an $R^1$ group whose 5- or 6-membered carbocyclo, heterocyclo, aryl or heteroaryl radical of $R^1$ is itself optionally substituted with an —A—R—E—Y substituent. In such an —A—R—E—Y substituent, A is selected from the group consisting of (1) —O—;
(2) —S—;
(3) —$NR^k$—;
(4) —CO—N($R^k$) or —N($R^k$)—CO—;
(5) —CO—O— or —O—CO—;
(6) —O—CO—O—;
(7) —HC=CH—;
(8) —NH—CO—NH—;
(9) —C≡C—;
(10) —N=N—;
(11) —NH—NH—;
(12) —CS—N($R^k$)— or —N($R^k$)—CS—;
(13) —$CH_2$—;
(14) —O—$CH_2$— or —$CH_2$—O—;
(15) —S—$CH_2$— or —$CH_2$—S—;
(16) —SO—; and
(17) —$SO_2$—; or
(18) A is absent and R is directly bonded to the depicted $SO_2$-bonded 5- or 6-membered ring group.

The moiety R is selected from the group consisting of alkyl, alkoxy, halo, alkoxyalkyl, aryl, heteroaryl, cycloalkyl, heterocycloalkyl, aralkyl, heteroaralkyl, heterocycloalkyl, cycloalkyl, cycloalkoxyalkyl, heterocycloalkoxyalkyl, aryloxyalkyl, heteroaryloxy-alkyl, arylthioalkyl, heteroarylthioalkyl, cycloalkylthioalkyl, and a heterocycloalkylthioalkyl group wherein the aryl, heteroaryl, cycloalkyl or heterocycloalkyl substituent is (i) unsubstituted or (ii) substituted with one or two radicals selected from the group consisting of a halo, alkyl, perfluoroalkyl, perfluoroalkoxy, perfluoroalkylthio, trifluoromethylalkyl, amino, alkoxycarbonylalkyl, alkoxy, $C_1$–$C_2$-alkylenedioxy, hydroxycarbonylalkyl, hydroxycarbonylalkylamino, nitro, hydroxy, hydroxyalkyl, alkanoylamino, and a alkoxycarbonyl group.

The group E is selected from the group consisting of (1) —CO($R^g$)— or —($R^g$)CO—;
(2) —CON($R^k$)— or —($R^k$)NCO—;
(3) —CO—;
(4) —$SO_2$—$R^g$ or —$R^gSO_2$—;
(5) —$SO_2$—;
(6) —N($R^k$)—$SO_2$— or —$SO_2$—N($R^k$)—; or
(7) E is absent and R is bonded directly to Y; and
  Y is absent or is selected from the group consisting of a hydrido, alkyl, alkoxy, haloalkyl, aryl, aralkyl, cycloalkyl, heteroaryl, hydroxy, nitrile, nitro, aryloxy, aralkoxy, heteroaryloxy, heteroaralkyl, $R^c$oxyalkyl, perfluoroalkoxy, perfluoroalkylthio, trifluoromethylalkyl, alkenyl, heterocycloalkyl, cycloalkyl, trifluoromethyl, alkoxycarbonyl, and a aminoalkyl group, wherein the aryl, heteroaryl or heterocycloalkyl group is (i) unsubstituted or (ii) substituted with one or two radicals independently selected from the group consisting of an alkanoyl, halo, nitro, nitrile, haloalkyl, alkyl, aralkyl, aryl, alkoxy, and an amino group wherein the amino nitrogen is (i) unsubstituted or (ii) substituted with one or two groups independently selected from hydrido, alkyl, and an aralkyl group.

Preferably, an —$R^1$ substituent is a substituent —G—A—R—E—Y in which
  G is an aryl or heteroaryl group;
  the substituent A is selected from the group consisting of
  (1) —O—;
  (2) —S—;
  (3) —$NR^k$—;
  (4) —CO—N($R^k$) or —N($R^k$)—CO—;

(5) —CO—O— or —O—CO—;
(6) —O—CO—O—;
(7) —HC=CH—;
(8) —NH—CO—NH—;
(9) —C≡C—;
(10) —N=N—;
(11) —NH—NH—;
(12) —CS—N($R^k$)— or —N($R^k$)—CS—;
(13) —CH$_2$—;
(14) —O—CH$_2$— or —CH$_2$—O—;
(15) —S—CH$_2$— or —CH$_2$—S—;
(16) —SO—; and
(17) —SO$_2$—; or
(18) A is absent and R is directly bonded to the N-heterocyclo group, G.

The moiety R is selected from the group consisting of alkyl, alkoxy, halo, alkoxyalkyl, aryl, heteroaryl, cycloalkyl, heterocycloalkyl, aralkyl, heteroaralkyl, heterocycloalkyl, cycloalkyl, cycloalkoxyalkyl, heterocycloalkoxyalkyl, aryloxyalkyl, heteroaryloxyalkyl, arylthioalkyl, heteroarylthioalkyl, cycloalkylthioalkyl, and a heterocycloalkylthioalkyl group wherein the aryl or heteroaryl or cycloalkyl or heterocycloalkyl substituent is (i) unsubstituted or (ii) substituted with one or two radicals selected from the group consisting of a halo, alkyl, perfluoroalkyl, perfluoroalkoxy, perfluoroalkylthio, trifluoromethylalkyl, amino, alkoxycarbonylalkyl, alkoxy, $C_1$-$C_2$-alkylenedioxy, hydroxycarbonylalkyl, hydroxycarbonylalkylamino, nitro, hydroxy, hydroxyalkyl, alkanoylamino, and a alkoxycarbonyl group.

The moiety E is selected from the group consisting of
(1) —CO($R^g$)— or —($R^g$)CO—;
(2) —CON($R^k$)— or —($R^k$)NCO—;
(3) —CO—;
(4) —SO$_2$—$R^g$— or —$R^g$—SO$_2$—;
(5) —SO$_2$—;
(6) —N($R^k$)—SO$_2$— or —SO$_2$—N($R^k$)—; or
(7) E is absent and R is bonded directly to Y; and
the moiety Y is absent or is selected from the group consisting of a hydrido, alkyl, alkoxy, haloalkyl, aryl, aralkyl, cycloalkyl, heteroaryl, hydroxy, nitrile, nitro, aryloxy, aralkoxy, heteroaryloxy, heteroaralkyl, $R^c$oxyalkyl, perfluoroalkoxy, perfluoroalkylthio, trifluoromethylalkyl, alkenyl, heterocycloalkyl, cycloalkyl, trifluoromethyl, alkoxycarbonyl, and a aminoalkyl group, wherein the aryl, heteroaryl or heterocycloalkyl group is (i) unsubstituted or (ii) substituted with one or two radicals independently selected from the group consisting of an alkanoyl, halo, nitro, nitrile, haloalkyl, alkyl, aralkyl, aryl, alkoxy, and an amino group wherein the amino nitrogen is (i) unsubstituted or (ii) substituted with one or two groups independently selected from hydrido, alkyl, and an aralkyl group; and wherein
$R^d$ and $R^e$ are independently selected from the group consisting of a hydrido, alkyl, alkenyl, alkenyl, arylalkyl, aryl, alkanoyl, aroyl, arylalkycarbonyl, alkoxycarbonyl or arylalkyloxycarbonyl group;
$R^f$ is selected from the group consisting of a nitro, hydroxy, alkyl, halogen (halo; F, Cl, Br, I), aryl, alkoxy, cyano, and $R^dR^e$amino group;
$R^g$ is selected from the group consisting of a hydrido, aryl, heteroaryl, heterocyclo, aroyl, alkanoyl, heteroaroyl, halogen (F, Cl, Br, I), cyano, aldehydo (CHO, formyl), hydroxy, amino, alkyl, alkenyl, alkynyl, cycloalkyl, cycloalkenyl, alkoxy, aryloxy, heteroaryloxy, alkenyloxy, alkynyloxy, alkoxyaryl, alkoxyheteroaryl, $R^hR^i$-amino, alkoxyalkyl, alkylenedioxy, aryloxyalkyl, perfluoroalkyl, trifluoroalkyl, alkylthio, arylthio, alkyloxycarbonyl, alkyloxycarbonyloxy, aryloxycarbonyl, arylalkyloxycarbonyl, arylalkyloxycarbonylamino, aryloxycarbonyloxy, carboxy, $R^hR^i$-aminocarbonyloxy, $R^hR^i$-aminocarbonyl, $R^hR^i$-aminoalkanoyl, hydroxyaminocarbonyl, $R^hR^i$-aminosulfonyl, $R^hR^i$-aminocarbonyl($R^h$)amino, trifluoromethylsulfonyl-($R^h$)amino, heteroarylsulfonyl($R^h$)amino, arylsulfonyl($R^h$)amino, arylsulfonyl($R^h$)aminocarbonyl, alkylsulfonyl($R^h$)amino, arylcarbonyl($R^h$)aminosulfonyl, and an alkylsulfonyl($R^h$) aminocarbonyl substituent;
wherein $R^h$ is selected from the group consisting of an arylalkyl, aryl, heteroaryl, heterocyclo, alkyl, alkynyl, alkenyl, alkoxyalkyl, substituted or unsubstituted aminoalkyl, alkyloxycarbonyl, arylalkyloxycarbonyl, carboxyalkyl, haloalkyl, alkanoyl, aroyl, substituted or unsubstituted aminoalkanoyl, halo alkanoyl and a hydroxyalkyl group, each of which groups is optionally substituted by one or two groups independently selected from $R^j$ substituents as are the substituents of the substituted aminoalkyl and substituted aminoalkanoyl groups;
$R^i$ is selected from the group consisting of an arylalkyl, aryl, heteroaryl, heterocyclo, alkyl, alkynyl, alkenyl, alkoxyalkyl, alkoxyalkyl, substituted or unsubstituted aminoalkyl, alkyloxycarbonyl, arylalkyloxycarbonyl, carboxyalkyl, haloalkyl, alkanoyl, aroyl, substituted or unsubstituted aminoalkanoyl, halo alkanoyl and a hydroxyalkyl group, each of which groups are optionally substituted by one or two $R^j$ substituents;
$R^j$ is selected from the group consisting of an arylalkyl, aryl, heteroaryl, heterocyclo, alkyl, alkynyl, alkenyl, alkoxyalkyl, alkoxyalkyl, substituted or unsubstituted aminoalkyl, alkyloxycarbonyl, arylalkyloxycarbonyl, carboxyalkyl, haloalkyl, alkanoyl, aroyl, substituted or unsubstituted aminoalkanoyl, halo alkanoyl and a hydroxyalkyl group, wherein the substituents of the substituted aminoalkyl and substituted aminoalkanoyl groups are selected from the group consisting of an alkyl, alkenyl, alkenyl, aryl, arylalkyl, heteroaryl, heteroarylalkyl, aryloxycarbonyl and an alkyloxycarbonyl group; and
$R^k$ is selected from hydrido, alkyl, alkenyl, alkenyl, aryl, arylalkyl, heteroaryl, heteroarylalkyl, aryloxycarbonyl, alkyloxycarbonyl, $R^cR^d$amino carbonyl, $R^cR^d$aminosulfonyl, $R^cR^d$aminoalkanoyl and $R^cR^d$aminoalkylsulfonyl, and $R^a$, $R^c$, $R^d$, and $R^g$ are as defined hereinbefore.

A process for treating a host mammal having a condition associated with pathological matrix metalloprotease activity is also contemplated. That process comprises administering a compound corresponding in structure to Formula B that selectively inhibits one or more MMPS, while exhibiting less activity against at least MMP-1 in an MMP enzyme-inhibiting effective amount to a mammalian host having such a condition. A contemplated compound also does not substantially inhibit the production of TNF.

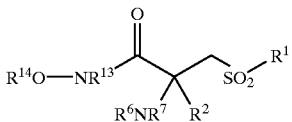

wherein $R^1$, $R^2$, $R^6$, $R^7$, $R^{13}$, and $R^{14}$ are as defined before. Preferably, $R^2$, $R^6$, and $R^{13}$ are hydrido, and $R^7$ is $R^{7A}$, wherein $R^{7A}$ is selected from the group consisting of an alkylcarbonyl, alkoxycarbonyl, arylcarbonyl, alkylsulfonyl, arylsulfonyl, aminoalkylcarbonyl, aminoaralkylcarbonyl, alkoxycarbonylaminoalkylcarbonyl, alkoxycarbonylaminoaralkylcarbonyl, cycloalkoxycarbonylaminoalkylcarbonyl, cycloalkoxycarbonylaminoaralkylcarbonyl, aryloxycarbonylaminoalkylcarbonyl, aryloxycarbonylaminoaralkylcarbonyl, aralkyloxycarbonylaminoalkylcarbonyl, aralkyloxycarbonylaminoalkylcarbonyl, heteroaryloxycarbonylaminoalkylcarbonyl and a heteroaryloxycarbonylaminoaralkylcarbonyl group.

An intermediate compound in the preparation of a particularly preferred compound of Formula A is also contemplated. Such a compound has a structure that corresponds to formula C, below.

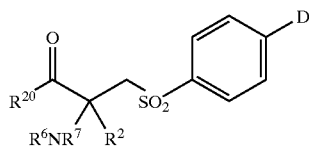

wherein $R^2$, $R^6$, $R^7$ and $R^{20}$ are as before described and D is a nucleophilically-displacable leaving group such as —F or —$NO_2$.

A particularly preferred intermediate for use i preparing a contemplated MMP inhibitor corresponds in structure to Formula D, below, wherein $R^1$, $R^2$, $R^6$, $R^7$ and $R^{13}$ are as before described.

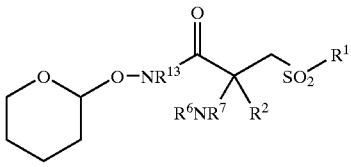

Among the several benefits and advantages of the present invention are the provision of compounds and compositions that are effective for the inhibition of metalloproteinases implicated in diseases and disorders involving uncontrolled breakdown of connective tissue.

More particularly, a benefit of this invention is the provision of a compound and composition effective for inhibiting metalloproteinases, particularly MMP-13 and/or MMP-2, associated with pathological conditions such as, for example, rheumatoid arthritis, osteoarthritis, septic arthritis, corneal, epidermal or gastric ulceration, tumor metastasis, invasion or angiogenesis, periodontal disease, proteinuria, Alzheimer's Disease, coronary thrombosis, plaque formation and bone disease.

An advantage of the invention is the provision of a method for preparing such compounds and compositions. Another benefit is the provision of a method for treating a pathological condition associated with abnormal matrix metalloproteinase activity.

Another benefit of the invention is that a contemplated compound typically exhibits about equal to greater inhibition of MMP-2 as compared to MMP-13, while maintaining sparing (lessened) inhibitory activity against MMP-1.

Another advantage of the invention is the provision of compounds, compositions and methods effective for treating such pathological conditions by selective inhibition of a metalloproteinase such as MMP-13 and MMP-2 associated with such conditions with minimal side effects resulting from inhibition of other proteinases such as MMP-1, whose activity is necessary or desirable for normal body function.

Yet another advantage of a contemplated compound is the selectivity with respect to tumor necrosis factor release and/or tumor necrosis factor receptor release that provides the physician with another factor to help select the best drug for a particular patient. While not wishing to be bound by theory, it is believed that there are several factors to this type of selectivity to be considered.

The first is that presence of tumor necrosis factor can be desirable for the control of cancer in the organism, so long as TNF is not present in a toxic excess. Thus, uncontrolled inhibition of release of TNF can be counterproductive and actually can be considered an adverse side effect even in cancer patients. In addition, selectivity with respect to inhibition of the release of the tumor necrosis factor receptor can also be desirable. The presence of that receptor can be desirable for maintaining a controlled tumor necrosis level in the mammal by binding excess TNF.

Still further benefits and advantages of the invention will be apparent to the skilled worker from the disclosure that follows.

DETAILED DESCRIPTION OF THE INVENTION

In accordance with the present invention, it has been found that certain α-amino-β-sulfonyl carbocyclo, heterocyclo, aryl or heteroaryl hydroxamic acids (hydroxamates) are effective, inter alia, for inhibition of matrix metalloproteinases ("MMPs") believed to be associated with uncontrolled or otherwise pathological breakdown of connective tissue. In particular, it has been found that these certain α-amino-β-sulfonyl carbocyclo, heterocyclo, aryl or heteroaryl hydroxamic acid compounds are effective for inhibition of collagenase III (MMP-13) and also gelatinase A (MMP-2), which can be particularly destructive to tissue if present or generated in abnormal quantities or concentrations, and thus exhibit a pathological activity.

Moreover, it has been discovered that many of these α-amino-β-sulfonyl carbocyclo, heterocyclo, aryl or heteroaryl hydroxamic acids are selective in the inhibition of MMPs associated with diseased conditions without excessive inhibition of other collagenases essential to normal bodily function such as tissue turnover and repair. More particularly, it has been found that particularly preferred α-amino-β-sulfonyl carbocyclo, heterocyclo, aryl or heteroaryl hydroxamic acid compounds are particularly active in inhibiting of MMP-13 and/or MMP-2, while having a limited or minimal effect on MMP-1. This point is discussed in detail hereinafter and is illustrated in the Inhibition Table hereinafter.

One embodiment of the present invention is directed to a α-amino-β-sulfonyl carbocyclo, heterocyclo, aryl or heteroaryl hydroxamic acid compound, a pharmaceutically acceptable salt of such a compound that can act as a matrix metalloprotease enzyme inhibitor, a precursor to such a compound or a pro-drug form of such a compound. A contemplated compound corresponds in structure to Formula A.

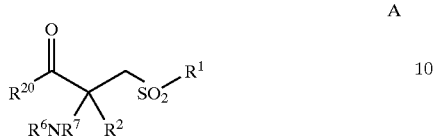

wherein
$R^2$ is selected from the group consisting of a hydrido, $C_1$–$C_4$ hydrocarbyl, hydroxy-$C_1$–$C_4$ hydrocarbyl, $C_1$–$C_4$ hydrocarbyloxymethyl, aryl, aryl $C_1$–$C_4$ hydrocarbyl, aminomethyl, (N—$C_1$–$C_3$ hydrocarbyl) aminomethyl, (N,N-di-$C_1$–$C_3$ hydrocarbyl) aminomethyl, (N-morpholino)methyl, (N-pyrrolidino) methyl, or (N-thiomorpholino)methyl group. $R^2$ is preferably a hydrido, hydroxy, hydroxymethyl, methoxymethyl, $C_1$–$C_4$ hydrocarbyl (e.g. methyl), aryl (phenyl) or methyl-N-morpholinyl group, with phenyl or $C_1$–$C_4$ hydrocarbyl being more preferred;

$R^1$ is a substituent that contains an optionally substituted 5- or 6-membered carbocyclo, heterocyclo, aryl or heteroaryl radical bonded directly to the depicted $SO_2$— group that has a length of an extended pentyl group and less than about that of an extended eicosyl group. In addition, $R^1$ defines a three-dimensional volume that upon rotation about an axis drawn through the $SO_2$—bonded 1-position and the 4-position of a 6-membered ring radical or drawn through the $SO_2$— bonded 1-position and the center of 3,4-bond of a 5-membered ring radical whose widest dimension in a direction transverse to the axis of rotation is about that of one furanyl ring to about that of two phenyl rings; $R^1$ preferably has a length that is greater than an that of an extended hexyl group and less than that of an extended stearyl group.

$R^6$ and $R^7$ are independently selected from the group consisting of a hydrido, alkylcarbonyl, alkoxycarbonyl, arylcarbonyl, aralkylcarbonyl, carboxyalkyl, carboxyalkylcarbonyl, alkoxycarbonylaminoalkylcarbonyl, heterocyclocarbonyl, heterocycloalkylcarbonyl, aryloxycarbonylaminoalkylcarbonyl, aralkyloxycarbonylaminoalkylcarbonyl, perfluoroalkylcarbonyl, trifluoromethylalkylcarbonyl, alkylthioalkylcarbonyl, arylthioalkylcarbonyl, aralkylthioalkylcarbonyl, heteroaralkylthioalkylcarbonyl, or a sulfoxide or sulfone of any of said thio substituents, alkylsulfonyl, arylsulfonyl, and an aminocarbonylalkyl or aminocarbonylalkylcarbonyl group
wherein the aminocarbonylalkyl or aminocarbonylalkylcarbonyl nitrogen is (i) unsubstituted, or (ii) is the reacted amine of an amino acid, or (iii) substituted with one or two radicals selected from the group consisting of an alkyl, hydroxyalkyl, hydroxyheteroaralkyl, cycloalkyl, aralkyl, trifluoromethylalkyl, heterocycloalkyl, benzofused heterocycloalkyl, benzofused heterocycloalkyl, benzofused cycloalkyl, and an N,N-dialkylsubstituted-alkylaminoalkyl group, or (iv) that carboxamido nitrogen and two substituents bonded thereto together form a 5- to 8-membered heterocyclo, heteroaryl or benzofused heterocycloalkyl ring that is itself unsubstituted or substituted with one or two radicals independently selected from the group consisting of an alkyl, alkoxycarbonyl, nitro, heterocycloalkyl, hydroxy, hydroxycarbonyl, aryl, aralkyl, heteroaralkyl and an amino group, or $R^6$ and $R^7$ together with the depicted nitrogen atom form a saturated or unsaturated cyclic imide substituent in which the ring contains five to eight atoms;

$R^6$ is preferably hydrido, and $R^7$ is preferably an alkylcarbonyl, alkoxycarbonyl, arylcarbonyl, alkylsulfonyl, arylsulfonyl, aminoalkylcarbonyl or a substituted aminoalkylcarbonyl group such as an alkoxycarbonylaminoalkylcarbonyl, cycloalkoxycarbonylaminoalkylcarbonyl, aryloxycarbonylaminoalkylcarbonyl, aralkyloxycarbonylaminoalkylcarbonyl, or heteroaryloxycarbonylaminoalkylcarbonyl group;

$R^{20}$ is (a) —O—$R^{21}$, where $R^{21}$ is selected from the group consisting of a hydrido, $C_1$–$C_6$-alkyl, aryl, ar-$C_1$–$C_6$-alkyl group and a pharmaceutically acceptable cation, (b) —$NR^{13}$—O—$R^{22}$ wherein $R^{22}$ is a selectively removable protecting group such as a 2-tetrahydropyranyl, benzyl, p-methoxybenzyl (MOZ), carbonyl-$C_1$–$C_6$-alkoxy, trisubstituted silyl group or o-nitrophenyl group, peptide synthesis resin and the like, wherein trisubstituted silyl group is substituted with $C_1$–$C_6$-alkyl, aryl, or ar-$C_1$–$C_6$-alkyl, and $R^{13}$ is a hydrido, $C_1$–$C_6$-alkyl or benzyl group, or (c) —$NR^{13}$— O—$R^{14}$, where $R^{13}$ is as before and $R^{14}$ is a hydrido, a pharmaceutically acceptable cation or C(W)$R^{15}$ group, where W is O or S and $R^{15}$ is selected from the group consisting of an $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, ar-$C_1$–$C_6$-alkoxy, ar-$C_1$–$C_6$-alkyl, heteroaryl and amino $C_1$–$C_6$-alkyl group wherein the aminoalkyl nitrogen is (i) unsubstituted or (ii) substituted with one or two substituents independently selected from the group consisting of an $C_1$–$C_6$-alkyl, aryl, ar-$C_1$–$C_6$-alkyl, $C_3$–$C_8$-cycloalkyl-$C_1$–$C_6$-alkyl, ar-$C_1$–$C_6$-alkoxycarbonyl, $C_1$–$C_6$-alkoxycarbonyl, and $C_1$–$C_6$-alkanoyl radical, or (iii) wherein the amino $C_1$–$C_6$-alkyl nitrogen and two substituents attached thereto form a 5- to 8-membered heterocyclo or heteroaryl ring.

A 5- or 6-membered carbocyclo, heterocyclo, aryl or heteroaryl radical bonded directly to the depicted $SO_2$— group that constitutes an $R^1$ group that is itself optionally substituted with an —A—R—E—Y substituent. In such an —A—R—E—Y substituent, A is selected from the group consisting of
(1) —O—;
(2) —S—;
(3) —$NR^k$—;
(4) —CO—N($R^k$) or —N($R^k$)—CO—;
(5) —CO—O— or —O—CO—;
(6) —O—CO—O—;
(7) —HC═CH—;
(8) —NH—CO—NH—;
(9) —C≡C—;
(10) —N═N—;
(11) —NH—NH—;
(12) —CS—N($R^k$)— or —N($R^k$)—CS—;

(13) —CH$_2$—;
(14) —O—CH$_2$— or —CH$_2$—O—;
(15) —S—CH$_2$— or —CH$_2$—S—;
(16) —SO—; and
(17) —SO$_2$—; or
(18) A is absent and R is directly bonded to the depicted SO$_2$—bonded 5- or 6-membered ring group.

The moiety R is selected from the group consisting of alkyl, alkoxy, halo, alkoxyalkyl, aryl, heteroaryl, cycloalkyl, heterocycloalkyl, aralkyl, heteroaralkyl, heterocycloalkyl, cycloalkylalkyl, cycloalkoxyalkyl, heterocycloalkoxyalkyl, aryloxyalkyl, heteroaryloxy-alkyl, arylthioalkyl, heteroarylthioalkyl, cycloalkylthioalkyl, and a heterocycloalkylthioalkyl group wherein the aryl, heteroaryl, cycloalkyl or heterocycloalkyl substituent is (i) unsubstituted or (ii) substituted with one or two radicals selected from the group consisting of a halo, alkyl, perfluoroalkyl, perfluoroalkoxy, perfluoroalkylthio, trifluoromethylalkyl, amino, alkoxycarbonylalkyl, alkoxy, C$_1$–C$_2$-alkylenedioxy, hydroxycarbonylalkyl, hydroxycarbonylalkylamino, nitro, hydroxy, hydroxyalkyl, alkanoylamino, and a alkoxycarbonyl group.

The group E is selected from the group consisting of
(1) —CO(R$^g$)— or —(R$^g$)CO—;
(2) —CON(R$^k$)— or —(R$^k$)NCO—;
(3) —CO—;
(4) —SO$_2$—R$^g$ or —R$^g$SO$_2$—;
(5) —SO$_2$—;
(6) —N(R$^k$)—SO$_2$— or —SO$_2$—N(R$^k$)—; or
(7) E is absent and R is bonded directly to Y; and
Y is absent or is selected from the group consisting of a hydrido, alkyl, alkoxy, haloalkyl, aryl, aralkyl, cycloalkyl, heteroaryl, hydroxy, nitrile, nitro, aryloxy, aralkoxy, heteroaryloxy, heteroaralkyl, R$^c$oxyalkyl, perfluoroalkoxy, perfluoroalkylthio, trifluoromethylalkyl, alkenyl, heterocycloalkyl, cycloalkyl, trifluoromethyl, alkoxycarbonyl, and a aminoalkyl group, wherein the aryl, heteroaryl or heterocycloalkyl group is (i) unsubstituted or (ii) substituted with one or two radicals independently selected from the group consisting of an alkanoyl, halo, nitro, nitrile, haloalkyl, alkyl, aralkyl, aryl, alkoxy, and an amino group wherein the amino nitrogen is (i) unsubstituted or (ii) substituted with one or two groups independently selected from hydrido, alkyl, and an aralkyl group.

Preferably, an —R$^1$ substituent is a substituent —G—A—R—E—Y in which
G is an aryl or heteroaryl group;
the substituent A is selected from the group consisting of
(1) —O—;
(2) —S—;
(3) —NR$^k$—;
(4) —CO—N(R$^k$) or —N(R$^k$)—CO—;
(5) —CO——O— or —O—CO—;
(6) —O—CO—O—;
(7) —HC═CH—;
(8) —NH—CO—NH—;
(9) —C≡C—;
(10) —N═N—;
(11) —NH—NH—;
(12) —CS—N(R$^k$)— or —N(R$^k$)—CS—;
(13) —CH$_2$—;
(14) —O—CH$_2$— or —CH$_2$—O—;
(15) —S—CH$_2$— or —CH$_2$—S—;
(16) —SO—; and
(17) —SO$_2$—; or
(18) A is absent and R is directly bonded to the N-heterocyclo group, G.

The moiety R is selected from the group consisting of alkyl, alkoxy, halo, alkoxyalkyl, aryl, heteroaryl, cycloalkyl, heterocycloalkyl, aralkyl, heteroaralkyl, heterocycloalkyl, cycloalkylalkyl, cycloalkoxyalkyl, heterocycloalkoxyalkyl, aryloxyalkyl, heteroaryloxyalkyl, arylthioalkyl, heteroarylthioalkyl, cycloalkylthioalkyl, and a heterocycloalkylthioalkyl group wherein the aryl or heteroaryl or cycloalkyl or heterocycloalkyl substituent is (i) unsubstituted or (ii) substituted with one or two radicals selected from the group consisting of a halo, alkyl, perfluoroalkyl, perfluoroalkoxy, perfluoroalkylthio, trifluoromethylalkyl, amino, alkoxycarbonylalkyl, alkoxy, C$_1$–C$_2$-alkylenedioxy, hydroxycarbonylalkyl, hydroxycarbonylalkylamino, nitro, hydroxy, hydroxyalkyl, alkanoylamino, and a alkoxycarbonyl group.

The moiety E is selected from the group consisting of
(1) —CO(R$^g$)— or —(R$^g$)CO—;
(2) —CON(R$^k$)— or —(R$^k$)NCO—;
(3) —CO—;
(4) —SO$_2$—R$^g$— or —R$^g$—SO$_2$—;
(5) —SO$_2$—;
(6) —N(R$^k$)—SO$_2$— or —SO$_2$—N(R$^k$)—; or
(7) E is absent and R is bonded directly to Y; and
the moiety Y is absent or is selected from the group consisting of a hydrido, alkyl, alkoxy, haloalkyl, aryl, aralkyl, cycloalkyl, heteroaryl, hydroxy, nitrile, nitro, aryloxy, aralkoxy, heteroaryloxy, heteroaralkyl, R$^c$oxyalkyl, perfluoroalkoxy, perfluoroalkylthio, trifluoromethylalkyl, alkenyl, heterocycloalkyl, cycloalkyl, trifluoromethyl, alkoxycarbonyl, and a aminoalkyl group, wherein the aryl, heteroaryl or heterocycloalkyl group is (i) unsubstituted or (ii) substituted with one or two radicals independently selected from the group consisting of an alkanoyl, halo, nitro, nitrile, haloalkyl, alkyl, aralkyl, aryl, alkoxy, and an amino group wherein the amino nitrogen is (i) unsubstituted or (ii) substituted with one or two groups independently selected from hydrido, alkyl, and an aralkyl group; and wherein R$^d$ and R$^e$ are independently selected from the group consisting of a hydrido, alkyl, alkenyl, alkenyl, arylalkyl, aryl, alkanoyl, aroyl, arylalkycarbonyl, alkoxycarbonyl or arylalkyloxycarbonyl group;

R$^f$ is selected from the group consisting of a nitro, hydroxy, alkyl, halogen (halo; F, Cl, Br, I), aryl, alkoxy, cyano, and R$^d$R$^e$amino group;

R$^g$ is selected from the group consisting of a hydrido, aryl, heteroaryl, heterocyclo, aroyl, alkanoyl, heteroaroyl, halogen (F, Cl, Br, I), cyano, aldehydo (CHO, formyl), hydroxy, amino, alkyl, alkenyl, alkynyl, cycloalkyl, cycloalkenyl, alkoxy, aryloxy, heteroaryloxy, alkenyloxy, alkynyloxy, alkoxyaryl, alkoxyheteroaryl, R$^h$R$^i$-amino, alkoxyalkyl, alkylenedioxy, aryloxyalkyl, perfluoroalkyl, trifluoroalkyl, alkylthio, arylthio, alkyloxycarbonyl, alkyloxycarbonyloxy, aryloxycarbonyl, arylalkyloxycarbonyl, arylalkyloxycarbonylamino, aryloxycarbonyloxy, carboxy, R$^h$R$^i$-aminocarbonyloxy, R$^h$R$^i$-aminocarbonyl, R$^h$R$^i$-aminoalkanoyl, hydroxyaminocarbonyl, R$^h$R$^i$-aminosulfonyl, R$^h$R$^i$-aminocarbonyl(R$^h$)amino, trifluoromethylsulfonyl-(R$^h$)amino, heteroarylsulfonyl(R$^h$)amino, arylsulfonyl(R$^h$) amino, arylsulfonyl(R$^h$)aminocarbonyl, alkylsulfonyl(R$^h$)amino, arylcarbonyl(R$^h$) aminosulfonyl, and an alkylsulfonyl(R$^h$) aminocarbonyl substituent;

wherein R$^h$ is selected from the group consisting of an arylalkyl, aryl, heteroaryl, heterocyclo, alkyl, alkynyl, alkenyl, alkoxyalkyl, alkoxyalkyl, substituted or unsubstituted aminoalkyl, alkyloxycarbonyl, arylalkyloxycarbonyl, carboxyalkyl, haloalkyl, alkanoyl, aroyl, substituted or unsubstituted aminoalkanoyl, halo alkanoyl and a hydroxyalkyl group, each of which groups is optionally substituted by one or two groups independently selected from R$^j$ substituents as are the substituents of the substituted aminoalkyl and substituted aminoalkanoyl groups;

R$^i$ is selected from the group consisting of an arylalkyl, aryl, heteroaryl, heterocyclo, alkyl, alkynyl, alkenyl, alkoxyalkyl, alkoxyalkyl, substituted or unsubstituted aminoalkyl, alkyloxycarbonyl, arylalkyloxycarbonyl, carboxyalkyl, haloalkyl, alkanoyl, aroyl, substituted or unsubstituted aminoalkanoyl, halo alkanoyl and a hydroxyalkyl group, each of which groups are optionally substituted by one or two R$^i$ substituents;

R$^j$ is selected from the group consisting of an arylalkyl, aryl, heteroaryl, heterocyclo, alkyl, alkynyl, alkenyl, alkoxyalkyl, alkoxyalkyl, substituted or unsubstituted aminoalkyl, alkyloxycarbonyl, arylalkyloxycarbonyl, carboxyalkyl, haloalkyl, alkanoyl, aroyl, substituted or unsubstituted aminoalkanoyl, halo alkanoyl and a hydroxyalkyl group, wherein the substituents of the substituted aminoalkyl and substituted aminoalkanoyl groups are selected from the group consisting of an alkyl, alkenyl, alkenyl, aryl, arylalkyl, heteroaryl, heteroarylalkyl, aryloxycarbonyl and an alkyloxycarbonyl group; and R$^k$ is selected from hydrido, alkyl, alkenyl, alkenyl, aryl, arylalkyl, heteroaryl, heteroarylalkyl, aryloxycarbonyl, alkyloxycarbonyl, R$^c$R$^d$amino carbonyl, R$^c$R$^d$aminosulfonyl, R$^c$R$^d$aminoalkanoyl and R$^c$R$^d$aminoalkylsulfonyl, and R$^a$, R$^c$, R$^d$, and R$^g$ are as defined hereinbefore.

A more preferred group of contemplated compounds corresponds in structure to Formula B1, below,

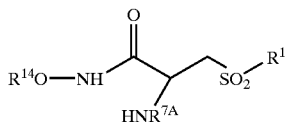

B1 wherein R$^1$ and R$^{14}$ are as defined before, and R$^{7A}$ is selected from the group consisting of an alkylcarbonyl, alkoxycarbonyl, arylcarbonyl, alkylsulfonyl, arylsulfonyl, aminoalkylcarbonyl, aminoaralkylcarbonyl, alkoxycarbonylaminoalkylcarbonyl, alkoxycarbonylaminoaralkylcarbonyl, cycloalkoxycarbonylaminoalkylcarbonyl, cycloalkoxycarbonylaminoaralkylcarbonyl, aryloxycarbonylaminoalkylcarbonyl, aryloxycarbonylaminoaralkylcarbonyl, aralkyloxycarbonylaminoalkylcarbonyl, aralkyloxycarbonylaminoalkylcarbonyl, heteroaryloxycarbonylaminoalkylcarbonyl and a heteroaryloxycarbonylaminoaralkylcarbonyl group.

An intermediate compound useful in the preparation of a particularly preferred compound of Formula A is also contemplated. One such intermediate has a structure that corresponds to formula C, below.

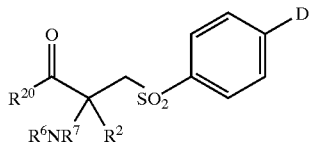

C wherein R$^2$, R$^6$, R$^7$ and R$^{20}$ are as before described and D is a nucleophilically-displacable leaving group such as —F or —NO$_2$. Here, R$^{20}$ is usually —O—R$^{21}$, wherein R$^{21}$ is typically hydrido.

Another particularly preferred intermediate for use in preparing a contemplated MMP inhibitor corresponds in structure to Formula D, below, wherein R$^1$, R$^2$, R$^6$, R$^7$ and R$^{13}$ are as before described.

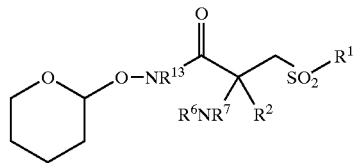

D

Preferably in Formula D, R$^2$, R$^6$ and R$^{13}$ are preferably hydrido, and R$^7$ is preferably R$^{7A}$.

When examined along its longest chain of atoms, an R$^1$ substituent, including its own substituent when present, has a total length that is greater than that of a fully extended saturated chain of five carbon atoms (a pentyl group); i.e., a length of a hexyl chain in staggered conformation or longer. An R$^1$ substituent also has a length that is less than that of a fully extended saturated chain of about 20 carbons (an eicosyl group). Preferably, that length is greater than that of a hexyl group and shorter than that of a stearyl group, even though many more atoms may be present in ring structures or substituents.

Looked at more generally, and aside from specific moieties from which it is constructed, an R$^1$ substituent (radical, group or moiety) has a length of a pentyl group or greater. Such an R$^1$ substituent also has a length that is less than that of an eicosyl group. That is to say that a R$^1$ is a substituent having a length greater than that of a fully extended saturated five carbon chain and shorter than that of a fully extended saturated twenty carbon chain, and more preferably, a length greater than that of a hexyl group and less than that of a stearyl group. The radical chain lengths are measured along the longest linear atom chain in the radical, following the skeletal atoms of a ring where necessary. Each atom in the chain, e.g. carbon, oxygen or nitrogen, is presumed to be carbon for ease in calculation.

Such lengths can be readily determined by using published bond angles, bond lengths and atomic radii, as needed, to draw and measure a chain, or by building models using commercially available kits whose bond angles, lengths and atomic radii are in accord with accepted, published values. Radical (substituent) lengths can also be determined somewhat less exactly by presuming, as is done here, that all atoms have bond lengths of saturated carbon, that unsaturated and aromatic bonds have the same lengths as saturated bonds and that bond angles for unsaturated bonds are the same as those for saturated bonds, although the above-mentioned modes of measurement are preferred. For example, a 4-phenyl or 4-pyridyl group has a length of a four carbon chain, as does a propoxy group, whereas a 4-halophenyl group has the length of a five carbon chain and biphenyl group has the length of about an eight carbon chain using a contemplated measurement mode.

In addition, an $R^1$ substituent, upon rotation about an axis drawn through the $SO_2$-—bonded 1-position and the 4-position of a 6-membered ring radical or the $SO_2$-—bonded 1-position and through the 3,4 bond of a 5-membered ring radical defines a three-dimensional volume whose widest dimension has the width of about one furanyl ring to about the width of two phenyl rings in a direction transverse to that axis to rotation.

When utilizing this width or volume criterion, a fused ring system such as a naphthyl or purinyl radical is considered to be a 6- or 5-membered ring that is substituted at appropriate positions numbered from the $SO_2$-linkage that is deemed to be at the 1-position as discussed before. Thus, a 2-naphthyl substituent or an 8-purinyl substituent is an appropriately sized $R^1$ radical as to width when examined using the above rotational width criterion. On the other hand, a 1-naphthyl group or a 7- or 9-purinyl group is too large upon rotation and is excluded.

As a consequence of these length and width requirements, $R^1$ substituents such as 4-(phenyl)phenyl[biphenyl], 4-(4'-methoxyphenyl)phenyl, 4-(phenoxy)phenyl, 4-(thiophenyl)phenyl[4-(phenylthio)phenyl], 4-(phenylazo)phenyl 4-(phenylureido)phenyl, 4-(anilino)phenyl, 4-(nicotinamido)phenyl, 4-(isonicotinamido)phenyl, 4-(picolinamido)phenyl and 4-(benzamido)phenyl are among particularly preferred $R^1$ substituents, with 4-(phenoxy)phenyl and 4-(thiophenyl)phenyl being most preferred.

An $SO_2$-linked cyclohydrocarbyl, heterocyclo, aryl or heteroaryl radical is a 5- or 6-membered single-ring that is itself substituted with one other substituent, $R^4$. The $SO_2$-linked single-ringed cyclohydrocarbyl, heterocyclo, aryl or heteroaryl radical is $R^4$-substituted at its own 4-position when a 6-membered ring and at its own 3- or 4-position when a 5-membered ring. The cyclohydrocarbyl, heterocyclo, aryl or heteroaryl radical to which $R^4$ is bonded in some embodiments is preferably a phenyl group, so that $R^1$ is preferably $PhR^4$ in which $R^4$ is bonded at the 4-position of the $SO_2$-linked phenyl (Ph) radical, and in which $R^4$ can itself be optionally substituted as is discussed hereinafter. In other embodiments, a heterocyclo or heteroaryl radical is preferred over a phenyl radical, with the $R^4$ substituent being linked at the 4-position relative to the bond between the ring and the $SO_2$ group.

A contemplated $R^4$ substituent can be a single-ringed cyclohydrocarbyl, heterocyclo, aryl or heteroaryl group or another substituent having a chain length of 3 to about 14 carbon atoms such as a hydrocarbyl or hydrocarbyloxy group [e.g., $C_3$-$C_{14}$ hydrocarbyl or O—$C_2$-$C_{14}$ hydrocarbyl], a phenyl group, a phenoxy group [—$OC_6H_5$], a thiophenoxy group [phenylsulfanyl; —$SC_6H_5$], an anilino group [—$NHC_6H_5$], a phenylazo group [—$N_2C_6H_5$], a phenylureido group [aniline carbonylamino; —NHC(O)NH—$C_6H_5$], a benzamido group [—NHC(O)$C_6H_5$], a nicotinamido group [3-NHC(O)$C_5H_4N$], an isonicotinamido group [4-NHC(O)$C_5H_4N$], or a picolinamido group [2-NHC(O)$C_5H_4N$]. Additionally contemplated $R^4$ substituent groups include a heterocyclo, heterocyclohydrocarbyl, arylhydrocarbyl, arylheterocyclohydrocarbyl, heteroarylhydrocarbyl, heteroarylheterocyclo-hydrocarbyl, arylhydrocarbyloxyhydrocarbyl, aryloxyhydrocarbyl, hydrocarboylhydrocarbyl, arylhydrocarboylhydrocarbyl, arylcarbonylhydrocarbyl, arylazoaryl, arylhydrazinoaryl, hydrocarbyl-thiohydrocarbyl, hydrocarbylthioaryl, arylthiohydrocarbyl, heteroarylthiohydrocarbyl, hydrocarbylthioarylhydrocarbyl, arylhydrocarbylthiohydrocarbyl, arylhydrocarbylthioaryl, arylhydrocarbylamino, heteroarylhydrocarbylamino, or a heteroarylthio group.

A contemplated $R^4$ substituent can itself also be substituted with one or more substituent radicals at the meta- or para-position or both of a six-membered ring with a single atom or a substituent containing a longest chain of up to ten atoms, excluding hydrogen. Exemplary substituent radicals include a halo, hydrocarbyl, hydrocarbyloxy, nitro, cyano, perfluorohydrocarbyl, trifluoromethylhydrocarbyl, hydroxy, mercapto, hydroxycarbonyl, aryloxy, arylthio, arylamino, arylhydrocarbyl, aryl, heteroaryloxy, heteroarylthio, heteroarylamino, heteroarhydrocarbyl, hydrocarbyloxycarbonylhydrocarbyl, heterocyclooxy, hydroxycarbonylhydrocarbyl, heterocyclothio, heterocycloamino, cyclohydrocarbyloxy, cyclohydrocarbylthio, cyclohydrocarbylamino, heteroarylhydrocarbyloxy, heteroarylhydrocarbylthio, heteroarylhydrocarbylamino, arylhydrocarbyloxy, arylhydrocarbylthio, arylhydrocarbylamino, heterocyclic, heteroaryl, hydroxycarbonylhydrocarbyloxy, alkoxycarbonylalkoxy, hydrocarbyloyl, arylcarbonyl, arylhydrocarbyloyl, hydrocarboyloxy, arylhydrocarboyloxy, hydroxyhydrocarbyl, hydroxyhydrocarbyloxy, hydrocarbylthio, hydrocarbyloxyhydrocarbylthio, hydrocarbyloxycarbonyl, hydroxycarbonylhydrocarbyloxy, hydrocarbyloxycarbonylhydrocarbyl, hydrocarbylhydroxycarbonylhydrocarbylthio, hydrocarbyloxycarbonylhydrocarbyloxy, hydrocarbyloxycarbonylhydrocarbylthio, amino, hydrocarbylcarbonylamino, arylcarbonylamino, cyclohydrocarbylcarbonylamino, heterocyclohydrocarbylcarbonylamino, arylhydrocarbylcarbonylamino, heteroarylcarbonylamino, heteroarylhydrocarbylcarbonylamino, heterocyclohydrocarbyloxy, hydrocarbylsulfonylamino, arylsulfonylamino, arylhydrocarbylsulfonylamino, heteroarylsulfonylamino, heteroarylhydrocarbylsulfonylamino, cyclohydrocarbylsulfonylamino, heterocyclohydrocarbylsulfonylamino and N-monosubstituted or N,N-disubstituted aminohydrocarbyl group wherein the substituent(s) on the nitrogen are selected from the group consisting of hydrocarbyl, aryl, arylhydrocarbyl, cyclohydrocarbyl, arylhydrocarbyloxycarbonyl, hydrocarbyloxycarbonyl, and hydrocarboyl, or wherein the nitrogen and two substituents attached thereto form a 5- to 8-membered heterocyclic or heteroaryl ring group.

Compounds that are intermediates in the preparation of a MMP-inhibiting compound are also contemplated by this invention. One preferred intermediate corresponds in structure to Formula C, below,

C

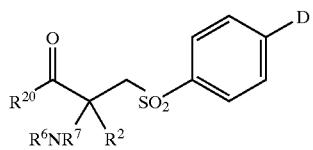

wherein $R^2$, $R^6$, $R^7$ and $R^{20}$ are as before described and D is a nucleophilically-displacable leaving group such as —F or —$NO_2$. $R^2$ and $R^6$ are preferably hydrido here, $R^7$ is preferably $R^{7A}$, and $R^{20}$ is preferably —O—$R^{21}$, wherein $R^{21}$ is hydrido.

Another preferred intermediate compound corresponds in structure to Formula D, below, structure to Formula D, below, wherein $R^1$, $R^2$, $R^6$, $R^7$ and $R^{13}$ are as before described.

D

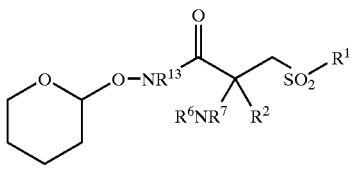

In preferred practice for a compound of Formula D, $R^2$, $R^6$ and $R^{13}$ are hydrido, and $R^7$ is $R^{7A}$.

Table 1 through Table 9, below, illustrate several synthesized compounds that are contemplated by this invention and are useful in a contemplated process. Inhibition data for those compounds in in vitro assays against MMP-1 and MMP-13 are provided hereinafter.

TABLE 1

Example 1

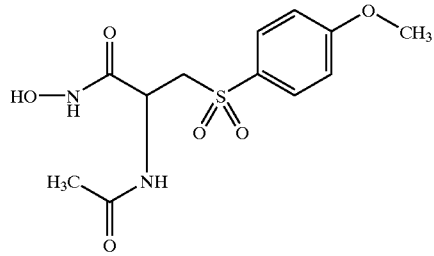

Example 2

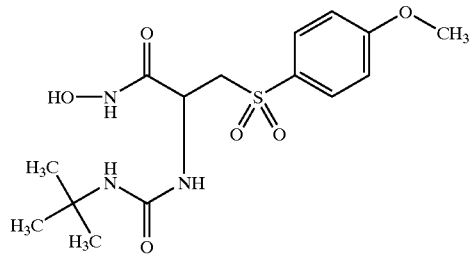

TABLE 1-continued

Example 3

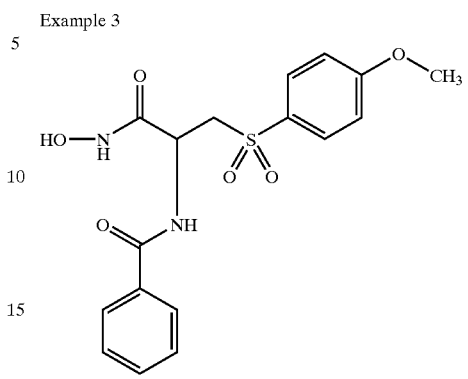

Example 4

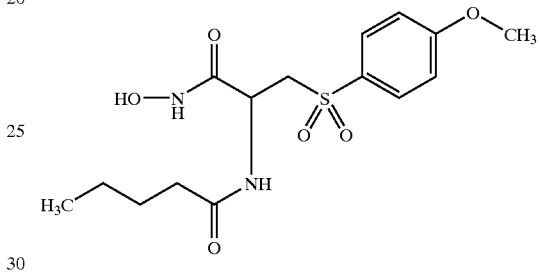

Example 5

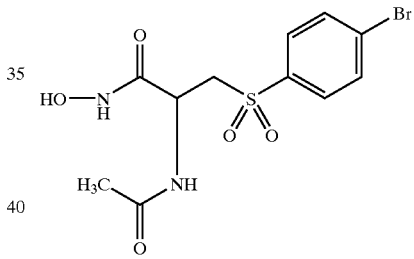

Example 6

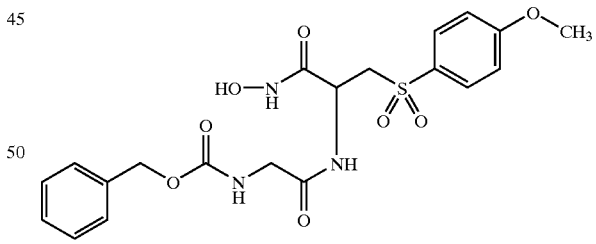

Example 7

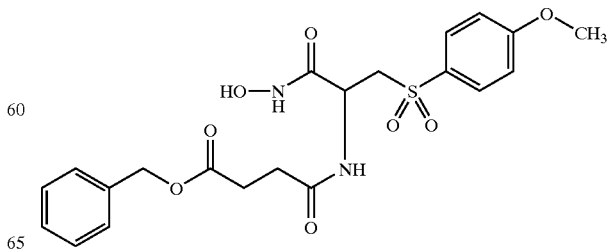

TABLE 1-continued
Example 8
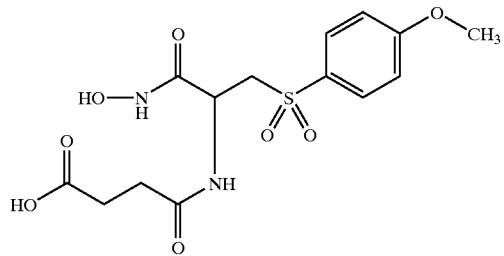
TABLE 2
Example 9g
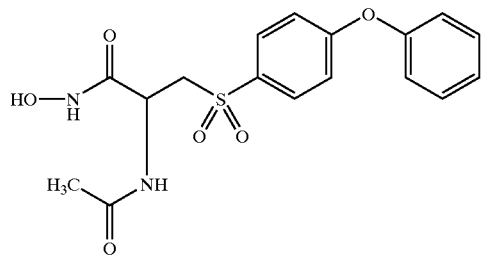
Example 13c
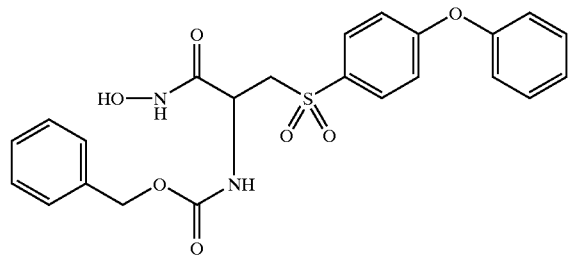
Example 10d
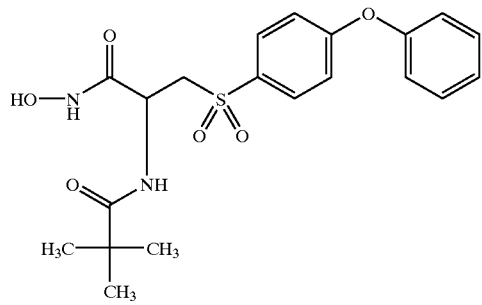
TABLE 2-continued
Example 11g
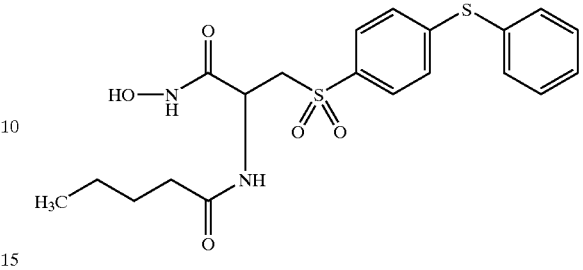
Example 14c
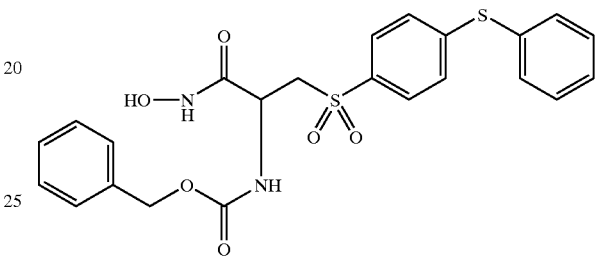
Example 12c
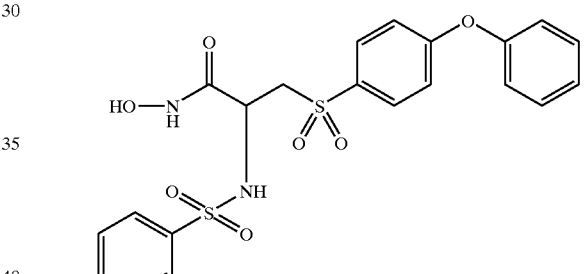
Example 15b
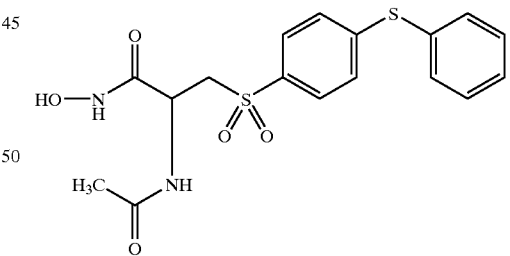
Example 16c
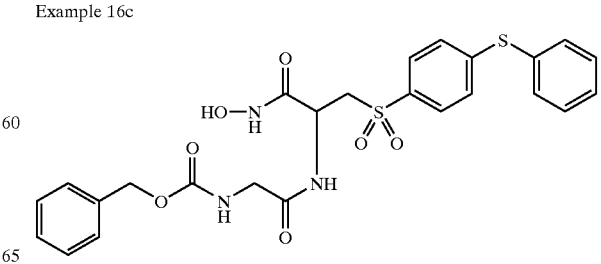

TABLE 3
Example 17c
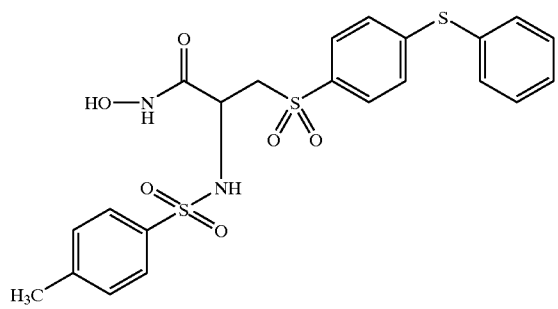
Example 18a
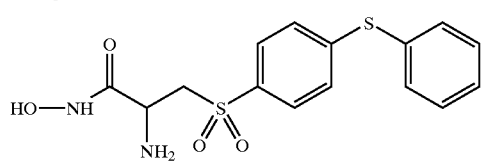
Example 19a
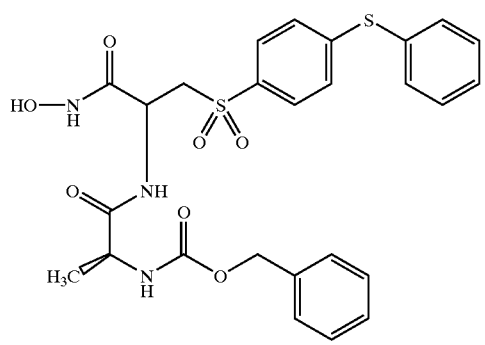
Example 20a
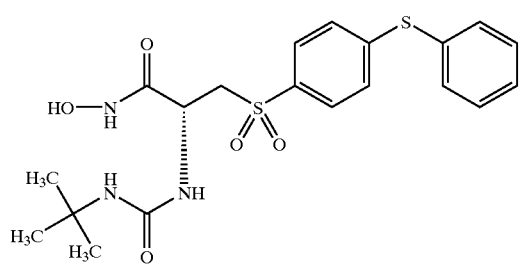
Example 21
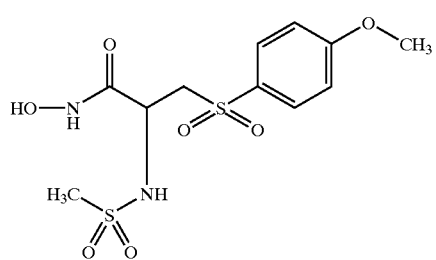
TABLE 3-continued
Example 22
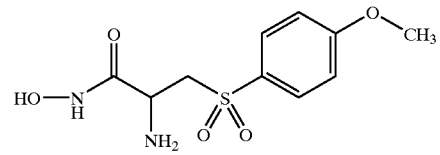
Example 23
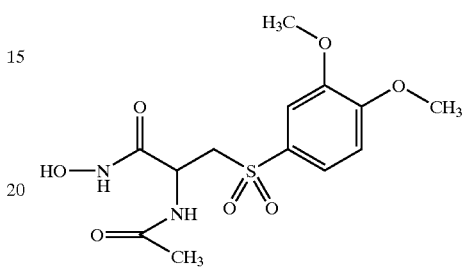
Example 24
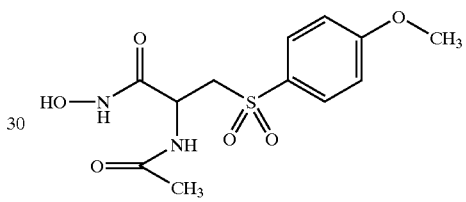
TABLE 4
Example 25
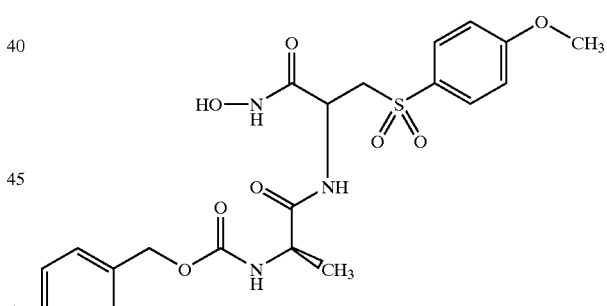
Example 26
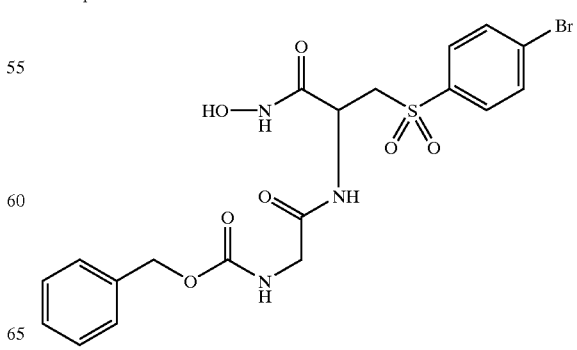

TABLE 4-continued
Example 27
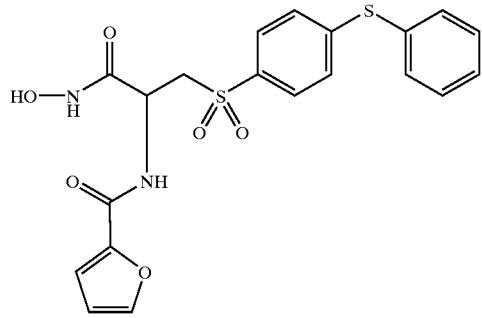
Example 28
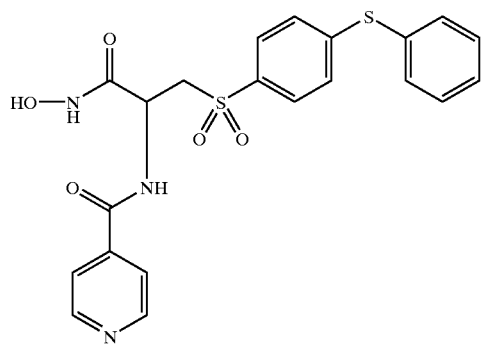
Example 29
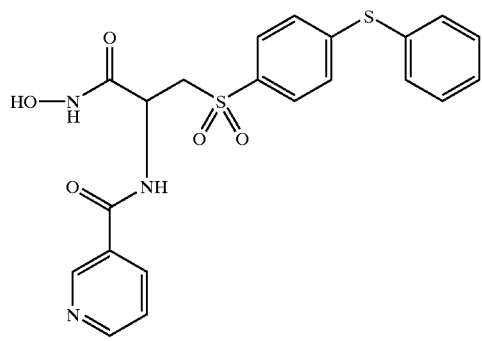
Example 30
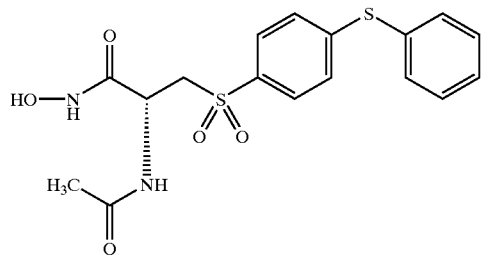
TABLE 4-continued
Example 31
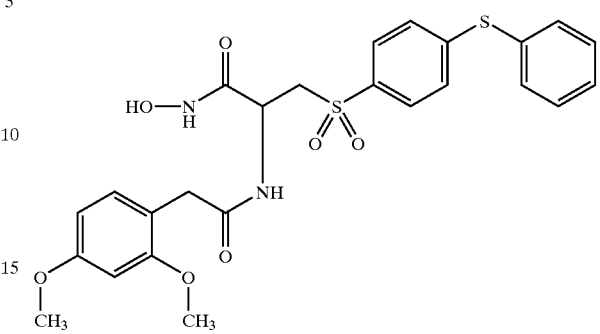
Example 32
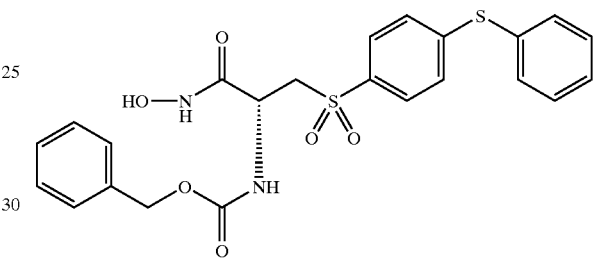
TABLE 5
Example 33
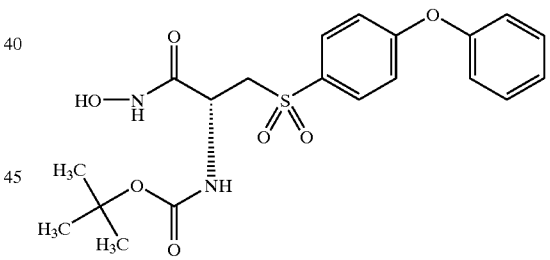
Example 34
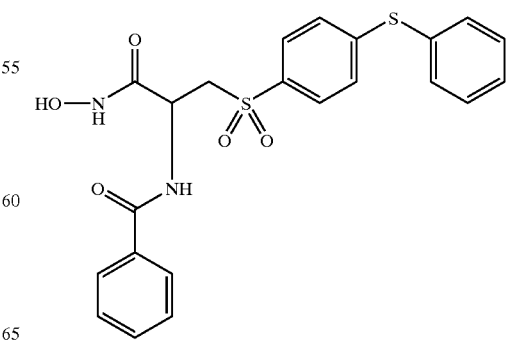

TABLE 5-continued
Example 35
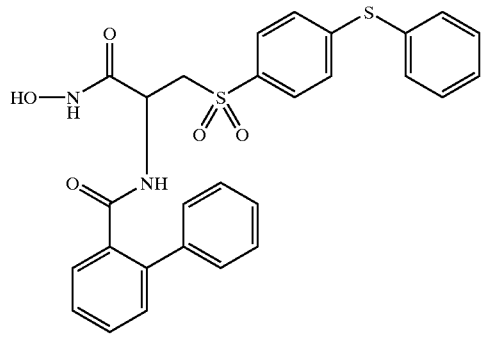
Example 36
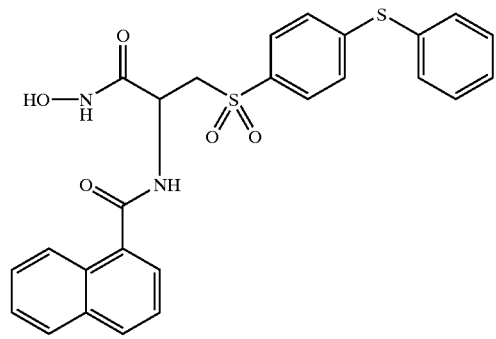
Example 37
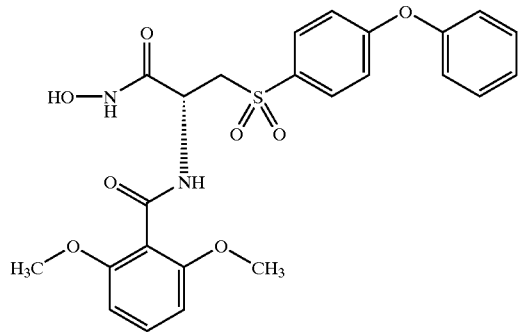
Example 38
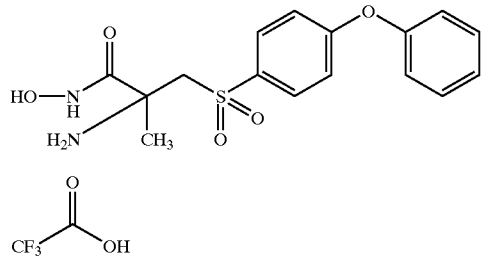
TABLE 5-continued
Example 39
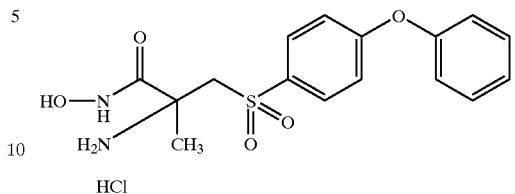
Example 40
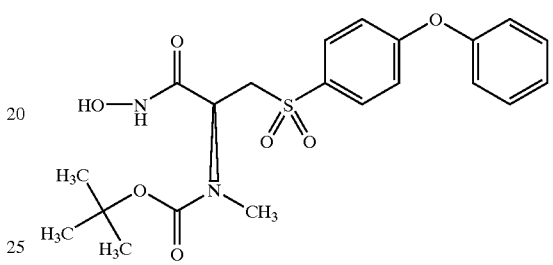
TABLE 6
Example 41
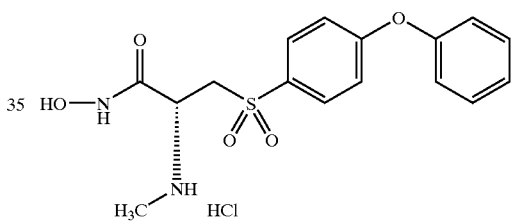
Example 42
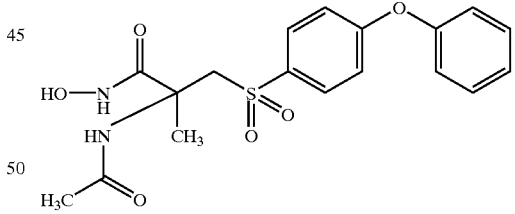
Example 43
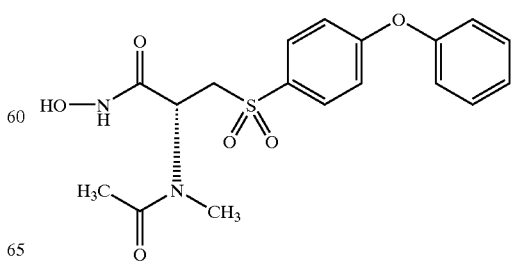

TABLE 6-continued
Example 44
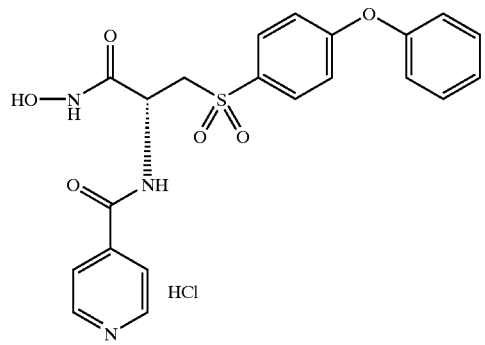
HCl
Example 45
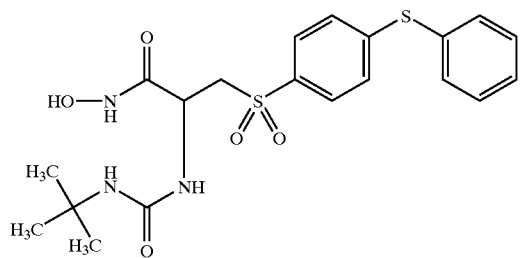
Example 46
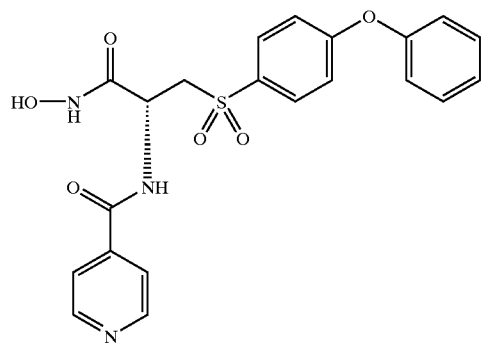
Example 47
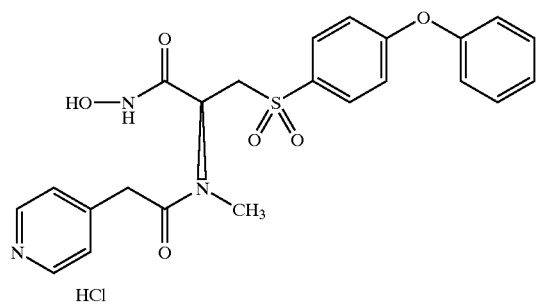
HCl
TABLE 6-continued
Example 48
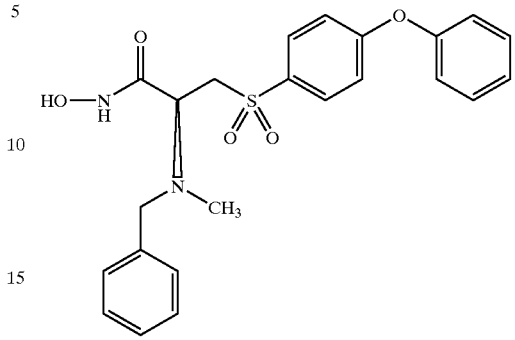
TABLE 7
Example 49
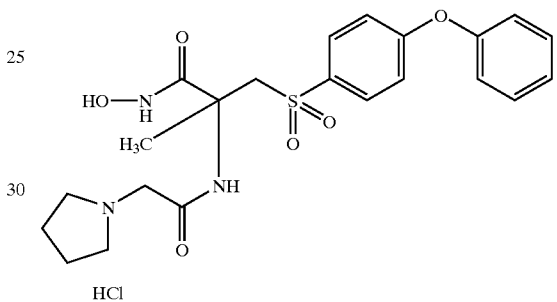
HCl
Example 50
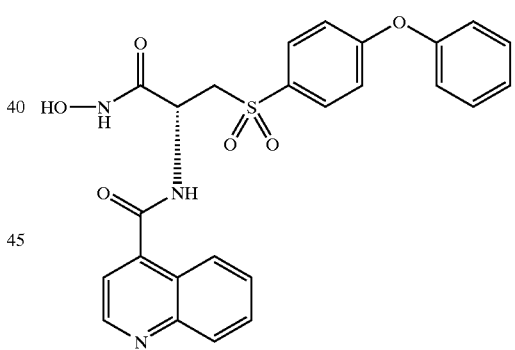
Example 51
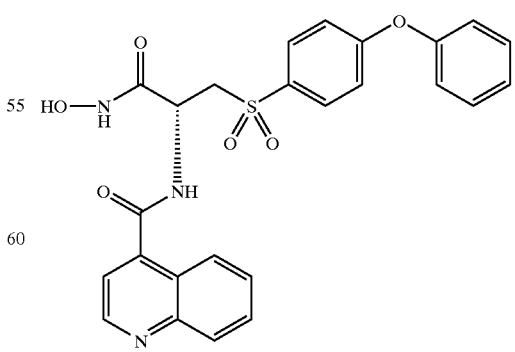
HCl TABLE 7-continued
Example 52
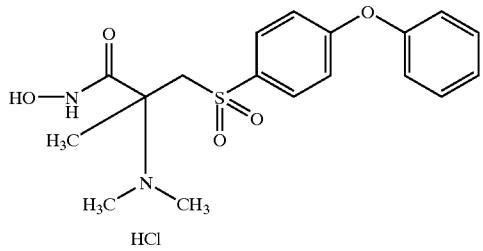
HCl
Example 53
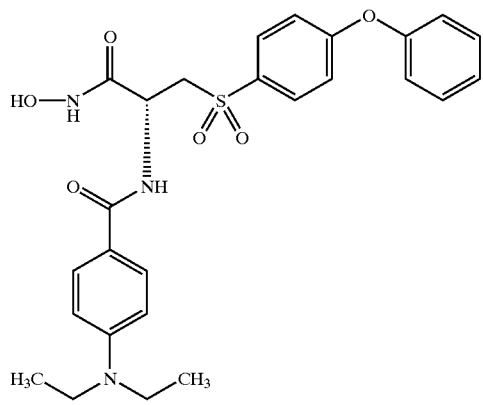
Example 54
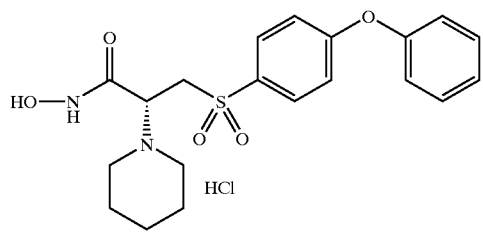
HCl
Example 55
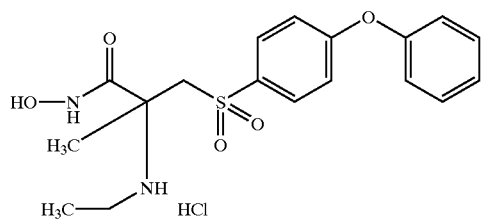
HCl
Example 56
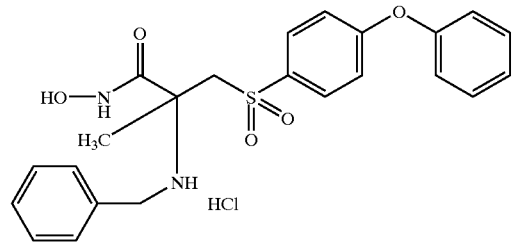
HCl
TABLE 8
Example 57
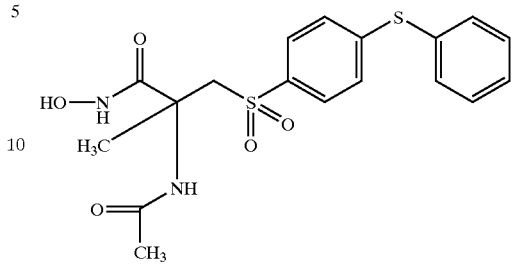
Example 58
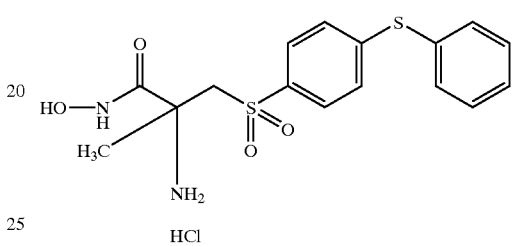
HCl
Example 59
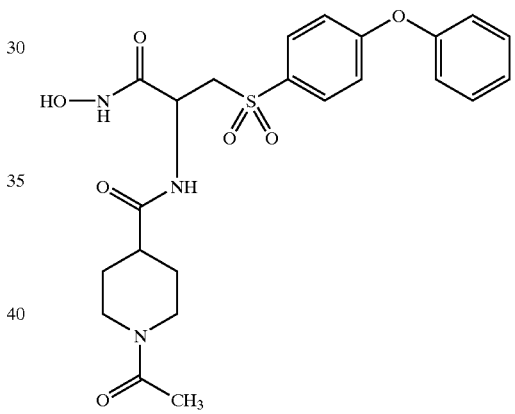
Example 60
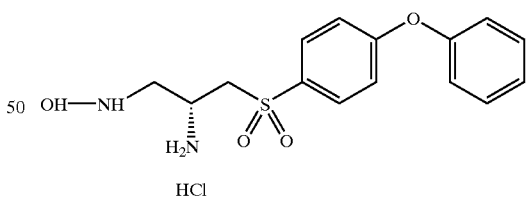
HCl
Example 61
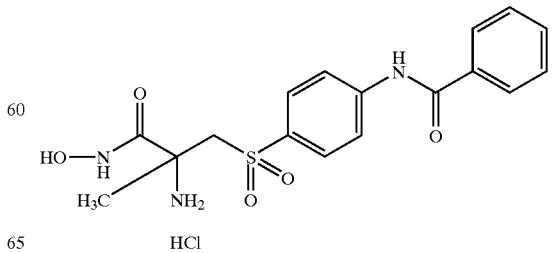
HCl TABLE 8-continued
Example 62
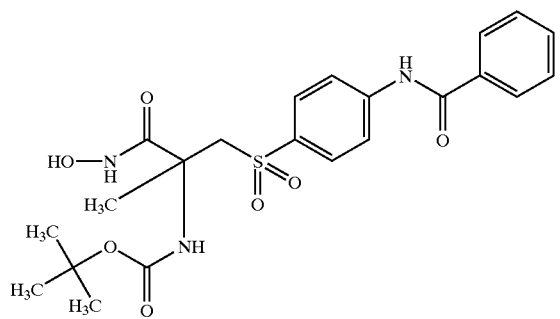
Example 63
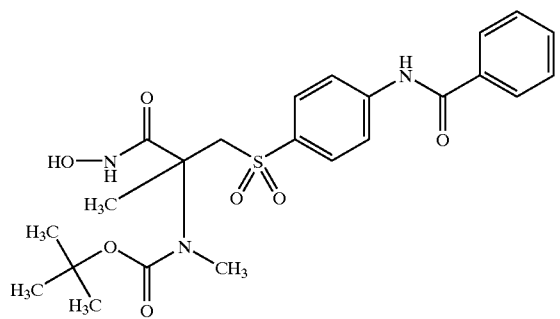
Example 64
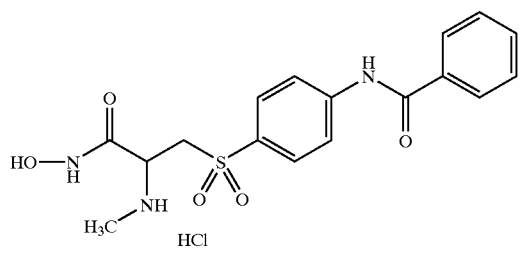
TABLE 9
Example 65
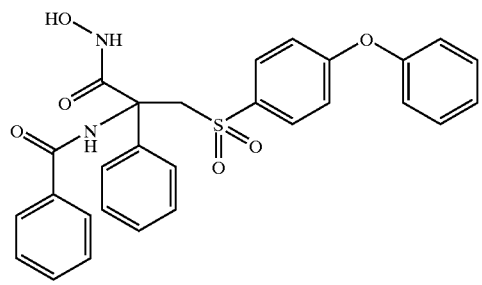
TABLE 9-continued
Example 66
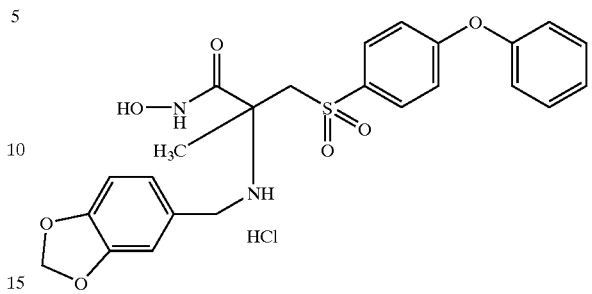
Example 67
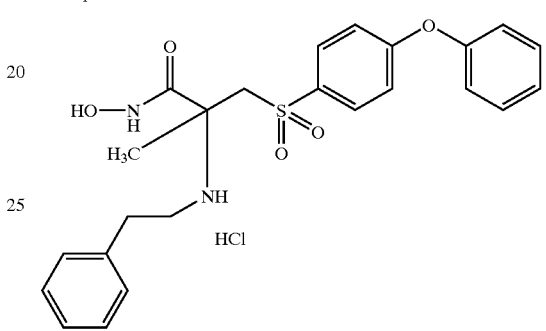
Example 68
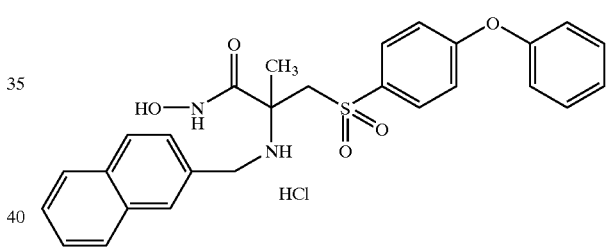
Example 69
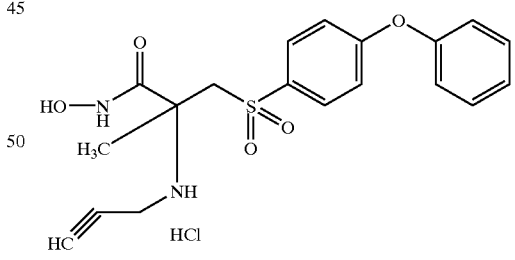
Example 70
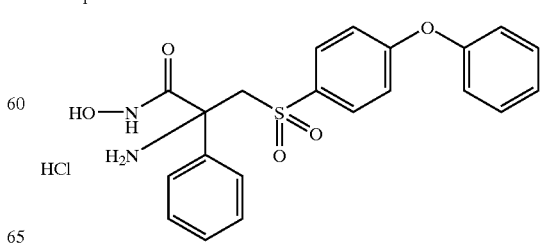

As utilized herein, the term "alkyl", alone or in combination, means a straight-chain or branched-chain alkyl radical containing 1 to about 12 carbon atoms, preferably 1 to about 10 carbon atoms, and more preferably 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "alkenyl", alone or in combination, means a straight-chain or branched-chain hydrocarbon radical having one or more double bonds and containing 2 to about 12 carbon atoms preferably 2 to about 10 carbon atoms, and more preferably, 2 to about 6 carbon atoms. Examples of suitable alkenyl radicals include ethenyl(vinyl), 2-propenyl, 3-propenyl, 1,4-pentadienyl, 1,4-butadienyl, 1-butenyl, 2-butenyl, 3-butenyl, decenyl and the like.

The term "alkynyl", alone or in combination, means a straight-chain hydrocarbon radical having one or more triple bonds and containing 2 to about 12 carbon atoms, preferably 2 to about 10 carbon atoms, and more preferably, 2 to about 6 carbon atoms. Examples of alkynyl radicals include ethynyl, 2-propynyl, 3-propynyl, decynyl, 1-butynyl, 2-butynyl, 3-butynyl, and the like.

The term "carbonyl" or "oxo", alone or in combination, means a —C(=O)— group wherein the remaining two bonds (valences) can be independently substituted. The term carbonyl is also intended to encompass a hydrated carbonyl group —C(OH)$_2$—.

The term "thiol" or "sulfhydryl", alone or in combination, means a —SH group. The term "thio" or "thia", alone or in combination, means a thiaether group; i.e., an ether group wherein the ether oxygen is replaced by a sulfur atom.

The term "amino", alone or in combination, means an amine or —NH$_2$ group whereas the term mono-substituted amino, alone or in combination, means a substituted amine —N(H)(substituent) group wherein one hydrogen atom is replaced with a substituent, and disubstituted amine means a —N(substituent)$_2$ wherein two hydrogen atoms of the amino group are replaced with independently selected substituent groups.

Amines, amino groups and amides are compounds that can be designated as primary (I°), secondary (II°) or tertiary (III°) or unsubstituted, mono-substituted or N,N-disubstituted depending on the degree of substitution of the amino nitrogen. Quaternary amine (ammonium)(IV°) means a nitrogen with four substituents [—N$^+$(substituent)$_4$] that is positively charged and accompanied by a counter ion, whereas N-oxide means one substituent is oxygen and the group is represented as [—N$^+$(substituent)$_3$—O$^-$]; i.e., the charges are internally compensated.

The term "cyano", alone or in combination, means a —C-triple bond-N (—C≡N) group. The term "azido", alone or in combination, means a —N-triple bond-N (—N≡N) group. The term "hydroxyl", alone or in combination, means a —OH group. The term "nitro", alone or in combination, means a —NO$_2$ group. The term "azo", alone or in combination, means a —N=N— group wherein the bonds at the terminal positions can be independently substituted.

The term "hydrazino", alone or in combination, means a —NH—NH— group wherein the depicted remaining two bonds (valences) can be independently substituted. The hydrogen atoms of the hydrazino group can be replaced, independently, with substituents and the nitrogen atoms can form acid addition salts or be quaternized.

The term "sulfonyl", alone or in combination, means a —SO$_2$— group wherein the depicted remaining two bonds (valences) can be independently substituted. The term "sulfoxido", alone or in combination, means a —SO— group wherein the remaining two bonds (valences) can be independently substituted.

The term "sulfone", alone or in combination, means a —SO$_2$— group wherein the depicted remaining two bonds (valences) can be independently substituted. The term "sulfenamide", alone or in combination, means a —SON= group wherein the remaining three depicted bonds (valences) can be independently substituted. The term "sulfide", alone or in combination, means a —S— group wherein the remaining two bonds (valences) can be independently substituted.

The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like.

The term "cycloalkyl", alone or in combination, means a cyclic alkyl radical that contains 3 to about 8 carbon atoms. The term "cycloalkylalkyl" means an alkyl radical as defined above that is substituted by a cycloalkyl radical containing 3 to about 8, preferably 3 to about 6, carbon atoms. Examples of such cycloalkyl radicals include cyclopropyl, cyclobutyl, cyclopentyl, cyclohexyl and the like.

A heterocyclic (heterocyclo) or heterocyclo portion of a heterocyclocarbonyl, heterocyclooxycarbonyl, heterocycloalkoxycarbonyl, or heterocycloalkyl group or the like is a saturated or partially unsaturated monocyclic, bicyclic or tricyclic heterocycle that contains one or more hetero atoms selected from nitrogen, oxygen and sulfur. Heterocyclo compounds include benzofused heterocyclic compounds such as benzo-1,4-dioxane. Such a moiety can be optionally substituted on one or more ring carbon atoms by halogen, hydroxy, hydroxycarbonyl, alkyl, alkoxy, oxo, and the like, and/or on a secondary nitrogen atom (i.e., —NH—) of the ring by alkyl, aralkoxycarbonyl, alkanoyl, aryl or arylalkyl or on a tertiary nitrogen atom (i.e., =N—) by oxido and that is attached via a carbon atom. The tertiary nitrogen atom with three substituents can also attached to form a N-oxide[=N(O)—] group.

The term "aryl", alone or in combination, means a 5- or 6-membered carbocyclic aromatic ring-containing moiety or a fused ring system containing two or three rings that have all carbon atoms in the ring; i.e., a carbocyclic aryl radical. Exemplary carbocyclic aryl radicals include phenyl, indenyl and naphthyl radicals.

The term "heteroaryl", alone or in combination means a 5- or 6-membered aromatic ring-containing moiety or a fused ring system (radical) containing two or three rings that have carbon atoms and also one or more heteroatoms in the ring(s) such as sulfur, oxygen and nitrogen. Examples of such heterocyclic or heteroaryl groups are pyrrolidinyl, piperidyl, piperazinyl, morpholinyl, thiamorpholinyl, pyrrolyl, imidazolyl (e.g., imidazol-4-yl, 1-benzyloxycarbonylimidazol-4-yl, and the like), pyrazolyl, pyridyl, pyrazinyl, pyrimidinyl, furyl, tetrahydrofuryl, thienyl, triazolyl, oxazolyl, oxadiazoyl, thiazolyl, thiadiazoyl, indolyl (e.g., 2-indolyl, and the like), quinolinyl, (e.g., 2-quinolinyl, 3-quinolinyl, 1-oxido-2-quinolinyl, and the like), isoquinolinyl (e.g., 1-isoquinolinyl, 3-isoquinolinyl, and the like), tetrahydroquinolinyl (e.g., 1,2,3,4-tetrahydro-2-quinolyl, and the like), 1,2,3,4-tetrahydroisoquinolinyl (e.g., 1,2,3,4-tetrahydro-1-oxo-isoquinolinyl, and the like), quinoxalinyl, β-carbolinyl, 2-benzofurancarbonyl, benzothiophenyl, 1-, 2-, 4- or 5-benzimidazolyl, and the like radicals.

When an aryl or heteroaryl radical is a substituting moiety (group, substituent, or radical), it can itself substituted, the last-named substituent is independently selected from the group consisting of a cyano, perfluoroalkyl, trifluoromethoxy, trifluoromethylthio, haloalkyl, trifluoromethylalkyl, aralkoxycarbonyl, aryloxycarbonyl, hydroxy, halo, alkyl, alkoxy, nitro, thiol, hydroxycarbonyl, aryloxy, arylthio, aralkyl, aryl, arylcarbonylamino, heteroaryloxy, heteroarylthio, heteroaralkyl, cycloalkyl, heterocyclooxy, heterocyclothio, heterocycloamino, cycloalkyloxy, cycloalkylthio, heteroaralkoxy, heteroaralkylthio, aralkoxy, aralkylthio, aralkylamino, heterocyclo, heteroaryl, arylazo, hydroxycarbonylalkoxy, alkoxycarbonylalkoxy, alkanoyl, arylcarbonyl, aralkanoyl, alkanoyloxy, aralkanoyloxy, hydroxyalkyl, hydroxyalkoxy, alkylthio, alkoxyalkylthio, alkoxycarbonyl, aryloxyalkoxyaryl, arylthioalkylthioaryl, aryloxyalkylthioaryl, arylthioalkoxyaryl, hydroxycarbonylalkoxy, hydroxycarbonylalkylthio, alkoxycarbonylalkoxy, alkoxycarbonylalkylthio, amino,
  wherein the amino nitrogen is (i) unsubstituted, or (ii) substituted with one or two substituents that are independently selected from the group consisting of an alkyl, aryl, heteroaryl, aralkyl, cycloalkyl, aralkoxycarbonyl, alkoxycarbonyl, arylcarbonyl, aralkanoyl, heteroarylcarbonyl, heteroaralkanoyl and an alkanoyl group, or (iii) wherein the amino nitrogen and two substituents attached thereto form a 5- to 8-membered heterocyclo or heteroaryl ring containing zero to two additional heteroatoms that are nitrogen, oxygen or sulfur and which ring itself is (a) unsubstituted or (b) substituted with one or two groups independently selected from the group consisting of an aryl, alkyl, heteroaryl, aralkyl, heteroaralkyl, hydroxy, alkoxy, alkanoyl, cycloalkyl, heterocycloalkyl, alkoxycarbonyl, hydroxyalkyl, trifluoromethyl, benzofused heterocycloalkyl, hydroxyalkoxyalkyl, aralkoxycarbonyl, hydroxycarbonyl, aryloxycarbonyl, benzofused heterocycloalkoxy, benzofused cycloalkylcarbonyl, heterocycloalkylcarbonyl, and a cycloalkylcarbonyl group, carbonylamino
  wherein the carbonylamino nitrogen is (i) unsubstituted, or (ii) is the reacted amine of an amino acid, or (iii) substituted with one or two radicals selected from the group consisting of an alkyl, hydroxyalkyl, hydroxyheteroaralkyl, cycloalkyl, aralkyl, trifluoromethylalkyl, heterocycloalkyl, benzofused heterocycloalkyl, benzofused heterocycloalkyl, benzofused cycloalkyl, and an N,N-dialkylsubstituted alkylamino-alkyl group, or (iv) the carboxamido nitrogen and two substituents bonded thereto together form a 5- to 8-membered heterocyclo, heteroaryl or benzofused heterocycloalkyl ring that is itself unsubstituted or substituted with one or two radicals independently selected from the group consisting of an alkyl, alkoxycarbonyl, nitro, heterocycloalkyl, hydroxy, hydroxycarbonyl, aryl, aralkyl, heteroaralkyl and an amino group,
  wherein the amino nitrogen is (i) unsubstituted, or (ii) substituted with one or two substituents that are independently selected from the group consisting of alkyl, aryl, and heteroaryl, or (iii) wherein the amino nitrogen and two substituents attached thereto form a 5- to 8-membered heterocyclo or heteroaryl ring, and an aminoalkyl group
    wherein the aminoalkyl nitrogen is (i) unsubstituted, or (ii) substituted with one or two substituents independently selected from the group consisting of an alkyl, aryl, aralkyl, cycloalkyl, aralkoxycarbonyl, alkoxycarbonyl, and an alkanoyl group, or (iii) wherein the aminoalkyl nitrogen and two substituents attached thereto form a 5- to 8-membered heterocyclo or heteroaryl ring.

The term "aralkyl", alone or in combination, means an alkyl radical as defined above in which one hydrogen atom is replaced by an aryl radical as defined above, such as benzyl, 2-phenylethyl and the like.

The term "aralkoxycarbonyl", alone or in combination, means a radical of the formula aralkyl-O—C(O)— in which the term "aralkyl" has the significance given above. An example of an aralkoxycarbonyl radical is benzyloxycarbonyl.

The term "aryloxy" means a radical of the formula aryl-O— in which the term aryl has the significance given above. The phenoxy radical is an exemplary aryloxy radical.

The terms "heteroaralkyl" and "heteroaryloxy" mean radicals structurally similar to aralkyl and aryloxy that are formed from heteroaryl radicals. Exemplary radicals include 4-picolinyl and 2-pyrimidinoxy, respectively.

The terms "alkanoyl" or "alkylcarbonyl", alone or in combination, means an acyl radical derived from an alkanecarboxylic acid, examples of which include formyl, acetyl, propionyl, butyryl, valeryl, 4-methylvaleryl, and the like.

The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benzofused monocyclic cycloalkanecarboxylic acid that is optionally substituted by, for example, alkanoylamino, such as 1,2,3,4-tetrahydro-2-naphthoyl, 2-acetamido-1,2,3,4-tetrahydro-2-naphthoyl.

The terms "aralkanoyl" or "aralkylcarbonyl" mean an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-methoxyhydrocinnamoyl and the like.

The terms "aroyl" or "arylcarbonyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl) benzoyl, 1-naphthoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "cycloalkylalkoxycarbonyl" means an acyl group of the formula cycloalkylalkyl-O—CO— wherein cycloalkylalkyl has the significance given above. The term "aryloxyalkanoyl" means an acyl radical of the formula aryl-O-alkanoyl wherein aryl and alkanoyl have the significance given above. The term "heterocyclooxycarbonyl" means an acyl group having the formula heterocyclo-O—CO— wherein heterocyclo is as defined above.

The term "heterocycloalkanoyl" is an acyl radical of the formula heterocyclo-substituted alkane carboxylic acid wherein heterocyclo has the significance given above. The term "heterocycloalkoxycarbonyl" means an acyl radical of the formula heterocyclo-substituted alkane-O—CO— wherein heterocyclo has the significance given above. The term "heteroaryloxycarbonyl" means an acyl radical represented by the formula heteroaryl-O—CO— wherein heteroaryl has the significance given above.

The term "aminocarbonyl" (carboxamide) alone or in combination, means an amino-substituted carbonyl (carbamoyl) group derived from an amine reacted with a carboxylic acid wherein the amino (amido nitrogen) group is unsubstituted (—$NH_2$) or a substituted primary or secondary amino group containing one or two substituents selected from the group consisting of hydrogen, alkyl, aryl, aralkyl, cycloalkyl, cycloalkylalkyl radicals and the like, as recited. A hydroxamate is a N-hydroxycarboxamide.

The term "aminoalkanoyl" means an acyl group derived from an amino-substituted alkanecarboxylic acid wherein the amino group can be a primary or secondary amino group containing substituents independently selected from hydrogen, alkyl, aryl, aralkyl, cycloalkyl, cycloalkylalkyl radicals and the like.

The term "halogen" or "halo" means fluoride, chloride, bromide or iodide. The term "haloalkyl" means an alkyl radical having the significance as defined above wherein one or more hydrogens are replaced with a halogen. Examples of such haloalkyl radicals include chloromethyl, 1-bromoethyl, fluoromethyl, difluoromethyl, trifluoromethyl, 1,1,1-trifluoroethyl and the like.

The term "perfluoroalkyl" means an alkyl group wherein each hydrogen has been replaced by a fluorine atom. Examples of such perfluoroalkyl groups, in addition to trifluoromethyl above, are perfluorobutyl, perfluoroisopropyl, perfluorododecyl and perfluorodecyl.

The term "perfluoroalkoxy" alone or in combination, means a perfluoroalkyl ether radical wherein the term perfluoroalkyl is as defined above. Examples of such perfluoroalkoxy groups, in addition to trifluoromethoxy ($F_3C$—O—), are perfluorobutoxy, perfluoroisopropoxy, perfluorododecyloxy and perfluorodecyloxy.

The term "perfluoroalkylthio" alone or in combination, means a perfluoroalkyl thioether radical wherein the term perfluoroalkyl is as defined above. Examples of such perfluoroalkylthio groups, in addition to trifluoromethylthio ($F_3C$—S—), are perfluorobutylthio, perfluoroisopropylthio, perfluorododecylthio and perfluorodecylthio.

The term "aromatic ring" in combinations such as substituted-aromatic ring sulfone or substituted-aromatic ring sulfoxide means aryl or heteroaryl as defined before.

The term "pharmaceutically acceptable" is used adjectivally herein to mean that the modified noun is appropriate for use in a pharmaceutical product. Pharmaceutically acceptable cations include metallic ions and organic ions. More preferred metallic ions include, but are not limited to appropriate alkali metal (Group Ia) salts, alkaline earth metal (Group IIa) salts and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine(N-methylglucamine) and procaine. Exemplary pharmaceutically acceptable acids include without limitation hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid oxalacetic acid, fumaric acid, propionic acid, aspartic acid, glutamic acid, benzoic acid, and the like.

Treatment Process

A process for treating a host mammal having a condition associated with pathological matrix metalloprotease activity is also contemplated. That process comprises administering a compound corresponding in structure to Formula B that selectively inhibits one or more MMPs, while exhibiting less activity against at least MMP-1, in an MMP enzyme-inhibiting effective amount to a mammalian host having such a condition. A contemplated compound also does not substantially inhibit the production of TNF. The use of administration repeated a plurality of times is particularly contemplated.

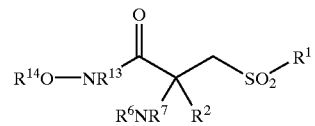

B wherein $R^1$, $R^2$, $R^6$, $R^7$, $R^{13}$, and $R^{14}$ are as defined before.

A more preferred group of contemplated compounds for use in such a process corresponds in structure to Formula B1, below,

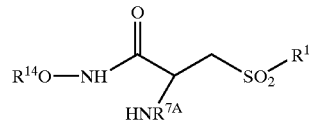

B1 wherein $R^1$ and $R^{14}$ are as defined before, and is a substituent selected from the group consisting of an alkylcarbonyl, alkoxycarbonyl, arylcarbonyl, alkylsulfonyl, arylsulfonyl, aminoalkylcarbonyl, aminoaralkylcarbonyl, alkoxycarbonylaminoalkylcarbonyl, alkoxycarbonylaminoaralkylcarbonyl, cycloalkoxycarbonylaminoalkylcarbonyl, cycloalkoxycarbonylaminoaralkylcarbonyl, aryloxycarbonylaminoalkylcarbonyl, aryloxycarbonylaminoaralkylcarbonyl, aralkyloxycarbonylaminoalkylcarbonyl, aralkyloxycarbonylaminoalkylcarbonyl, heteroaryloxycarbonylaminoalkylcarbonyl and a heteroaryloxycarbonylaminoaralkylcarbonyl group.

A contemplated compound is used for treating a host mammal such as a mouse, rat, rabbit, dog, horse, primate such as a monkey, chimpanzee or human that has a condition associated with pathological matrix metalloprotease activity.

Also contemplated is the similar use of a contemplated compound in the treatment of a disease state that can be affected by the activity of metalloproteases such as TNF-α convertase. Exemplary of such disease states are the acute phase responses of shock and sepsis, coagulation responses, hemorrhage and cardiovascular effects, fever and inflammation, anorexia and cachexia.

In treating a disease condition associated with pathological matrix metalloproteinase activity, a contemplated MMP inhibitor compound can be used, where appropriate, in the form of an amine salt derived from an inorganic or organic acid. Exemplary acid salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate.

Also, a basic nitrogen-containing group can be quaternized with such agents as lower alkyl($C_1$–$C_6$)halides, such as methyl, ethyl, propyl, and butyl chloride, bromides, and iodides; dialkyl sulfates like dimethyl, diethyl, dibuytl, and diamyl sulfates, long chain ($C_8$–$C_{20}$)halides such as decyl, lauryl, myristyl and dodecyl chlorides, bromides and iodides, aralkyl halides like benzyl and phenethyl bromides, and others to provide enhanced water-solubility. Water or oil-soluble or dispersible products are thereby obtained as desired. The salts are formed by combining the basic compounds with the desired acid.

Other compounds useful in this invention that are acids can also form salts. Examples include salts with alkali metals or alkaline earth metals, such as sodium, potassium, calcium or magnesium or with organic bases or basic quaternary ammonium salts.

In some cases, the salts can also be used as an aid in the isolation, purification or resolution of the compounds of this invention.

Total daily dose administered to a host mammal in single or divided doses of an MMP enzyme-inhibiting effective amount can be in amounts, for example, of about 0.001 to about 100 mg/kg body weight daily, preferably about 0.001 to about 30 mg/kg body weight daily and more usually about 0.01 to about 10 mg. Dosage unit compositions can contain such amounts or submultiples thereof to make up the daily dose. A suitable dose can be administered, in multiple sub-doses per day. Multiple doses per day can also increase the total daily dose, should such dosing be desired by the person prescribing the drug.

The dosage regimen for treating a disease condition with a compound and/or composition of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed can vary widely and therefore can deviate from the preferred dosage regimen set forth above.

A compound useful in the present invention can be formulated as a pharmaceutical composition. Such a composition can then be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches or iontophoresis devices. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono- di- or triglycerides, fatty acids and polyethylene glycols that are sold at ordinary temperatures but liquid at the rectal temperature and will therefore melt in the rectum and release the drug.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form varies depending upon the mammalian host treated and the particular mode of administration.

Compound Preparation

A contemplated compound can be prepared by several routes of synthesis as can be seen from the specific Examples that follow. In addition, Schemes 1A and 1B, below, illustrate exemplary synthetic procedures and the use of preferred intermediates in the preparation of contemplated compounds.

Thus, as is seen in Scheme 1A, methyl N-acetylacrylate, compound 1, is reacted in a solvent such as methanol with p-fluorothiophenol in the presence of triethylamine at zero degrees C. via a Michael addition (step 1) and the resulting fluorophenylthioether is oxidized with Oxone® to form the corresponding sulfone, compound 2, in step 2. Hydrolysis of the methyl ester in glacial acetic acid containing hydrochloric acid at zero degrees C. provides the corresponding acid, compound 3. Reaction of compound 3 with thiophenol in DMF at about 10° C. in the presence of potassium carbonate provides the thiophenylether, compound 4. The N-acetyl group is cleaved by reaction of compound 4 in glacial acetic acid and hydrochloric acid at 11° C. to provide the amine hydrochloride, compound 5.

Reaction of compound 5 in water with an N-protected amino acid such ad CBZ-glycine (CBZ-Gly) in the presence of a water-soluble carbodiimide [1-ethyl-3-[3-(dimethylamino)-propyl]carbodiimide hydrochloride; EDC], 1-hydroxybenzotriazole (HOBT) and N-methylmorpholine (NMM) provides the corresponding N-aryloxycarbonylaminoalkylcarbonyl derivative, compound 6, that is shown in Scheme 1B. Reaction of compound 6 with O-tetrahydro-2H-pyran-2-yl-hydroxylamine in THF in the presence of HOBT and EDC provides the THP-protected hydroxamic acid, Compound 7. Reaction of compound 7 with an acid such as toluenesufonic acid of hydrochloric acid cleaves the THP protecting group to provide the hydroxamic acid, compound 8.

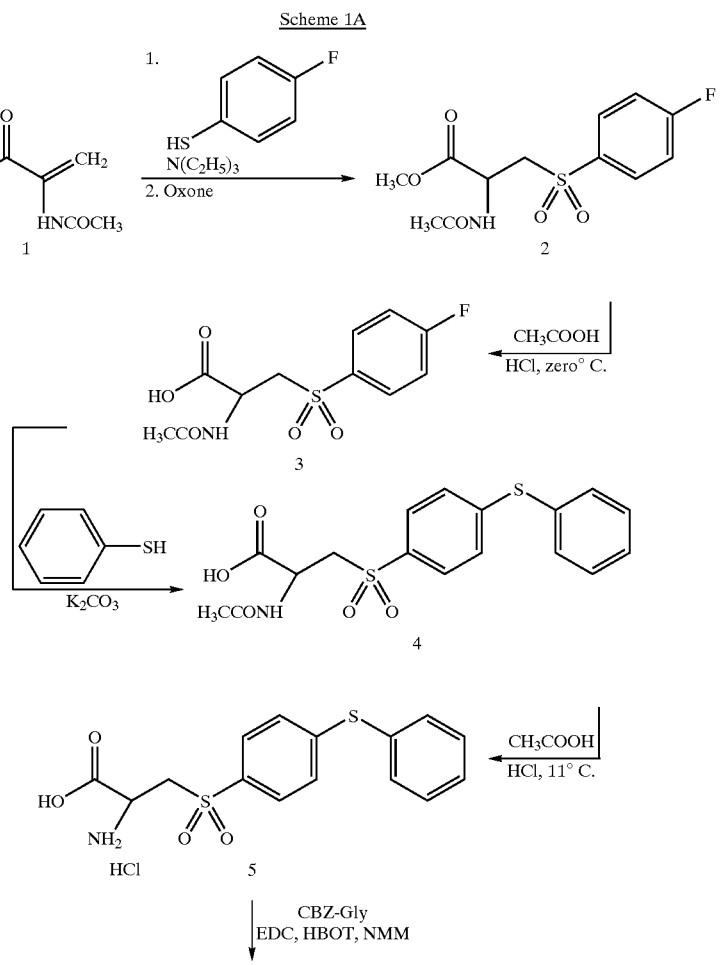

Scheme 1A

Scheme 1B

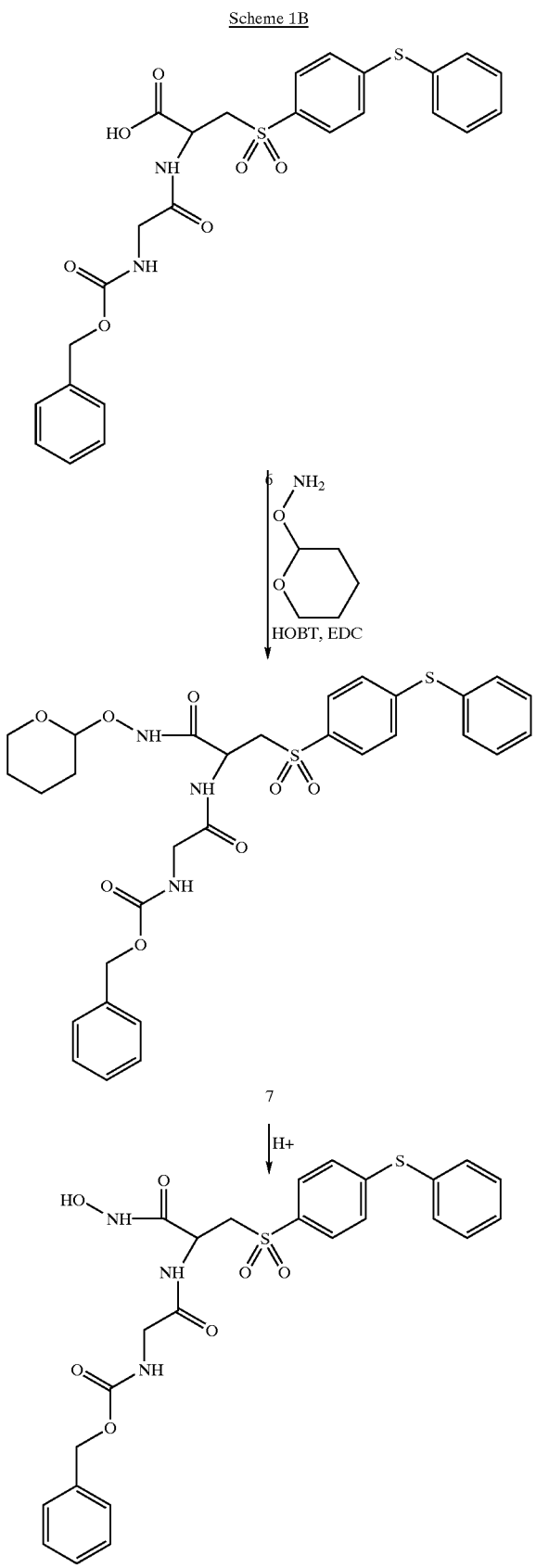

The above syntheses, as with all of the reactions discussed herein, can be carried out under a dry inert atmosphere such a nitrogen, helium or argon if desired. Selected reactions known to those skilled in the art can be carried out under a dry atmosphere such as dry air, whereas other synthetic steps, for example, aqueous acid or base ester or amide hydrolyses, can be carried out under laboratory air.

In general, the choices of starting material and reaction conditions can vary as is well known to those skilled in the art. Usually, no single set of conditions is limiting because variations can be applied as required and selected by one skilled in the art. Conditions can also be selected as desired to suit a specific purpose such as small scale preparations or large scale preparations. In either case, the use of less safe or less environmentally sound materials or reagents is usually to be minimized. Examples of such less desirable materials are diazomethane, diethyl ether, heavy metal salts, dimethyl sulfide, chloroform, benzene and the like.

Various reactions illustrated in the above Scheme can be base-mediated by the use of catalytic amounts of some bases or carried out with an equivalent or more of a base by the addition of an additional reagent or the thiol reagent can be a preformed thiol salt such as the sodium salt of a thiophenol. Bases that can be used include, for example, metal hydroxides such as sodium, potassium, lithium or magnesium hydroxide, oxides such as those of sodium, potassium, lithium, calcium or magnesium, metal carbonates such as those of sodium, potassium, lithium, calcium or magnesium, metal bicarbonates such as sodium bicarbonate or potassium bicarbonate, primary (I°), secondary (II°) or tertiary (III°) organic amines such as alkyl amines, arylalkyl amines, alkylarylalkyl amines, heterocyclic amines or heteroaryl amines, ammonium hydroxides or quaternary ammonium hydroxides.

As non-limiting examples, such amines can include triethyl amine, trimethylamine, diisopropylamine, methyldiisopropylamine, diazabicyclononane, tribenzylamine, dimethylbenzylamine, morpholine, N-methylmorpholine, N,N'-dimethylpiperazine, N-ethylpiperidine, 1,1,5,5-tetramethylpiperidine, dimethylaminopyridine, pyridine, quinoline, tetramethylethylenediamine and the like. Non-limiting examples of ammonium hydroxides, usually made from amines and water, can include ammonium hydroxide, triethylammonium hydroxide, trimethylammonium hydroxide, methyldiisopropylammonium hydroxide, tribenzyammonium hydroxide, dimethylbenzyl-ammonium hydroxide, morpholinium hydroxide, N-methylmorpholinium hydroxide, N,N'-dimethylpiperazinium hydroxide, N-ethylpiperidinium hydroxide, and the like. As non-limiting examples, quaternary ammonium hydroxides can include tetraethylammonium hydroxide, tetramethylammonium hydroxide, dimethyldiisopropylammonium hydroxide, benzylmethyldiisopropylammonium hydroxide, methyldiazabicyclononylammonium hydroxide, methyltribenzylammonium hydroxide, N,N-dimethylmorpholiniumhydroxide, N,N,N', N',-tetramethylpiperazeniumhydroxide, and N-ethyl-N'-hexylpiperidinium hydroxide and the like.

Metal hydrides, amides or alcoholates such as calcium hydride, sodium hydride, potassium hydride, lithium hydride, sodium methoxide, potassium tert-butoxide, calcium ethoxide, magnesium ethoxide, sodium amide, potassium diisopropyl amide and the like may also be suitable reagents. Organometallic deprotonating agents such as alkyl or aryl lithium reagents such as methyl, phenyl or butyl lithium, Grignard reagents such as methylmagnesium bromide or methymagnesium chloride, organocadium reagents such as dimethylcadium and the like can also serve as bases for causing salt formation or catalyzing the reaction. Quaternary ammonium hydroxides or mixed salts are also useful for aiding phase transfer couplings or serving as phase transfer reagents.

The reaction media can comprise a single solvent, mixed solvents of the same or different classes or serve as a reagent in a single or mixed solvent system. The solvents can be protic, non-protic or dipolar aprotic. Non-limiting examples of protic solvents include water, methanol (MeOH), denatured or pure 95% or absolute ethanol, isopropanol and the like. Typical non-protic solvents include acetone, tetrahydrofurane (THF), dioxane, diethylether, tert-butylmethyl ether (TBME), aromatics such as xylene, toluene, or benzene, ethyl acetate, methyl acetate, butyl acetate, trichloroethane, methylene chloride, ethylenedichloride, hexane, heptane, isooctane, cyclohexane and the like. Dipolar aprotic solvents include compounds such as dimethylformamide (DMF), dimethylacetamide (DMAc), acetonitrile, nitromethane, tetramethylurea, N-methylpyrrolidone and the like.

Non-limiting examples of reagents that can be used as solvents or as part of a mixed solvent system include organic or inorganic mono- or multi-protic acids or bases such as hydrochloric acid, phosphoric acid, sulfuric acid, acetic acid, formic acid, citric acid, succinic acid, triethylamine, morpholine, N-methylmorpholine, piperidine, pyrazine, piperazine, pyridine, potassium hydroxide, sodium hydroxide, alcohols or amines for making esters or amides or thiols for making the products of this invention and the like.

Room temperature or less or moderate warming (–10° C. to 60° C.) are the preferred temperatures of the reaction. If desired, the reaction temperature can be about –76° C. to the reflux point of the reaction solvent or solvents.

An intermediate thioether such as the 4-fluorophenylthio ether can be oxidized to the sulfone in one step using two equivalents to oxidizing agent. Reagents for this process can, in a non-limiting example, include peroxymonosulfate (OXONE®), hydrogen peroxide, meta-chloroperbenzoic acid, perbenzoic acid, peracetic acid, perlactic acid, tert-butyl peroxide, tert-butyl hydroperoxide, tert-butyl hypochlorite, sodium hypochlorite, hypochlorus acid, sodium meta-peroiodate, periodic acid and the like. Protic, non-protic, dipolar aprotic solvents, either pure or mixed, can be chosen, for example, methanol/water.

The oxidation can be carried out at temperature of about –78° to about 50° degrees centigrade, and normally is in a range of about –10° C. to about 40° C. Preparation of a desired sulfone can be carried out in a two-step process using about one quivalent of oxidizing agent to first form the sulfoxide at about 0° C. A second oxidation then produces the sulfone.

The solvents listed above can be used with these selective oxidations with, for example, methanol or methanol/water being preferred along with a temperature of from about –10° C. to 30° C. It can be desirable in the case of more active oxidizing agents, but not required, that the reactions be carried out under an inert gas atmosphere with or without degassed solvents.

A hydroxamate can be prepared from the corresponding ester by reaction of the ester with one or more equivalents of hydroxylamine hydrochloride at room temperature or above in a solvent or solvents such as those listed above. This exchange process can be further catalyzed by the addition of additional acid.

Alternatively, a base such as a salt of an alcohol used as a solvent, for example, sodium methoxide in methanol, can be used to form hydroxylamine in situ, which can exchange with an ester or amide. The exchange can be carried out with a protected hydroxylamine such as o-tetrahydro-2H-pyran-2-yl-hydroxylamine (tetrahydropyranylhydroxyamine; THPONH$_2$), benzylhydroxylamine (BnONH$_2$), and the like in which case compounds in which the ester is a tetrahydropyranyl (THP) or benzyl (Bn) ester.

Removal of the protecting groups when desired, for example, following further transformations in another part of the molecule or following storage, is accomplished by standard methods well known in the art such as acid hydrolysis of the THP group with an acid such as toluenesulfonic or hydrochloric acids or reductive removal of the benzyl group with hydrogen and a metal catalyst such as palladium, platinum, palladium on carbon or nickel.

Oxidizable functional groups are readily recognized by those skilled in the art and alternative synthesis can be used such as the protection/deprotection sequence.

Acids can be converted into activated carbonyl compounds using reagents well known in the art including the peptide and protein synthesis and amino acid coupling or conjugation art. Examples of such reagents are thionyl chloride, oxalyl chloride, phosphorus oxychloride, 1-hydroxybenzotriazole (HOBT), isobutylchloroformate an the like. These valuable activated carbonyl intermediates can then be transformed into hydroxamic acids or hydroxamic acid derivatives such as H, benzyl or THP. Preparation of or interconversion between the hydroxylamine or hydroxylamine derivative compounds or acids or amides or esters can be carried out by one skilled in the art using the methods discussed above or by other techniques.

The amine function in the intermediate compounds use a protecting group to facilitate the transformations. Decisions involving the selection of protecting groups and their use can be made by a person skilled in the art. Especially useful are the techniques and reagents used in protein, peptide and amino acid coupling and transformation chemistry.

The use of the tert-butoxycarbonyl (BOC), benzyloxycarbonyl (Z or CBZ) and N,N-dibenzyl groups as well as their synthesis and removal are examples of such protection schemes.

Coupling of the amino acids, amino acid esters, amino acid hydroxamates or hydroxamate derivatives and amino acid amides of the precursor (intermediate) compounds with, for example, other amino acids, amines, alcohols, amides or acids is also carried out by methods well known in the art such as, for example, active ester or mixed anhydride couplings with preferred bases if required being moderate tertiary amines such as N-methylmorpholine.

Removal of a preexisting group that can also serve as a protecting group or blocking group such as the acetyl group and the like is also accomplished using standard hydrolysis conditions such as base hydrolysis or exchange or acid exchange or hydrolysis.

In the case of compounds with an amine group, it is sometimes desirable to use acidic conditions with a reagent such as hydrogen peroxide and/or in combination with an acidic reagent such as periodic acid, peracetic acid and the like. It should also be noted by one skilled in the art that hydrolysis or exchange of the acetyl group may or may not effect hydrolysis or exchange of an ester, amide or hydroxamate function.

A selectively removable protecting group, P ($R^{22}$), on the hydroxamate hydroxy group can also be utilized. Such protecting groups can include acyl groups, carbamoyl groups, ethers, alkoxyalkyl ethers, cycloalkyloxy ethers, arylalkyl groups, trisubstituted silyl groups and the like. Examples of such protecting groups include acetyl, THP, benzyl, Z, tert-butyldimethylsilyl (TBDMS) groups. The preparation of such protected hydroxamates as well as the removal of the protecting groups is well known in the art and its practitioners.

Compounds of this invention can be prepared by alkylation of a carbanion (nucleophile) generated from a protected carboxylic acid using processes known in the art. Protecting groups for the carboxyl function include, for example, esters such as tert-butyl esters. Bases for forming the anion are can be organometallic reagents such as tert-butyl lithium, metal amides such as lithium diisopopyl amide (LDA) or alkoxides such as potassium tert-butoxide. Other candidate bases are discussed above.

Following or during formation of the anion, the alkylating agent (electrophile) is added which undergoes a nucleophilic substitution reaction. Electrophilic substrates for displacement can include, for example, dihalo alkanes such as 1,2-dihaloalkanes or mono-halo-mono sulfated alkanes or bissulfonate alkane esters. 1,2-di-Bromoethanes, 1-chloro-2, bromoethanes, 1-chloro-2-tosylethanes and 1,2-ditoluenesulfonylethanes are examples of such bis-electrophiles. 1-Bromo-2-chloro-ethane is a preferred electrophile.

Activated ester groups are well known in the art and can include, for example, di-easters such as malonates, ester-ketones such as acetoacetic esters or ester-aldehydes that are subject to carbonyl addition reactions. Alkylation with one equivalent of alkylating agent followed by derivatization of the new omega carbonyl group with, for example, an organometallic reagent or reduction to form an alcohol which can then be derivatized to form a carbon halogen bonds or an activated ester such as a sulfate ester. These omega-substituted compounds can serve as substrates for the thioate displacement and oxidation reactions discussed above to form the carboxylic acid compounds or intermediates of this invention.

Omega-haloalcohols can be useful starting materials for the preparation of compounds of this invention using alternative synthetic sequences from those discussed above. They can serve as substrates for $R^1$ thiolate displacement ($SN_2$) to provide 4-sulfides (thio ethers) that can then be oxidized to the desired sulfones. The HS—$R^1$ compounds can be prepared as discussed below and oxidized as discussed above. Preparation of the $R^1$ group can be via an intermediate such as a fluorothiophenol followed by displacement of the fluoride with a second nucleophile to produce compounds or intermediates of this invention. Flourothiophenol and phenol and 2,3-dimethyl phenol are examples of preferred thiols and phenols, respectively. The sulfone alcohols can be oxidized to the corresponding carboxylic acids as well as to the corresponding aldehydes.

The preparation of ethers can be carried out by forming a salt of the alcohol and treating this nucleophile with an electrophile such as a halide or an activated ester such as a sulfate ester. The salt is formed by treating the alcohol with a base such as is discussed above. Examples of such bases are lithium alkyls, metal hydrides or the metal salts of an amine such as LDA.

Halides can be chlorides, bromides or iodides and sulfates can be, for example, benzene sulfonates, tosylates, mesylates or triflates. An example of a preferred electrophile is 2-chloromethylpyridine and a preferred base is sodium hydride. Alternatively, the alcohol can be converted into a leaving group (electrophilic reagent) and then treated with a nucleophile. Examples of such leaving groups include sulfate esters such tosylates, mesylates and triflates whose preparation is discussed above. The triflate is a preferred leaving group.

Displacement of these groups with nucleophiles is well known in the art and discussed and/or illustrated above. The nucleophiles can be hydroxide to allow inversion of stereochemistry, alkoxides to form ethers, amines or ammonia to form substituted amines or an azide anion to form an azide. A preferred nucleophile the is tetra-(n-butyl) ammonium azide. The azido compound, for example, can be reduced to form the amino acid.

Reductions are discussed above and are well known in the art. A preferred method is hydrogenation with palladium on carbon catalyst.

The amines, including the amino acids, of this invention can be acylated or alkylated by methods well known in the art. The amides formed can be considered as protected amines or as end products of this invention. Acylation to form such derivatives as tert-butoxycarbonyl and carbobenzyloxy carbonyl group is discussed above. Other acyl (Ac) groups can be, for example, acetyl, haloacetyl, aroyl, substituted aroyl, heteroaroyl, substituted heteroaroyl or other groups as required. The amines can be acylated using anhydrides, mixed anhydrides, acid chlorides or activated esters. Usually such acylations are carried out in presence of a base such as the bases discussed above and well known in the art. Examples are N-methyl-morpholine, triethylamine and the like.

The carboxyl compounds useful herein having amide substituents can be treated, converted or interconverted as shown and/or discussed above to form the products of this invention. In addition, the haloacetyl compounds such as the preferred 2-chloroacetamide derivative can be treated with an amine as a nucleophile to yield an amino acid. Again, these reactions are well known in the art. A preferred amine is morpholine.

Alkylation of the amino acid at the carbon alpha to the carbonyl group to form a useful compound can be carried out by first forming an anion using a base. Exemplary bases are discussed elsewhere. The preferred bases are strong bases that are either hindered and/or non-nucleophilic such as lithium amides, metal hydrides or lithium alkyls. A preferred base is lithium diisopropylamide (LDA) in a dipolar aprotic solvent or THF.

Following or during formation of the anion, an alkylating agent (an electrophile) is added which undergoes a nucleophilic substitution reaction. Non-limiting examples of such alkylating agents are 1,2-dihaloalkanes or haloalkanes also substituted by an activated ester group. Activated ester groups are well known in the art and can include, for example, an ester of a 2-halo-alcohol such a bromo-, iodo- or chloro-ethane para-toluene sulfonate, triflate or mesylate. A preferred alkylating agents is 1-bromo-2-chloroethane.

The nitrogen substituent on the amino acid portion of the compounds of this invention can be varied. In addition, this can be accomplished at different stages in the synthetic sequence based on the needs and objectives of the skilled person preparing the compounds of this invention.

The N-side chain variations can include replacing the hydrogen (hydrido) substituent with a alkyl, arylalkyl, alkene or alkyne. This can be accomplished by methods well known in the art such as alkylation of the amine with an electrophile such as halo- or sulfate ester (activated ester) derivative of the desired side chain. This can be done in the presence of a base such as those discussed above and in a pure or mixed solvent as discussed above. A preferred base is potassium carbonate and a preferred solvent is DMF.

The alkenes and alkynes can be reduced, if desired, by, for example, hydrogenation with a metal catalyst and hydrogen, to an alkyl or arylalkyl compound of this invention and the alkyne or arylalkyne can be reduced to a alkene of alkane with under catalytic hydrogenation conditions as discussed above or with an deactivated metal catalyst. Catalysts can include, for example, Pd, Pd on Carbon, Pt, $PtO_2$ and the like. Less robust catalysts include such thing as Pd on $BaCO_3$ or Pd with quinoline or/and sulfur.

An alternative method for alkylation of the amine nitrogen is reductive alkylation. This process, well known in the art, allows treatment of the secondary amine with an aldehyde or ketone in the presence of a reducing agent such as borane, borane:THF, borane:pyridine, lithium aluminum hydride. Alternatively, reductive alkylation can be carried out hydrogenation conditions in the presence of a metal catalyst. Catalysts, hydrogen pressures and temperatures are discussed above and are well known in the art. A preferred reductive alkylation catalyst is borane:pyridine complex.

The compounds of this invention include compounds wherein the substituent on nitrogen of the amino acids as listed above provide amino acid carbamates. Non-limiting examples of these carbamates are the carbobenzoxycarbonyl (Z, CBZ, benzyloxycarbonyl), isobytoxycarbonyl and tert-butoxycarbonyl (BOC, t-BOC) compounds. These materials can be made, as discussed above, at various stages in the synthesis based on the needs and decisions made by a person skilled in the art using methods well known in the art.

Useful synthetic techniques and reagents include those used in protein, peptide and amino acid synthesis, coupling and transformation chemistry. The use of the tert-butoxycarbonyl (BOC) and benzyloxycarbonyl (Z) as will as their synthesis and removal are examples of such protection or synthesis schemes discussed above. Transformations of amino acids, amino esters, amino acid hydroxamates, amino acid hydroxamate derivatives and amino acid amides of this invention or compounds used in this invention can be carried out as discussed and/or illustrated above. This includes, for example, active ester or mixed anhydride couplings wherein preferred bases, if required, are tertiary amines such as N-methylmorpholine.

Reagents for protection of the amine group of the protected amino acids include carbobenzoxy chloride, isobutylchloroformate, tert-butoxycarbonyl chloride, di-tert-butyl dicarbonate and the like which are reacted with the amine in non-protic or dipolar aprotic solvents such as DMF or THF or mixtures of solvents. A preferred reagent is di-tert-butyl dicarbonate and a preferred solvent is THF. Further conversion of the cyclic amino acids of this invention including alkylation, displacement with a thiol or thiolate, oxidation to a sulfone, and conversion into a hydroxamic acid or hydroxamate derivative can be carried out discussed herein.

Sulfone compounds such as those where $R^1$ is nitroaryl can be prepared as compounds of this invention by synthesis of a thiol or thiolate nucleophile, displacement of an electrophile (X) by the nucleophilic thiol or thiolate and oxidation of the product thia ether (sulfide) to the sulfone. For example, displacement of the electrophilic group X with a nitro-benzenethiol can yield a compound where $R^1$ is nitrobenzene that can be reduced to provide a useful amino compound wherein $R^1$ is an aniline that can be acylated to form a benzamido compound such as compounds 61–64 of Table 8, for example. It should be noted that nitrobenzenethiol is an example and not to be considered as limiting or required. Oxidation of the thioether product can be carried out as discussed below when desired.

The reduction of nitro groups to amines is well known in the art with a preferred method being hydrogenation. There is usually a metal catalyst such as Rh, Pd, Pt, Ni or the like with or without an additional support such as carbon, barium carbonate and the like. Solvents can be protic or non-protic pure solvents or mixed solvents as required. The reductions can be carried out at atmospheric pressure to a pressure of multiple atmospheres with atmospheric pressure to about 40 pounds per square inch (psi) preferred. The amino group can be alkylated if desired, or acylated with, for example, an aroyl chloride, heteroaryl chloride or other amine carbonyl forming agent to form an $R^1$ amide.

The amino sulfone or thioether can also be reacted with a carbonic acid ester chloride, a sulfonyl chloride, a carbamoyl chloride or an isocyanate to produce the corresponding carbamate, sulfonamides, or urea. Acylation of amines of this type are well known in the art and the reagents are also well known.

Usually, these reactions are carried out in aprotic solvents under an inert or/and dry atmosphere at about 45° C. to about –10° C. An equivalent of a non-competitive base is usually used with sulfonyl chloride, acid chloride or carbonyl chloride reagents. Following or before this acylation step, synthesis of the hydroxamic acid products of this invention can proceed as discussed.

Other thiol reagents can also be used in the preparation of compounds of this invention. Examples are fluoroaryl, fluoroheteroaryl, azidoaryl or azidoheteroaryl or heteroaryl thiol reagents. These thiols can be used a nucleophiles to as discussed above. Oxidation to the corresponding sulfone can then be carried out. The fluoro-substituted sulfone can be treated with a nucleophile such as ammonia, a primary amine, a quaternary ammonium or metal azide salt, under pressure if desired, to provide an azido, amino or substituted amino group that can then be reacted an activated benzoic or substituted benzoic acid derivative to form a benzamide. Azides can be reduced to an amino group using, for example, hydrogen with a metal catalyst or metal chelate catalyst or by an activated hydride transfer reagent. Hydrazo compounds can be oxidized to azo compounds and axo compounds can be reduced to hydrazo compounds. The amines can be acylated as discussed above.

Preferred methods of preparing aminethiol intermediates of this invention include protection of an aromatic or heteroaromatic thiol with trityl chloride to form the trityl thiol derivative, treatment of the amine with as reagent such as an aromatic or heteraromatic acid chloride to form the amide, removal of the trityl group, with acid to form the thiol. Preferred acylating agents include benzoyl chloride and preferred trityl removing reagents include triflouroacetic acid and trisiopropylsilane.

The fluorine on fluorosulfone intermediates can also be displaced with other aryl or heteroaryl nucleophiles for form compounds of this invention. Examples of such nucleophiles include salts of phenols, thiophenols, —OH group containing aromatic heterocyclic compounds or —SH containing heteroaryl compounds.

Tautomers of such groups azo, hydrazo, —OH or —SH are specifically included as useful isomers.

A preferred method of preparing intermediates in the synthesis of the substituted sulfones is by oxidation of an appropriate acetophenone, prepared from a flouroacetophenone, with for example, peroxymonosulfate, to form the corresponding phenol-ether. That phenol-ether is converted into its dimethylthiocarbamoyl derivative using dimethylthiocarbamoyl chloride, followed by rearranging the dimethylthiocarbamoyl derivative with heat to provide the thiol required for preparation of the thioether intermediate.

Salts of the compounds or intermediates of this invention are prepared in the normal fashion wherein acidic compounds are reacted with bases such as those discussed above to produce metal or nitrogen containing cation salts. Basic compounds such as amines can be treated with an acid to for form the amine salt. A preferred amine salt is the hydrochloride salt formed by reaction of the free base with HCl or hydrochloric acid.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes well known in the art, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers.

Still another available method involves synthesis of covalent diastereoisomeric molecules, e.g., esters, amides, acetals, ketals, and the like, by reacting compounds of Formula I with an optically active acid in an activated form, a optically active diol or an optically active isocyanate. The synthesized diastereoisomers can be separated by conventional means such as chromatography, distillation, crystallization or sublimation, and then hydrolyzed to deliver the enantiomericaly pure compound. In some cases hydrolysis to the parent optically active drug is not necessary prior to dosing the patient because the compound can behave as a prodrug. The optically active compounds of Formula I can likewise be obtained by utilizing optically active starting materials.

In addition to the optical isomers or potentially optical isomers discussed above, other types of isomers are specifically intended to be included in this discussion and in this invention.

Examples include cis isomers, trans isomers, E isomers, Z isomers, syn-isomers, anti-isomers, tautomers and the like. Aryl, heterocyclo or heteroaryl tautomers, heteroatom isomers and ortho, meta or para substitution isomers are also included as isomers. Solvates or solvent addition compounds such as hydrates or alcoholates are also specifically included both as chemicals of this invention and in, for example, formulations or pharmaceutical compositions for delivery.

BEST MODE FOR CARRYING OUT THE INVENTION

Without further elaboration, it is believed that one skilled in the art can, using the preceding description, utilize the present invention to its fullest extent. The following preferred specific embodiments are, therefore, to be construed as merely illustrative, and not limiting of the remainder of the disclosure in any way whatsoever.

Abbreviations are often used for reagents and solvents in the specific examples that follow. Those abbreviations and their meanings are as follows:

BOC=t-butoxycarbonyl
DEAD=diethyl azodicarboxylate
DMF=dimethylformamide
DMPU=1,3-dimethyl-3,4,5,6-tetrahydro-2(1H)-pyrimidinone
EtOAc=ethyl acetate
EDC=1-ethyl-3-[3-(dimethylamino)propyl]carbodiimide hydrochloride
Et$_2$O=diethyl ether
HOBT=1-hydroxybenzotriazole
MeOH=methanol
MeCl$_2$=methylene chloride
MsCl=methanesulfonyl chloride
NMMOL or NMM=N-methyl morpholine
THF=tetrahydrofruan
TsCl=toluenesulfonyl chloride
THP-O-hydroxylamine=O-tetrahydropyranhydroxylamine and O-tetrahydro-2H-pyran-2-yl-hydroxylamine
Z=carbobenzyloxycarbonyl

EXAMPLE 1

Preparation of N-Hydroxy-3-[(4-methoxyphenyl)sulfonyl]-2-[(methylcarbonyl)amino]propanamide

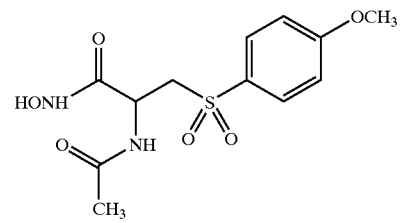

Part A: A 250 mL round bottom flask equipped with magnetic stir bar and N$_2$ inlet was charged with 10.0 g N-acetyl dehydroalanine methyl ester, 9.9 g p-methoxythiophenol, and 10 mL NEt$_3$ in 100 mL of degassed MeOH. The reaction mixture was stirred one hour then concentrated in vacuo to remove NEt$_3$. The crude residue was taken up in 200 mL MeOH-150 mL H$_2$O and treated with 89 g (2.0 eq) Oxone®. The reaction was stirred 1 hour, filtered and the filtrate was concentrated in vacua. Partionning between EtOAc-water was followed by washing with water, brine, and concentration in vacuo. The crude off white solid was triturated with Et$_2$O to yield 14 g pure ester sulfone.

Part B: A 100 mL round bottom flask equipped with magnetic stir bar and N$_2$ inlet was charged with 500 mg ester sulfone, 1.2 mL (2.0 eq.) 50% aqueous hydroxylamine in 8 mL MeOH/8 mL THF. The reaction was stirred overnight (about 18 hours) then concentrated in vacuo to a solid. Trituration with EtOAc yielded 380 mg of the desired hydroxamate.

EXAMPLE 2

Preparation of 2-[[[(1,1-Dimethylethyl)amino]carbonyl]amino]-N-hydroxy-3-[(4-methoxyphenyl)sulfonyl]propanamide

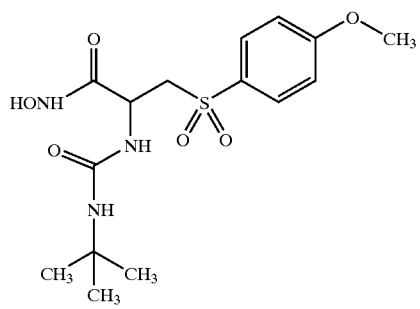

Part A: A 250 mL round bottom flask equipped with magnetic stir bar and $N_2$ inlet was charged with 7.4 product from Example 1, Part A in 50 mL acetic acid and 50 mL concentrated HCl. The reaction was heated at reflux for 4 hours. The reaction mixture was concentrated in vacuo to a off white solid that was chased 2x with toluene, then vacuum dried to yield 6.55 g of the amino acid HCl salt.

Part B: A 250 mL round bottom flask equipped with magnetic stir bar and $N_2$ inlet was charged with 6.5 g of the product amino acid HCl salt from above and 2.5 mL (1.5 eq.) of $SOCl_2$ in 70 mL MeOH. The reaction was heated at reflux for 3 hours, then concentrated in vacuo to a crude solid. Trituration with $EtO_2$ yielded 6.9 g of amino ester HCl salt. The free base was generated using EtOAc-aqueous bicarbonate and was used without further purification.

Part C: A 100 mL round bottom flask equipped with magnetic stir bar and $N_2$ inlet was charged with 900 mg of the amino ester from above and 288 mg t-butyl isocyanate in 20 mL $MeCl_2$. The reaction was stirred overnight (about 18 hours), then concentrated in vacuo. Partitioning between hot EtOAc-water followed by washing with water, brine, and concentration in vacuo yielded 850 mg pure ester urea.

Part D: A 100 mL round bottom flask equipped with magnetic stir bar and $N_2$ inlet was charged with 90 mg ester urea from above and 0.2 mL (12.0 eq) 50% aqueous hydroxylamine in 2 mL MeOH/2 mL THF. The reaction was stirred overnight (about 18 hours), then concentrated in vacuo to a solid. Trituration with $Et_2O$ and filtration gave 50 mg of pure hydroxamate.

EXAMPLE 3

Preparation of N-Hydroxy-3-[(4-methoxyphenyl)sulfonyl]-2-[(phenylcarbonyl)amino]propanamide

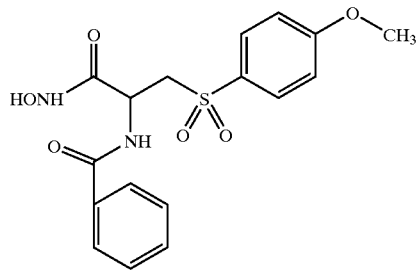

Part A: A 500 mL round bottom flask equipped with magnetic stir bar and $N_2$ inlet was charged with 5.0 g (15.9 mmol) of ester from Example 1, Part A, in 50 mL acetic acid and 50 mL concentrated HCl. The reaction was heated at reflux for 4 hours. The reaction mixture was concentrated in vacuo to a white solid, then added and stripped with two aliquots of water and then two aliquots of toluene, then vacuum dried to yield 4.6 g of pure amino acid HCl salt, m/z=260 (M+H), as the HCl salt.m/z=260.

Part B: A 500 mL round bottom flask equipped with magnetic stir bar and $N_2$ inlet was charged with 4.6 g (15.7 mmol) amino acid HCl salt product from Part A in 100 mL MeOH. The solution was cooled in an ice bath, then treated with 1.7 mL (2.8 g, 23.5 mmol) thionyl chloride. The reaction was heated at reflux for 3 hours, then concentrated in vacuo. The residue was partitioned between EtOAc and saturated sodium bicarbonate solution, the layers separated, and the aqueous layer was extracted with EtOAc (1x). The organic layers were combined and washed with brine, dried ($MgSO_4$), and concentrated in vacuo to yield 2.9 grams of product suitable for the next reaction.

Part C: A 100 mL round bottom flask equipped with magnetic stir bar and $N_2$ inlet was charged with 0.7 g (2.7 mmol) product from Part B and 0.6 mL (0.4 g, 4.0 mmol) triethylamine in 10 mL $CH_2Cl_2$. The solution was cooled in an ice bath and treated with 0.4 mL (0.5 g, 3.2 mmol) benzoyl chloride. After stirring for 1 hour, the reaction was concentrated in vacuo, the residue was partitioned EtOAc and water, and the aqueous layer was extracted with EtOAc (1x). The organic layers were combined, washed with 5% citric acid solution, saturated bicarbonate solution and brine, dried ($Na_2SO_4$), and concentrated in vacuo to yield 0.8 g of crude amide product. The crude amide product was chromatographed on silica gel using 50% ethyl acetate/hexane to yield 0.6 g of pure amide, m/z=378 (M+H).

Part D: A 250 mL round bottom flask equipped with magnetic stir bar and $N_2$ inlet was charged with 0.6 g (1.6 mmol) of pure amide from Part C in THF (20 mL). The solution was treated with 0.5 mL (0.5 g, 8.21 mmol) 50% aqueous hydroxylamine. After stirring for 65 hours, the reaction was not complete, and 0.1 g (4.3 mmol) of sodium metal and 5 mL MeOH were added to the reaction to drive it to completion. The reaction was quenched with dry ice and then concentrated in vacuo. The residual solids were partitioned between EtOAc/2 N HCl solution. The solid precipitate was isolated by filtration, washed with water and EtOAc, then dried to yield 0.3 g of pure hydroxamate, m/z=379 (M+H).

EXAMPLE 4

Preparation of N-Hydroxy-3-[(4-methoxyphenyl)sulfonyl]-2-[(butylcarbonyl)amino]propanamide

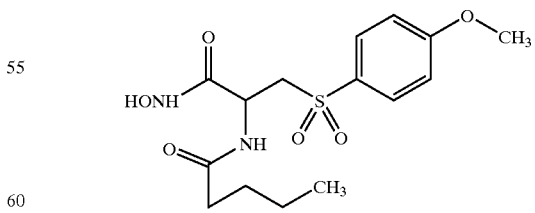

Part A: A 500 mL round bottom flask equipped with magnetic stir bar and $N_2$ inlet was charged with 5.0 g (15.9 mmol) product from Example 1, Part A, in 50 mL acetic acid and 50 mL concentrated HCl. The reaction was heated at reflux for 4 hours. The reaction mixture was concentrated in vacuo to a white solid, and was then stripped with two aliquots of water and then two aliquots of toluene, then vacuum dried to yield 4.6 g of pure amino acid, m/z=260 (M+H), as the HCl salt.m/z=260.

Part B: A 250 mL round bottom flask equipped with magnetic stir bar and $N_2$ inlet was charged with 6.5 g product the amino acid from above and 2.5 mL (1.5 eq.) of $SOCl_2$ in 70 mL MeOH. The reaction was heated at reflux for 3 hours then concentrated in vacuo to provide a crude solid. Trituration with $EtO_2$ yielded 6.9 g of amino ester HCl salt suitable for the next reaction.

Part C: A 100 mL round bottom flask equipped with magnetic stir bar and $N_2$ inlet was charged with 1.0 g (3.2 mmol) of amino ester HCl salt product from Part B and 1.4 mL (1.0 g, 9.7 mmol) triethylamine in 10 mL $CH_2Cl_2$. The reaction slurry was cooled in an ice bath and treated with 0.5 mL (0.5 g, 3.9 mmol) valeryl chloride. After stirring for 1 hour, the reaction was incomplete, and an additional 0.5 mL triethylamine and 0.4 mL valeryl chloride were added. The reaction was stirred for 2 more hours, then concentrated in vacuo. The residue was partitioned EtOAc and water, and the aqueous layer was extracted with EtOAc (1x). The organic layers were combined, washed with 5% citric acid solution, saturated bicarbonate solution and brine, dried ($Na_2SO_4$), and concentrated in vacuo to yield 1.3 g of crude product. The crude product was slurried with diethyl ether, filtered and dried to yield 0.8 g of pure amide, m/z=358 (M+H).

Part D: A 100 mL round bottom flask equipped with magnetic stir bar and $N_2$ inlet was charged with 0.8 g (2.3 mmol) of pure amide from Part C in THF (20 mL) and MeOH (10 mL). The solution was treated with 2.5 mL (1.4 g, 46.4 mmol) 50% aqueous hydroxylamine. After stirring for 16 hours, the reaction mixture was concentrated in vacuo, the residue was partitioned between EtOAc/water, the layers were separated, and the organic layer was washed with brine, dried ($Na_2SO_4$), and concentrated in vacuo to yield a white solid. The solid was slurried with diethyl ether, isolated by filtration, then dried to yield 0.6 g of pure hydroxamate, m/z=359 (M+H).

EXAMPLE 5

Preparation of N-Hydroxy-3-[(4-bromophenyl)sulfonyl]-2-[(methylcarbonyl)amino]propanamide

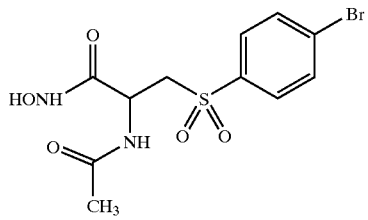

Part A: A 1000 mL round bottom flask equipped with magnetic stir bar and $N_2$ inlet was charged with 25.0 g (132.2 mmol) 4-bromothiophenol and 19.9 g (138.8 mmol) methyl acetamidoacrylate in 400 mL degassed MeOH. The solution was cooled in an ice bath and treated with 19.4 mL (14.0 g, 138.8 mmol) triethylamine. The reaction was stirred for 1 hour and a white solid precipitated. The solid was isolated by filtration, washed with MeOH and dried to yield 27.6 g of product suitable for the next reaction.

Part B: A 1000 mL round bottom flask equipped with magnetic stir bar and $N_2$ inlet was charged with 11.0 g (33.1 mmol) of product from Part A in 400 mL MeOH. The slurry was warmed to yield a solution, then treated with 40 mL water and 61.1 g (99.3 mmol) Oxone®. The reaction mixture was stirred 4 hours, then filtered. The filter cake was washed with MeOH, and the filtrate was concentrated in vacuo. The residue was partitioned between EtOAc and $H_2O$, the layers were separated and the aqueous layer was extracted with EtOAc (2x). The organic phases were combined, washed with saturated sodium bicarbonate solution and brine, dried ($MgSO_4$), and concentrated in vacuo to yield the 6.7 g of pure product, m/z=370 (M+Li).

Part C: A 100 mL round bottom flask equipped with magnetic stir bar and $N_2$ inlet was charged with 0.7 g (1.9 mmol) solid from Part B in THF (5 mL) and MeOH (5 mL). The solution was treated with 2.1 mL (1.2 g, 38.4 mmol) 50% aqueous hydroxylamine. After stirring for 17 hours, the reaction was concentrated in vacuo, the residue was partitioned between EtOAc/water, giving a three-phase system—the organic, aqueous and a solid precipitate at the interface. The solid was isolated by filtration, washed with diethyl ether, isolated by filtration, then dried to yield 0.2 g of pure hydroxamate, m/z=387 (M+Na).

EXAMPLE 6

Preparation of Phenylmethyl-[2-[[2-(hydroxyamino)-2-oxo-1-[[[4-methoxyphenyl]sulfonyl]methyl]ethyl]amino]-2-oxoethyl]carbamate

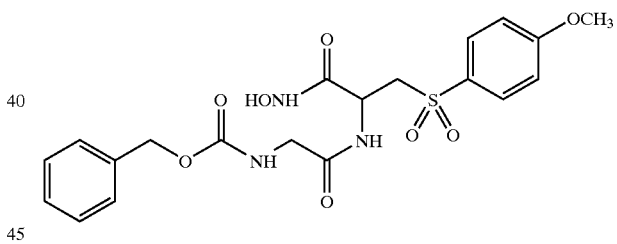

Part A: A 100 mL round bottom flask equipped with magnetic stir bar and $N_2$ inlet was charged with 1.0 g Z-Gly-OH, 920 mg (1.0 eq) EDC, 960 mg (1.5 eq) HOBT in 8 mL dry DMF. The reaction was activated for 10 minutes and then treated with 1.0 g free amino ester from Example 2, Part B. After stirring for 17 hours, the reaction was partitioned between EtOAc/saturated sodium bicarbonate. The combined organic phases were washed with 10% $KHSO_4$, water, brine, and concentrated in vacuo to yield 1.25 grams of amide ester (>95% by HPLC).

Part B: A 100 mL round bottom flask equipped with magnetic stir bar and $N_2$ inlet was charged with 700 mg of amide ester, 2.0 mL 50% aq. hydroxylamine in 5 mL THF. The reaction was stirred 2 hours then quenched with dry ice. Standard work-up following evaporation from $MeCl_2$ gave the desired hydoxamate as a dry foam (>97% by HPLC).

EXAMPLE 7

Preparation of 4-[[1-[(Hydroxyamino)carbonyl]-2-[(4-methoxyphenyl)sulfonyl]-ethyl]amino-4-oxobutanoic Acid Benzyl Ester

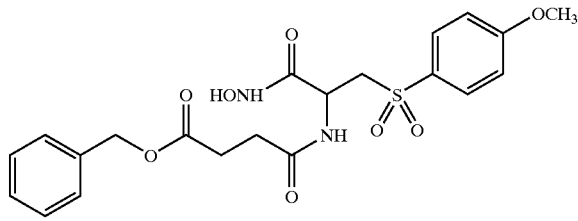

Part A: A reaction mixture was prepared containing 2.36 g mono benzyl succinic acid (1.15 eq.), 2.18 g (1.15 eq.) EDC, and 2.0 g (1.5 eq.) HOBT in 8 mL dry of DMF. The reaction was activated for 10 minutes and then treated with 2.7 g free amino ester from Example 2, Part B. After stirring for 17 hours, the reaction was partitioned between EtOAc/saturated sodium bicarbonate. The combined organic phases were washed with 10% $KHSO_4$, water, brine, and concentrated in vacuo to yield 3.8 g of crude amide (82% by HPLC). Flash chromatography with EtOAc yielded 3.1 g of pure diester product.

Part B: A 100 mL round bottom flask equipped with magnetic stir bar and $N_2$ inlet was charged with 436 mg of pure diester, and 1.3 mL 50% aq. hydroxylamine in 20 mL MeOH and 5 mL THF. The reaction was stirred overnight (about 18 hours) then concentrated to provide a crude product (35% by HPLC). Partitioning between EtOAc/water gave 200 mg crude product (75% by HPLC). Flash chromatography with 100% THF gave 100 mg of pure hydroxamate.

EXAMPLE 8

Preparation of 4[[1-[(Hydroxyamino)carbonyl]-2-[(4-methoxyphenyl)sulfonyl]-ethyl]amino-4-oxobutanoic Acid

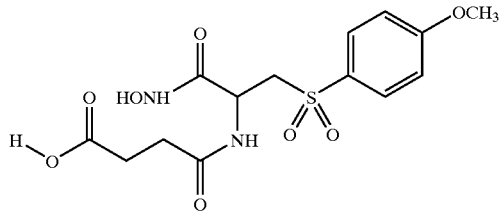

Part A: A 300 mL Paar flask equipped with magnetic stir bar was charged with 436 mg of diester from Example 7, Part A, 100 mg 10% Pd—C, in 35 mL MeOH, 30 mL AcOH then 60 mL THF. The reaction mixture was hydrogenated at 50 psi overnight (about 18 hours). After a $N_2$ purge the reaction was filtered through Celite® and concentrated to crude oil. The product was chased 2× with toluene then triturated with $Et_2O$ to yield 630 mg (78%) of the ester as a white solid.

Part B: A 100 mL round bottom flask equipped with magnetic stir bar and $N_2$ inlet was charged with 373 mg of the ester of Part A, and 1.0 mL 50% aq. hydroxylamine in 4 mL MeOH and 5 mL THF. The reaction was stirred overnight (about 18 hours), concentrated to a crude off white solid that was chased 2× with toluene then triturated with $Et_2O$ to yield 250 mg of the title hydroxamate.

EXAMPLE 9a

Preparation of O-(4-Phenoxyphenyl)-N,N-dimethylcarbamothioate

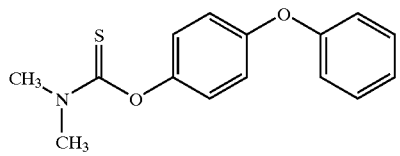

According to the general procedure described by Newman [*Org. Syn.*, 51, 139–142], 4-phenoxyphenol (150 mmol, 27.9 g) was added to an zero degrees C. solution of potassium hydroxide (150 mmol, 8.4 g) in water (100 mL) under an argon atmosphere. After dissolution of the phenol, dimethylthiocarbamoyl chloride (150 mmol, 24.8 g) in tetrahydrofuran (THF; 40 mL) was introduced to the reaction vessel at such a rate the internal temperature of the flask did not exceed 12° C. (over a period of about 20 minutes). After complete addition, the cooling bath was removed, and stirring was continued an additional 10 minutes. Aqueous KOH (10%, 50 mL) was added, and the reaction mixture was extracted with toluene (3×100 mL). The combined organic layers were dried over magnesium sulfate, filtered through a short plug of silica, concentrated, seeded with a previous sample, and stored at zero degrees C. The resulting solid was triturated with methylene chloride (10 mL), affording 25.9 g of the title compound as a solid (63%). DSC 1 degree C./minute: 52.5–56.2° C.

EXAMPLE 9b

Preparation of S-(4-Phenoxyphenyl)-N,N-dimethylcarbamothioate

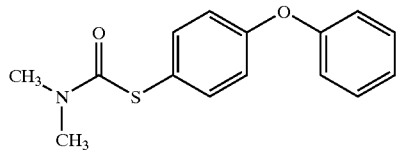

The product from Example 9a (25.91 g) was heated under an argon atmosphere to 32 degrees C. (internal) and maintained at that temperature for 15 minutes. The dark oil was allowed to cool, was characterized spectroscopically, and was used directly in the next step.

EXAMPLE 9c

Preparation of 4-(Phenoxy)benzenethiol

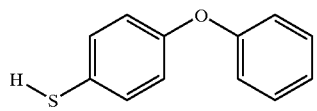

Ethylene glycol (75 mL), water (10 mL) and potassium hydroxide (9 g) were added to the above-produced dark oil, and the mixture was heated at reflux for 1 hour. Upon cooling, the mixture was poured over ice (about 200 mL), and washed with chloroform (2×150 mL). The aqueous layer was acidified with concentrated HCl, and the product was extracted into chloroform (3×75 mL). The organic layers were collected, dried (MgSO$_4$), filtered through a short silica plug, and concentrated to afford the title compound as an oil (9.5 g, 49% from Example 9b)

EXAMPLE 9d

Preparation of N-Acetyl-3-[(4-phenoxyphenyl) sulphonyl]alanine, Methyl Ester

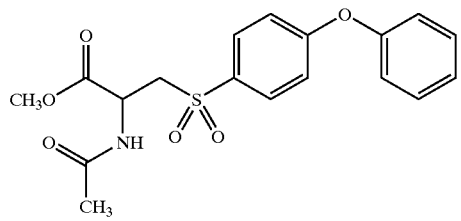

The product from Example 9c (15 mmol, 3.03 g) was diluted with methanol. Methyl 2-(acetylamino)-2-propenoate (15 mmol, 2.14 g) was added, followed by triethylamine (15 mmol, 2.1 mL). The solution was stirred for one hour at ambient temperature, and for 2 hours at 45–5 zero degrees C. The crude reaction mixture was rinsed into larger flask with a total of 50 mL additional methanol and cooled to zero degrees C. A solution of Oxone® (30 mmol, 18.45 g) in water (100 mL) was added. After 5 minutes, the cooling bath was removed. The mixture was stirred at ambient temperature for one hour, then diluted with additional water (200 mL), and extracted with chloroform (200 mL, then 2×50 mL). The combined organic layers were dried (magnesium sulfate), filtered, concentrated, and subjected to chromatography (hexane:ethyl acetate 1:1), affording the title compound as a white solid (2.185 g, 39%). DSC 1 degrees C./minute: 127.0–129.8. The product was characterized spectroscopically. Elemental Anal. Calcd. for $C_{18}H_{19}NO_6S$: C, 57.28; H, 5.07; N, 3.71. Found: C, 57.10; H, 4.94; N, 3.51.

EXAMPLE 9e

Preparation of N-Acetyl-3-[(4-phenoxyphenyl) sulphonyl]alanine

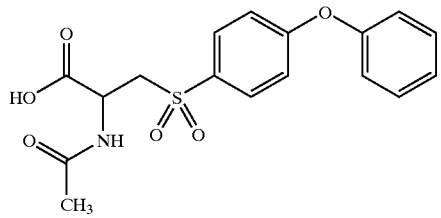

The product from Example 9d (2.1 mmol, 800 mg) was diluted with acetic acid (2 mL) and concentrated hydrochloric acid (2 mL) and warmed to 7zero degrees C. for one hour. The reaction mixture was concentrated, and azeotroped with toluene (3×5 mL), affording the title compound as a solid (quant.). MS MH+ calcd. for $C_{17}H_{17}NO_6S$ 364, found 364. DSC 1 degree C./minute: 193.0–195.1. The product was characterized spectroscopically.

EXAMPLE 9f

Preparation of $N^2$-Acetyl-3-[(4-phenoxyphenyl) sulphonyl]-$N^1$-(3,4,5,6-tetrahydro-2H-pyran-2-yl) alaninamide

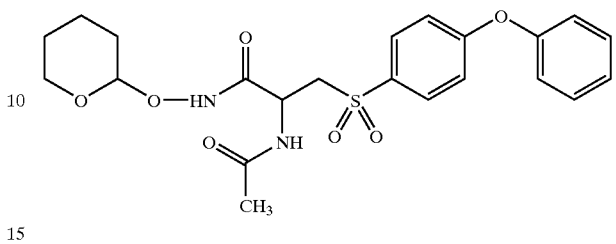

The acid from Example 9e (2.1 mmol) was combined with hydroxybenzotriazole (2.7 mmol, 365 mg), O-tetrahydropyranhydroxylamine (3 mmol, 0.35 g), N,N-dimethylformamide (4 mL) and N-methylmorpholine (13 mmol, 1.43 mL). EDC (2.7 mmol, 518 mg) was added and the mixture was stirred at ambient temperature overnight (about 18 hours). The mixture was diluted with saturated NaHCO$_3$ (20 mL) and extracted with ethyl acetate (100 mL). The organic phase was washed with brine (20 mL), then dried over magnesium sulfate, filtered, concentrated, and subjected to silica gel chromatography (6% methanol in chloroform), affording the title compound as a glass (472 mg, 50%). The product was characterized spectroscopically.

EXAMPLE 9g

Preparation of $N^2$-Acetyl-$N^1$-hydroxyl-3-[(4-phenoxyphenyl)sulphonyl]alaninamide

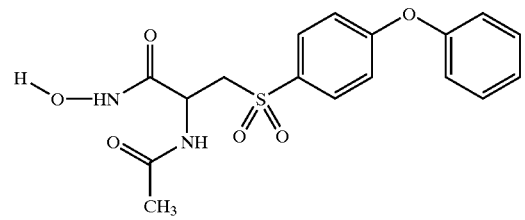

The product from Example 9f (1.0 mmol, 450 mg) was dissolved in dioxane (5 mL). Six normal HCl (0.5 mL) was added, and the mixture was stirred one hour. Concentration followed by chromatography afforded the title compound as a glass (120 mg, 32%). MS MH+ calcd. for $C_{17}H_{18}N2O_6S$ 378, found 379.

EXAMPLE 10a

Preparation of 3-[(4-Phenoxyphenyl)sulphonyl] alanine, Monhydrochloride

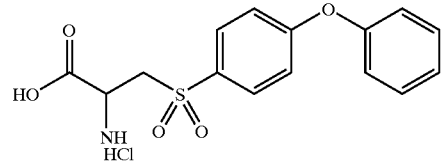

A solution of the titled compound of Example 9d (3.27 g, 8.66 mmol) in glacial acetic acid (18.5 mL) was heated until all solids dissolved and then concentrated HCl (18.5 mL) was added. The solution was heated at reflux for 4 hours. The mixture was concentrated to an off white solid. The solid was treated with toluene, concentrated, and triturated with diethyl ether afforded the title amino acid as a white solid (3.04 g, 98%). Elemental Anal. Calcd. for $C_{15}H_{16}NO_5SCl$: C, 50.35; H, 4.51; N, 3.91; S, 8.96. Found: C, 50.21; H, 4.43; N, 3.92; S, 9.04.

EXAMPLE 10b

Preparation of N-[(1,1-Dimethylethyl)carbonyl]-3-[(4-phenoxyphenyl)alaninamide

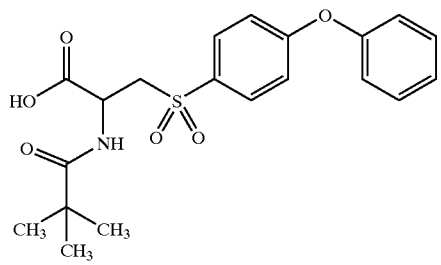

The amino acid (1.4 mmol, 500 mg) from above was dissolved in a mixture of water (2 mL), triethylamine (5.6 mmol, 0.79 mL), and acetone (3 mL), and cooled to zero degrees C. Pivaloyl chloride (1.8 mmol, 0.22 mL) was added over 5 minutes. The reaction was warmed to ambient over one hour and stirred overnight (about 18 hours), then concentrated and azeotroped with acetonitrile (10 mL). Chromatography (20% methanol/chloroform) afforded the title compound as the triethylamine salt. The triethylamine salt was dissolved in chloroform (150 mL) and washed with 2N HCL (20 mL). The organic layer was dried over magnesium sulfate, filtered, concentrated and rechromatographed to afford the title compound as a white foam (485 mg). The product was characterized spectroscopically.

EXAMPLE 10c

Preparation of $N^2$-(1,1-Dimethylethyl)-3-[(4-phenoxyphenyl)sulphonyl]-$N^1$-3,4,5,6-tetrahydro-2H-pyran-2-yl)alaninamide

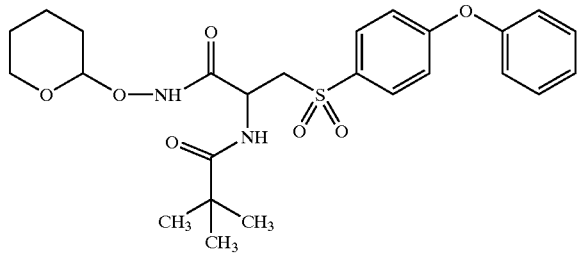

The acid from Example 10b (0.89 mmol, 455 mg) was suspended in tetrahydrofuran. EDC (1.00 mmol, 192 mg) was added. After 15 minutes, THP-O-hydroxylamine was added. The mixture was stirred 20 hours at ambient temperature, diluted with saturated sodium bicarbonate, and extracted with ethyl acetate (125 mL). The organic layer was washed with brine (5 mL), dried over magnesium sulfate, filtered, concentrated and subjected to chromatography (6% methanol/chloroform) to afford the title compound as a solid (260 mg, 58%). The product was characterized spectroscopically. Elemental Anal. Calcd. for $C_{24}H_{31}N_2O_7S(\frac{1}{4}H_2O)$: C, 59.10; H, 6.25; N, 5.51. Found: C, 59.10; H, 6.50; N, 5.31.

EXAMPLE 10d

Preparation of $N^2$-[(1,1-Dimethylethyl)carbamoyl]-$N^1$-hydroxy-3-[(4-phenoxyphenol)-sulphonyl] alaninamide

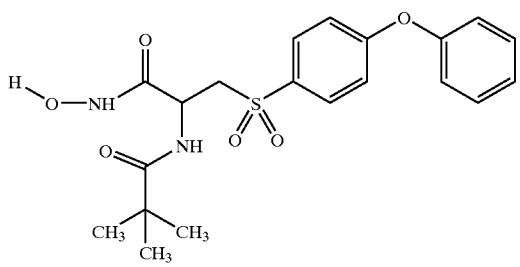

The product of Example 10c (250 mg) was suspended in methanol (10 mL) and toluensulphonic acid (10 mg) was added. After 2 hours, additional toluensulphonic acid (10 mg) was added, and stirring was continued an additional hour. The reaction mixture was concentrated, and the residue was subjected to chromatography (6% methanol/ chloroform), affording the desired hydroxamate as a white foam (166 mg). The product was characterized spectroscopically. Elemental Anal. Calcd. for $C_{20}H_{24}N_2O_6S$: C, 57.13; H, 5.75; N, 6.66. Found: C, 52.67; H, 5.32; N, 5.91.

EXAMPLE 11a

Preparation of N-Acetyl-3-[(4-fluorophenyl) sulfonyl]alanine, Metyl Ester

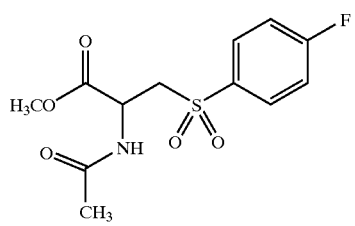

To a solution of methyl 2-acetamidoacrylate (10.0 g, 69.9 mmol) in 100 mL of methanol, cooled to zero degrees C., was added 4-fluorothiophenol (7.44 mL, 69.9 mmol) followed by triethylamine (9.74 mL, 69.9 mmol). The mixture stirred under a nitrogen atmosphere for 4 hours. The solution was poured into a slurry of Oxone® (86 g, 140 mmol) in $H_2O$ (250 mL) and MeOH (125 mL). After stirring at room temperature for 18 hours, the mixture was partitioned between EtOAc (200 mL) and $H_2O$ and washed with saturated $NaHCO_3$ (3×100 mL) and brine (1×100 mL). After concentration in vacuo, trituration with diethyl ether afforded the title compound as a white solid (16.3 g, 77%): MS MH$^+$ calcd. for $C_{12}H_{14}NO_5SF$: 304, found 304. HRMS calcd. for $C_{12}H_{14}NO_5SF$: 303.0577, found: 303.0581.

EXAMPLE 11b

Preparation of N-Acetyl-3-[(4-fluorophenyl)sulfonyl]alanine

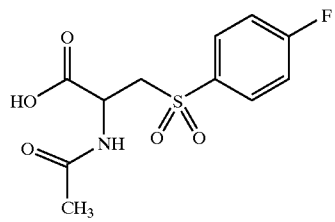

A solution of the title compound of Example 11a (17.9 g, 59.0 mmol) in glacial acetic acid (135 mL) and concentrated HCl (135 mL), was heated to 7 degrees C. for 2 hours. The solution was concentrated under a stream of $N_2$ to yield the title compound as a white solid (17.0 g, quant. yield): MS $MH^+$ calcd. for $C_{11}H_{12}NO_5SF$: 290, found 290. HRMS calc. for $C_{11}H_{13}NO_5SF$: 290.0499, found: 290.0520.

EXAMPLE 11c

Preparation of N-Acetyl-3-[[4-(phenylthio)phenyl]sulfonyl]alanine

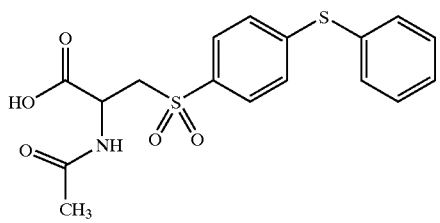

Thiophenol (7.27 g, 71.0 mmol) was added to a solution of the title compound of Example 11b (17.0g, 59.0 mmol) and $K_2CO_3$ (24.4 g, 177 mmol) in DMF (200 mL). After heating at 9 degrees C. for 2 hours, the mixture was concentrated under a stream of $N_2$. The solution was acidified to pH=1 with 1M $KHSO_4$, extracted into EtOAc (2x) and the organic phases were washed with brine and dried over $MgSO_4$. The solution was concentrated in vacuo to yield the title compound as a white solid and was carried on without additional purification.

EXAMPLE 11d

Preparation of 3-[[4-(Phenylthio)phenyl]sulfonyl]alanine, Monohydrochloride

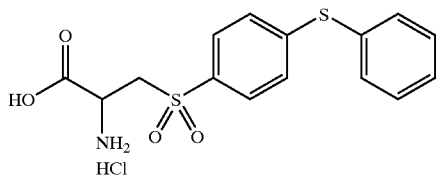

A solution of the title compound of Example 11c (30.0 g) in glacial acetic acid (100 mL) and concentrated HCl (100 mL) was heated to 11 degrees C. for 19 hours. The solution was concentrated and trituration with diethyl ether yielded the title compound as a white solid (17.1 g, 78% for 3 steps):

Anal. Calcd. for $C_{15}H_{15}NO_4S_2 \cdot 1.1$ HCl$\cdot 0.25$ $H_2O$: C, 47.16; H, 4.38; N, 3.67; Cl, 10.21. Found: C, 47.16; H, 4.27; N, 3.91; Cl, 9.95.

EXAMPLE 11e

Preparation of N-(1-Oxopentyl)-3-[[4-(phenylthio)phenyl]sulfonyl]alanine

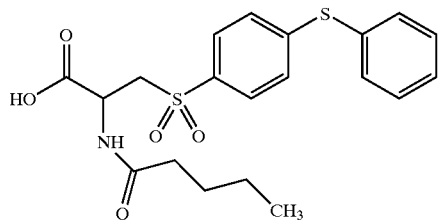

To a solution of the title compound of Example 11d (1.0 g, 2.68 mmol) in $H_2O$ (3 mL) and acetone (2 mL), cooled to zero degrees C., was added triethylamine (1.17 mL, 8.43 mmol), followed by drop-wise addition of valeryl chloride (0.30 mL, 2.52 mmol) in acetone (2 mL). After stirring at room temperature for 18 hours, the mixture was concentrated. The resulting aqueous residue was acidified with 1M $KHSO_4$ and extracted with $CH_2Cl_2$ (3x) The combined organic phases were washed with 1M $KHSO_4$ (1x25 mL) and brine (1x25 mL) and dried over $MgSO_4$. The solution was concentrated in vacuo to yield the title compound as a colorless oil (690 mg, 61%): MS $M^+$ calcd. for $C_{20}H_{23}NO_5S_2$: 421, found 421. HRMS calc for $C_{20}H_{23}NO_5S_2$: 421.1018, found: 421.1025.

EXAMPLE 11f

Preparation of N-[2-oxo-1-[[[4-(Phenylthio)phenyl]sulfonyl]methyl]-2-[[(3,4,5,6-tetrahydro-2H-pyran-2-yl)oxy]amino]ethyl]pentanamide

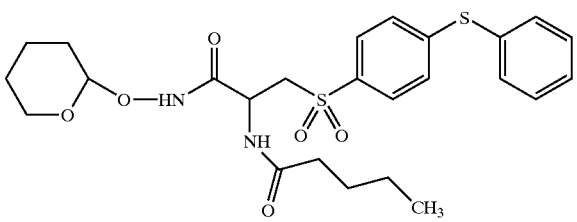

To a solution of the title compound of Example 11e (690 mg, 1.64 mmol) and O-tetrahydro-2H-pyran-2-yl-hydroxylamine (192 mg, 1.64 mmol) in anhydrous THF (40 mL), cooled to zero degrees C., was added EDC (330 mg, 1.72 mmol) and HOBT (264 mg, 1.72 mmol). After stirring at zero degrees C. for 5 hours and at room temperature for 18 hours, the solution was concentrated. The residue was dissolved into EtOAc (50 mL) and washed with 1M $KHSO_4$ (2x50 mL), saturated $NaHCO_3$ (2x50 mL), and brine (1x50 mL) and dried over $Na_2SO_4$. Purification by chromatography (1:1 EtOAc/hexane) yielded the title compound as a colorless oil (500 mg, 59%): Anal. Calcd. for $C_{25}H_{32}N_2O_6S_2$: C, 57.67; H, 6.19; N, 5.38. Found: C, 57.48; H, 6.37; N, 5.11.

EXAMPLE 11g

Preparation of N-[1-[(Hydroxyamino)carbonyl]-2-[[4-(phenylthio)phenyl]sulfonyl]ethyl]pentanamide

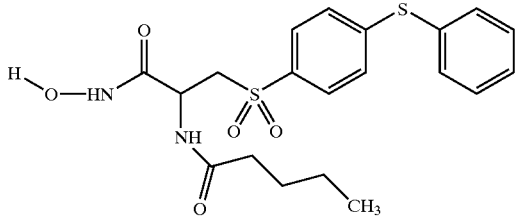

To a solution of the title compound of Example 11f (500 mg, 0.96 mmol) in methanol (20 mL) was added p-toluenesulfonic acid, monohydrate (40 mg, 0.21 mmol). After stirring at room temperature for 2 hours, the solution was concentrated. Purification by chromatography (6:94 MeOH/CHCl$_3$) yielded the title compound as a light beige solid (170 mg, 40%): Anal. Calcd. for C$_{20}$H$_{24}$N$_2$O$_5$S$_2$.0.5 H$_2$O: C, 53.91; H, 5.66; N, 6.29; S, 14.39. Found: C, 53.98; H, 5.44; N, 6.20; S, 14.47.

EXAMPLE 12a

Preparation of

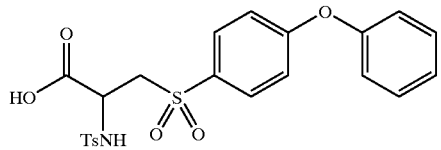

A solution of p-toluenesulfonyl chloride (TsCl; 0.779 g, 4.19 mmol) in 2.4 mL acetone was added drop-wise to a zero degree C. mixture of the title compound of Example 12a (1.50 g, 4.19 mmol) and triethylamine (2.36 mL, 16.9 mmol) in 2.4 mL acetone and 6.4 mL H$_2$O. After 3 hours at room temperature, the mixture was concentrated, diluted with toluene, and concentrated to give a white solid. The solid was washed with water and toluene, and then purified by chromatography (5:95 MeOH/CHCl$_3$) to afford the depicted compound as a white solid (0.75 g, 38% yield). $^1$H NMR spectrum was consistent for the depicted compound.

EXAMPLE 12b

Preparation of

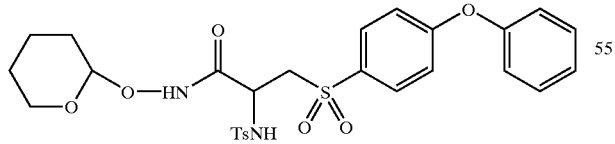

To a solution of the depicted compound of Example 12a (0.75 g, 1.6 mmol), HOBT (0.253 g, 1.7 mmol), and O-tetrahydro-2H-pyran-2-yl-hydroxylamine (0.18 g, 1.6 mmol) in dry THF (22 mL) at zero degrees C. was added EDC (0.316 g, 1.7 mmol). The mixture was slowly warmed to room temperature and stirred overnight (about 18 hours) at room temperature. The solution was concentrated, diluted with ethyl acetate, and washed with H$_2$O and brine. After drying over MgSO$_4$, the filtrate was concentrated to a white solid. The solid was purified by chromatography (40:60 acetone/hexane) to give the title compound as a white solid (0.22 g, 24% yield). The proton NMR spectrum was consistent for the title compound.

EXAMPLE 12c

Preparation of

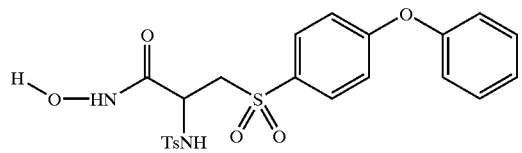

A solution of the depicted compound of Example 12b (0.220 g, 0.383 mmol) and p-toluenesulfonic acid monohydrate (20 mg, 0.105 mmol) in MeOH (5 mL) was stirred at room temperature for 2 hours. The solution was concentrated and triturated with ET$_2$O to afford the depicted compound as an off white solid (50 mg, 43%): MS M$^+$ calcd. for C$_{22}$H$_{22}$N$_2$O$_7$S$_2$490, found 490. HRMS calcd. for C$_{22}$H$_{22}$N$_2$O$_7$S$_2$ 490.0868; found: 490.0863.

EXAMPLE 13a

Preparation of 3-[(4-Phenoxyphenyl)sufonyl]-N-[(phenylmethoxy)carbonyl]alanine

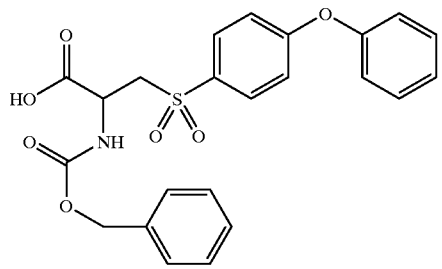

The title compound was prepared by the method of Example 10b, using (0.892 g, 2.5 mmol) of the amino acid of 34a, and using carbobenzyloxy chloride (0.43 mL, 3 mmol) in the place of pivaloyl chloride. The product was a yellow foam (689 mg, 66%), and was characterized spectroscopically. MS MH+ calcd. for C$_{23}$H$_{21}$NO$_7$S 456, found 456. Elemental Anal. Calcd for C$_{23}$H$_{21}$NO$_7$S: C, 59.47; H, 4.77; N, 3.02. Found: C, 59.49; H, 4.35; N, 3.09.

EXAMPLE 13b

Preparation of Phenylmethyl[2-oxo-1-[[(4-phenoxyphenyl)sulfonyl]methyl]-2-[[3,4,5,6-tetrahydro-2H-pyran-2-yl)oxy]amino]ethyl carbamate

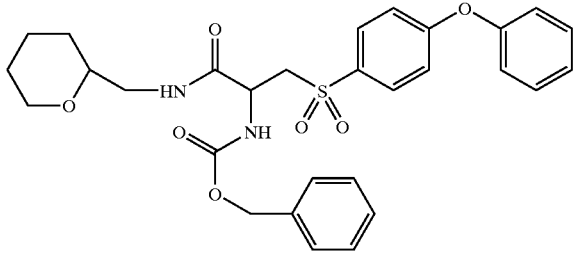

The title O-THP hydroxamate was prepared from the acid from Example 15a (669 mg, 1.6 mmol) by the method of Example 10C, affording after chromatography 208 mg product as a yellow foam. The structure was confirmed spectroscopically.

EXAMPLE 13c

Preparation of Phenylmethyl[1-[(hydroxyamino)carbonyl]-2-[(4-phenoxyphenyl)sulfonyl]ethyl]carbamate

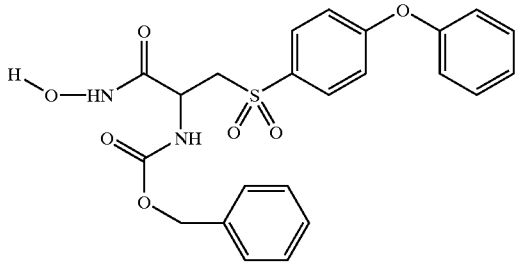

The O-THP hydroxamate from Example 13b (203 mg, 0.36 mmol) was diluted with methanol (10 mL), and toluensulphonic acid (20 mg) was added. The mixture was stirred 1 hour, concentrated, and subjected to chromatography, affording the title hydroxamate (74 mg, 20%) as a white foam, which was characterized spectroscopically. MS MH+ calcd. for $C_{23}H_{22}N_2O_7S$ 470, found 470. Elemental Anal. Calcd for $C_{23}H_{22}N_2O_7S \cdot (H_2O)$: C, 56.53; H, 4.90; N, 5.65. Found: C, 56.55; H, 4.95; N, 5.73.

EXAMPLE 14a

Preparation of N-[(Phenylmethoxy)carbonyl]-3-[[4-(phenylthio)phenyl]sulfonyl]alanine

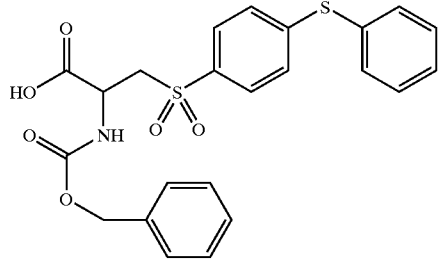

To a solution of the title compound of Example 11d (1.5 g, 4.0 mmol) in $H_2O$ (5 mL) and acetone (3 mL), cooled to zero degrees C., was added triethylamine (1.8 mL, 12.6 mmol), followed by drop-wise addition of benzyl chloroformate (0.57 mL, 4.0 mmol) in acetone (3 mL). After stirring at room temperature for 6 hours, the mixture was concentrated. The resulting aqueous residue was acidified with 1M $KHSO_4$ and extracted with $CH_2Cl_2$ (3×) The combined organic phases were washed with 1M $KHSO_4$ (1×25 mL) and brine (1×25 mL), and dried over $MgSO_4$. The solution was concentrated in vacuo to yield the title compound as a yellow oil (1.4 g, 72%).

EXAMPLE 14b

Preparation of Phenylmethyl-[2-oxo-1-[[[4-(phenylthio)phenyl]sulfonyl]methyl]-2-[[3,4,5,6-tetrahydro-2H-pyran-2-yl]-oxy]amino]ethyl]carbamate

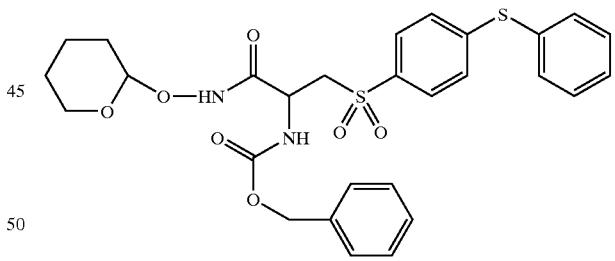

To a solution of the title compound of Example 14a (1.35 g, 2.87 mmol) and O-tetrahydro-2H-pyran-2-yl-hydroxylamine (336 mg, 2.87 mmol) in anhydrous DMF (20 mL), cooled to zero degrees C., was added EDC (578 mg, 3.01 mmol) and HOBT (461 mg, 3.01 mmol). After stirring at zero degrees C. for 1 hour and at room temperature for 2 hours, the solution was partitioned between EtOAc and $H_2O$. The resulting organic phase was washed with 1M $KHSO_4$ (2×50 mL), saturated $NaHCO_3$ (2×50 mL) and brine (1×50 mL), and dried over $Na_2SO_4$. Purification by chromatography (1:1 EtOAc/hexane) yielded the title compound as a colorless oil (500 mg, 31%):

EXAMPLE 14c

Preparation of Phenylmethyl-[2-(hydroxyamino)-2-oxo-1-[[[4-(phenylthio)-phenyl]sulfonyl]methyl]ethyl]carbamate

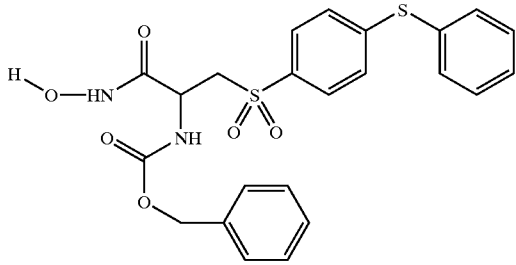

To a solution of the title compound of Example 14b (500 mg, 0.96 mmol) in acetonitrile (20 mL) was added p-toluenesulfonic acid, monohydrate (40 mg, 0.21 mmol). After stirring at room temperature for 1.5 hours, the solution was concentrated. Trituration with diethyl ether yielded the title compound as a white solid (120 mg, 28%): Anal. Calcd. for $C_{23}H_{22}N_2O_6S_2 \cdot 0.2H_2O$: C, 56.36; H, 4.61; N, 5.72; S, 13.08. Found: C, 56.18; H, 4.21; N, 5.50; S, 13.31.

EXAMPLE 15a

Preparation of 2-(Acetylamino)-3-[[4-(phenylthio)phenyl]sulfonyl]-N-[(3,4,5,6-tetrahydro-2H-pyran-2-yl)oxy]propanamide

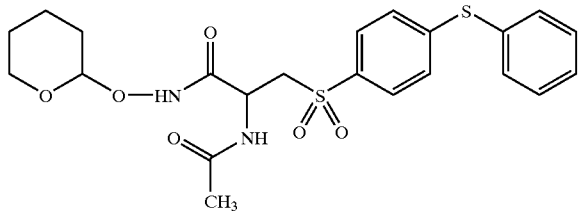

To a solution of the title compound of Example 11c (930 mg, 2.45 mmol) and O-tetrahydro-2H-pyran-2-yl-hydroxylamine (287 mg, 2.45 mmol) in anhydrous DMF (40 mL), cooled to zero degrees C., were added EDC (493 mg, 2.57 mmol) and HOBT (393 mg, 2.57 mmol). After stirring at zero degrees C. for 1 hour and at room temperature for 3 hours, the solution was partitioned between EtOAc and $H_2O$. The resulting organic phase was washed with 1M $KHSO_4$ (2×50 mL), saturated $NaHCO_3$ (2×50 mL) and brine (1×50 mL), and dried over $Na_2SO_4$. Purification by chromatography (1:1 EtOAc/hexane) yielded the title compound as a colorless oil (400 mg, 34%).

EXAMPLE 15b

Preparation of 2-(Acetylamino)-N-hydroxy-3-[[4-(phenylthio)phenyl]sulfonyl]propanamide

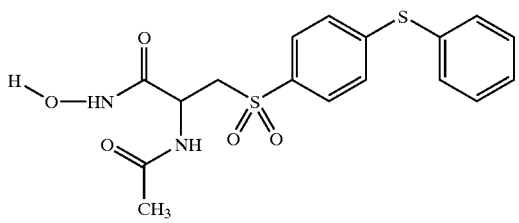

To a solution of the title compound of Example 15a (400 mg, 0.84 mmol) in methanol (40 mg), was added p-toluenesulfonic acid, monohydrate (40 mg, 0.21 mmol). After stirring at room temperature for 2 hours, the solution was concentrated. Purification by flash chromatography (4:96 MeOH/$CHCl_3$) yielded the title compound as a white solid (140 mg, 42%): Anal. Calcd. for $C_{17}H_{18}N_2O_5S_2 \cdot 0.8H_2O$: C, 49.94; H, 4.83; N, 6.85; S, 15.68. Found: C, 50.23; H, 4.62; N, 6.80; S, 15.29.

EXAMPLE 16a

Preparation of 3-[[4-(Phenylthio)phenyl]sulfonyl]alanine, Methyl Ester

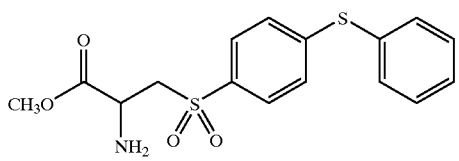

Thionyl chloride (0.44 mL, 6.0 mmol) was added dropwise to a solution of the title compound of Example 11d (1.5 g, 4.0 mmol) in methanol (20 mL). The solution was heated at reflux for 5 hours and then concentrated. After adding EtOAc, the insoluble material was removed by vacuum filtration. The filtrate was washed with saturated $NaHCO_3$ (2×50 mL) and brine (1×50 mL), and dried over $MgSO_4$. The solution was concentrated to yield the title compound as a yellow oil (570 mg, 41%):

EXAMPLE 16b

Preparation of N-[2-[[(Phenylmethoxy)carbonyl]amino]acetyl]-3-[[4-(phenylthio)phenyl]sulfonyl]alanine, Methyl Ester

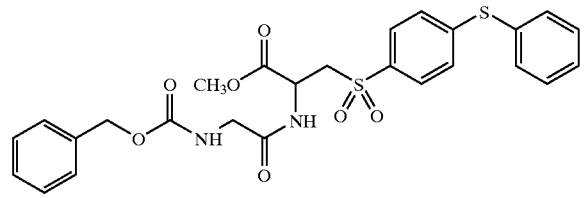

Carboxybenzyloxyglycine succinimidyl ester (500 mg, 1.6 mmol) was added to a solution of the title compound of Example 16a (570 mg, 1.6 mmol) in methylene chloride (20 mL) cooled to zero degrees C. After stirring at room temperature for 20 hours, the solvent was removed in vacuo, and the residue was dissolved into EtOAc. The organic layer was washed with 1M KHSO$_4$ (2×50 mL), saturated NaHCO$_3$ (2×50 mL), and brine (1×50 mL), and dried over MgSO$_4$. Concentration in vacuo yielded the title compound as a colorless oil (800 mg, 93%).

EXAMPLE 16c

Preparation of Phenylmethyl-[2-[[2-(hydroxyamino)-2-oxo-1-[[[4-(phenylthio)-phenyl]sulfonyl]methyl]ethyl]amino]-2-oxoethyl]carbamate

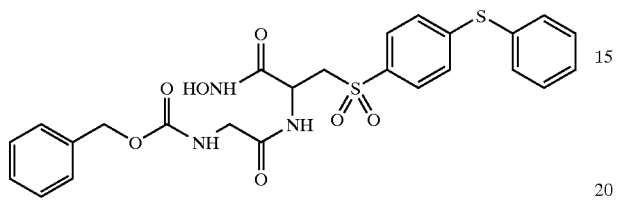

To a solution of the title compound of Example 16b (440 mg, 0.81 mmol) in tetrahydrofuran (9 mL) and methanol (3 mL) was added NH$_2$OH (50% aqueous solution, 0.74 mL, 12 mmol). After stirring for 20 hours at room temperature, the solution was concentrated. Purification by flash chromatography (5:95 MeOH/CHCl$_3$) yielded the title compound as a white solid (80 mg, 18%): Anal. Calcd. for C$_{25}$H$_{25}$N$_3$O$_7$S$_2$.0.25 H$_2$O: C, 54.78; H, 4.69; N, 7.67; S, 11.70. Found: C, 54.78; H, 4.72; N, 7.46; S, 11.53.

EXAMPLE 17a

Preparation of

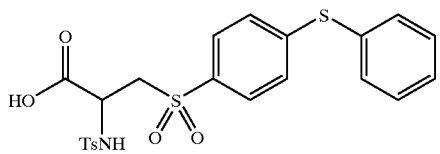

To a solution of the title compound of Example 11d (1.6 g, 4.28 mmol) in H$_2$O (6 mL) and acetone (3 mL) at zero degrees C. was added triethylamine (2.8 mL, 38.2 mmol), followed by drop-wise addition of tosyl chloride (TsCl; 1.24 g, 65.0 mmol) in acetone (3 mL). After stirring at room temperature for 18 hours, the mixture was concentrated. The residue treated with a 10% KHSO$_4$ aqueous solution and CH$_2$Cl$_2$ provided a suspension that was filtered to afford the desired as a white powder (1.3 g, 61.9%). HRMS Calcd. For C$_{22}$H$_{21}$NO$_6$S$_3$: 492.0609. Found: 492.0607.

EXAMPLE 17b

Preparation of

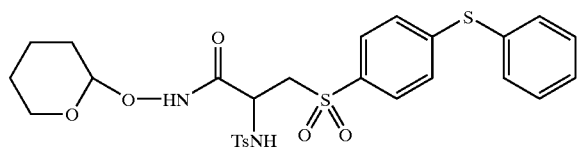

To a solution of the depicted compound of Example 17a (0.6 g, 1.22 mmol) in anhydrous THF (12 mL) and anhydrous DMF (3 mL) at zero degrees C. were added EDC (0.280 g, 1.46 mmol) and HOBT (0.198 g, 1.46 mmol). After stirring at zero degrees C. for 30 minutes, O-tetrahydro-2H-pyran-2-yl-hydroxylamine (0.172 g, 1.46 mmol) was added and the reaction solution was stirred at room temperature for 16 hours. Then the solution was concentrated and the residue was dissolved into EtOAc (50 mL) and washed successively with 10% citric acid (2×50 mL), saturated NaHCO$_3$ (2×50 mL) and brine (1×50 mL), and dried over MgSO$_4$. Purification by chromatography (1.5/60/40 MeOH/EtOAc/hexane) yielded the depicted compound as a white solid (0.47 g, 65.3%).

EXAMPLE 17c

Preparation of

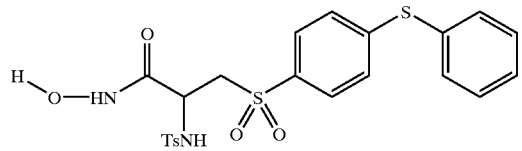

p-Toluenesulfonic acid monohydrate (47 mg, 0.25 mmol) was added to a solution of the depicted compound of Example 17b (430 mg, 0.72 mmol) in methanol (13 mL). After stirring at room temperature for 1.5 hours, a white precipitate appeared that was filtered to afford a white solid. Trituration with ether gave the depicted compound (280 mg, 75.7%): Anal. Calcd. for C$_{22}$H$_{22}$N$_2$O$_6$S$_3$: C, 51.12; H, 4.58; N, 7.95; S, 18.20. Found: C, 51.06; H, 4.59; N, 7.83; S, 18.45.

EXAMPLE 18a

Preparation of

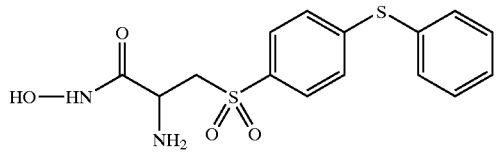

To the title compound of 16a (0.5 g, 1.4 mmol) in MeOH (2 mL) and THF (2 mL) was added 50% aqueous NH$_2$OH (1 mL, 13.5 mmol). The reaction solution was stirred for 2 hours during which time a white precipitate appeared. The resulting suspension was filtered, and the white powder thus obtained was washed with ether (10 mL×3) to afford the depicted compound. Anal. Calcd. For C$_{15}$H$_{16}$N$_2$O$_4$S$_2$: C, 51.12; H, 4.58; N, 7.95; S, 18.20. Found: C, 51.06; H, 4.59; N, 7.83; S, 18.45.

EXAMPLE 19a

Preparation of

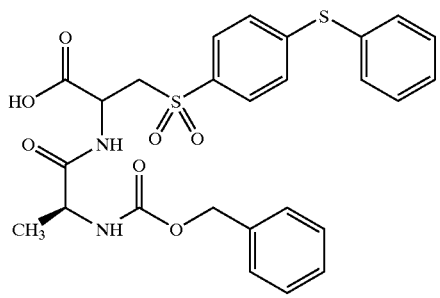

To a solution of Cbz-alanine (1.43 g, 6.4 mmol) in DMF at zero degrees C. were added EDC (1.23 g, 6.4 mmol) and HOBT (0.87 g, 6.4 mmol). After 30 minutes at zero degrees C., the title compound of Example 11d (2 g, 5.36 mmol) was added to the solution followed by N-methylmorpholine (1.82 mL, 16.5 mmol). The reaction solution was left stirring overnight (about 18 hours) at room temperature. The reaction was concentrated and the resulting residue was dissolved in aqueous 10% $KHSO_4$ solution. The aqueous solution was extracted with ethyl acetate and the combined organic phases were washed with 10% $KHSO_4$ aqueous solution, dried over $MgSO_4$ and evaporated to afford the depicted compound.

EXAMPLE 19b

Preparation of

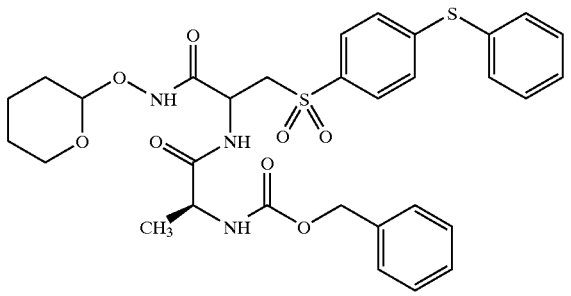

To a solution of the depicted compound of Example 19a (1.0 g, 1.84 mmol) in dry DMF (10 mL) at zero degrees C. were added EDC (0.422 g, 2.2 mmol) and HOBT (0.299 g, 2.2 mmol). After stirring at zero degrees C. for 30 minutes, O-tetrahydro-2H-pyran-2-yl-hydroxylamine (0.323 g, 2.6 mmol) was added. The reaction solution was then stirred at room temperature for 16 hours. Concentration of the solution afforded a residue that was dissolved into EtOAc (50 mL) and washed with 10% citric acid (2×50 mL), saturated $NaHCO_3$ (2×50 mL), and brine (1×50 mL), and then dried over $MgSO_4$. Evaporation gave a residue that was purified by chromatography on silica gel (2/50/50 MeOH/EtOAc/hex) to afford the depicted compound as white solid (0.6 g, 50.8%). Anal. calcd. for $C_{31}H_{35}N_3O_8S_2$: C, 58.02; H, 5.5; N, 6.55; S, 9.99. Found: C, 57.69; H, 5.59; N, 6.35; S, 10.33.

EXAMPLE 19c

Preparation of

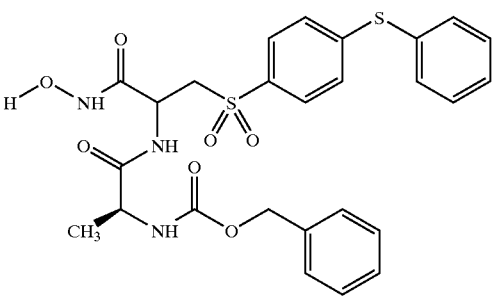

p-Toluenesulfonic acid monohydrate (25 mg, 0.13 mmol) was added to a solution of the title compound of Example 19b (170 mg, 0.26 mmol) in methanol (1 mL) and acetonitrile (4 mL). After stirring at room temperature overnight (about 18 hours), the reaction solution was concentrated to a residue that was purified by chromatography on silica gel (5/100 MeOH/$CH_2Cl_2$) to afford the title compound as white solid (82 mg, 55.5%): Anal. Calcd. for $C_{26}H_{27}N_3O_7S_2$: C, 56.00; H, 4.88; N, 7.54; S, 11.50. Found: C, 56.11; H, 5.22; N, 7.28; S, 11.22.

EXAMPLE 20a

Preparation of

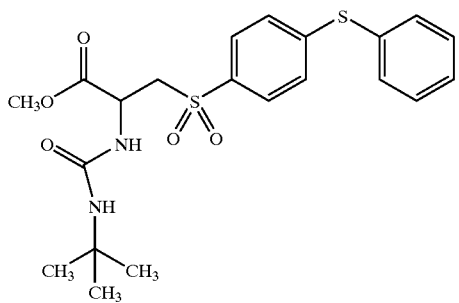

The title compound of Example 16a (0.43 g, 1.2 mmol) in $CH_2Cl_2$ was added t-butyl isocyanate (0.48 mL, 4.2 mmol). After stirring for 3 days at room temperature, the reaction solution was diluted with ethyl acetate (50 mL) and washed successively with 10% citric acid (2×50 mL), saturated $NaHCO_3$ (2×50 mL), and brine (1×50 mL) and then dried over $MgSO_4$. Evaporation of the solvent gave the title compound as crystalline white solid. Anal. Calcd. For $C_{21}H_{26}N_2O_5S_2$: C, 55.98; H, 5.82; N, 6.22; S, 14.25. Found: C, 55.78; H, 6.00; N, 6.09; S, 14.25.

EXAMPLE 20b

Preparation of

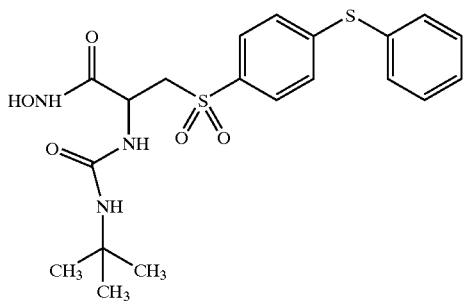

Aqueous NH$_2$OH (0.9 mL, 15.8 mmol) was added to a solution of the depicted compound of Example 20a (0.47 g, 1.04 mmol) in MeOH (2 mL) and THF (2 mL). After stirring overnight (about 18 hours) at room temperature, the reaction solution was concentrated to a residue that was purified by chromatography on silica gel (5/100 MeOH/CH$_2$Cl$_2$) to afford the depicted compound as a white solid (287 mg, 61.0%): Anal. Calcd. For C$_{20}$H$_{25}$N$_3$O$_5$S2.H$_2$O: C, 51.16; H, 5.80; N, 8.95; S, 13.66. Found: C, 51.34; H, 5.60; N, 9.41; S, 13.57.

Example Compounds 21–70 are similarly prepared to those above.

EXAMPLE 21

In Vitro Metalloprotease Inhibition

The compounds prepared in the manner described in the Examples above were assayed for activity by an in vitro assay. Following the procedures of Knight et al., *FEBS Lett.* 296(3):263 (1992). Briefly, 4-aminophenylmercuric acetate (APMA) or trypsin-activated MMPs were incubated with various concentrations of the inhibitor compound at room temperature for 5 minutes.

More specifically, recombinant human MMP-13 and MMP-1 enzymes were prepared in laboratories of the assignee following usual laboratory procedures. MMP-13 from a full length cDNA clone was expressed as a proenzyme using a baculovirus as discussed in V. A. Luckow, Insect Cell Expression Technology, pages 183–218, in *Protein Engineering: Principles and Practice*, J. L. Cleland et al eds., Wiley-Liss, Inc., (1996). See, also, Luckow et al., *J. Virol.*, 67:4566–4579 (1993); O'Reilly et al., *Baculovirus Expression Vectors: A Laboratory Manual*, W. H. Freeman and Company, New York, (1992); and King et al., *The Baculovirus Expression System: A Laboratory Guide*, Chapman & Hall, London (1992) for further details on use of baculovirus expression systems. The expressed enzyme was purified first over a heparin agarose column and then over a chelating zinc chloride column. The proenzyme was activated by APMA for use in the assay.

MMP-1 expressed in transfected HT-1080 cells was provided by Dr. Harold Welgus of Washington University, St. Louis, Mo. The enzyme was also activated using APMA and was then purified over a hydroxamic acid column. Further specifics for preparation and use of these enzymes can be found in the scientific literature describing these enzymes. See, for example, *Enzyme Nomenclature*, Academic Press, San Diego, Calif. (1992) and the citations therein, and Frije et al., *J. Biol. Chem.*, 26(24): 16766–16773 (1994).

The enzyme substrate is a methoxycoumarin-containing polypeptide having the following sequence:

MCA-ProLeuGlyLeuDpaAlaArgNH$_2$, wherein MCA is methoxycoumarin and Dpa is 3-(2,4-dinitrophenyl)-L-2,3-diaminopropionyl alanine. This substrate is commolercially available from Baychem as product M-1895.

The buffer used for assays contained 100 mmol Tris-HCl, 100 mmol NaCl, 10 mmol CaCl$_2$ and 0.05 percent polyethyleneglycol (23) lauryl ether at a pH value of 7.5. Assays were carried out at room temperature, and dimethyl sulfoxide (DMSO) at a final concentration of 1 percent was used to dissolve inhibitor compound.

The assayed inhibitor compound in DMSO/buffer solution was compared to an equal amount of DMSO/buffer with no inhibitor as control using Microfluor™ White Plates (Dynatech). The inhibitor or control solution was maintained in the plate for 10 minutes and the substrate was added to provide a final concentration of 4 µM.

In the absence of inhibitor activity, a fluorogenic peptide was cleaved at the gly-leu peptide bond, separating the highly fluorogenic peptide from a 2,4-dinitrophenyl quencher, resulting in an increase of fluorescence intensity (excitation at 328 nm/emission at 415 nm). Inhibition was measured as a reduction in fluorescent intensity as a function of inhibitor concentration, using a Perkin Elmer L550 plate reader. The IC$_{50}$ values were calculated from those values. The results are set fourth in the Inhibition Table below, reported in terms of IC$_{50}$ values in nanomolar (nM) amounts.

Inhibition Table
MMP ENZYME INHIBITION PROFILE
(nM, IC$_{50}$)

| Example | MMP-1 | MMP-2 | MMP-13 |
|---|---|---|---|
| 1 | 300 | | 15.0 |
| 2 | 1500 | | 15.0 |
| 3 | 2000 | | 25.0 |
| 4 | 400 | | 3.5 |
| 5 | 100 | | 200 |
| 6 | 40 | | <1.0 |
| 7 | 200 | | 2.5 |
| 8 | 600 | | 60.0 |
| 9g | 770 | | 1.1 |
| 10d | 1600 | | 2.7 |
| 11g | 10000 | | 6.0 |
| 12c | 400 | <0.1 | 0.6 |
| 13c | 1400 | | 1.1 |
| 14c | >10000 | | 3.7 |
| 15b | >10000 | 2.2 | 5.9 |
| 16c | >10000 | | 0.8 |
| 17c | 600 | | 0.4 |
| 18a | >10000 | | 24.0 |
| 19a | >10000 | | 0.8 |
| 20b | >10000 | | 4.0 |
| 21 | 300 | | 15.0 |
| 22 | 250 | | 15.0 |
| 23 | >10000 | | 1500 |
| 24 | 5200 | | 650 |
| 25 | 1.0 | | 1.0 |
| 26 | | | |
| 27 | >10000 | | 14.0 |
| 28 | >10000 | 5.5 | 13.0 |
| 29 | >10000 | | 7.0 |
| 30 | 10000 | 0.5 | 2.9 |
| 31 | 3000 | 0.8 | 0.4 |
| 32 | 8000 | | 0.4 |
| 33 | 500 | 0.2 | 0.3 |
| 34 | >10000 | | 5.0 |
| 35 | 3000 | | 0.2 |

-continued

Inhibition Table
MMP ENZYME INHIBITION PROFILE
(nM, IC$_{50}$)

| Example | MMP-1 | MMP-2 | MMP-13 |
|---|---|---|---|
| 36 | >10000 | | 2.5 |
| 37 | 350 | 0.25 | 0.4 |
| 38 | 170 | 0.5 | 0.5 |
| 39 | 114, 225 | 0.3, 0.8 | 0.3, 1.1 |
| 40 | 1600 | 0.3 | 0.3 |
| 41 | 440, 670 | 0.3, 0.5 | 0.4, 1.0 |
| 42 | >10000 | 40.0 | 41.5 |
| 43 | 90.0 | 0.2 | 0.2 |
| 44 | 900 | 0.3 | 0.8 |
| 45 | >10000 | | 5.0 |
| 46 | 1310 | 0.3 | 1.1 |
| 47 | 258 | 0.6 | 45.3 |
| 48 | 475 | <0.1 | 0.2 |
| 49 | >10000 | 80.0 | 160 |
| 50 | 316 | 0.3 | 0.3 |
| 51 | 295 | 0.3 | 0.4 |
| 52 | >10000 | 5.0 | 24.0 |
| 53 | 8100 | 0.3 | 2.1 |
| 54 | 345 | 0.2 | 0.3 |
| 55 | 1600 | 1.3 | 1.6 |
| 56 | 1200 | 0.2 | 0.3 |
| 57 | >10000 | 540 | 580 |
| 58 | 4400 | 3.2 | 2.4 |
| 59 | 580 | 0.4 | 0.8 |
| 60 | 440 | 0.3 | 0.4 |
| 61 | >10000 | 1.1 | 60.0 |
| 62 | 72.3 | 23.9 | 1200 |
| 63 | 3050 | 1.0 | 21.5 |
| 64 | 7000 | 0.4 | 8.1 |
| 65 | >10000 | 184 | 161 |
| 66 | 2350 | 0.5 | 1.1 |
| 67 | 2400 | 1.3 | 2.4 |
| 68 | >10000 | 0.4 | 1.4 |
| 69 | 700 | 0.2 | 0.6 |
| 70 | 130 | 0.2 | 0.4 |

EXAMPLE 22

Tumor Necrosis Factor Assays

Cell Culture.

The cells used in the assay are the human moncytic line U-937 (ATCC CRL-1593). The cells are grown RPMI w/10% FCS and PSG supplement (R-10) and are not permitted to overgrow. The assay is carried out as follows:

1. Count, then harvest cells by centrifugation. Resuspend the pellet in R-10 supplement to a concentration of 1.540× 10$^6$ cells/mL.

2. Add test compound in 65 μL R-10 to the appropriate wells of a 96-well flat bottom tissue culture plate. The initial dilution from a DMSO stock (100 mM compound) provides a 400 μM solution, from which five additional three-fold serial dilutions are made. Each dilution of 65 μL (in triplicate) yields final compound test concentrations of 100 μM, 33.3 μM, 11.1 μM, 3.7 μM, 1.2 μM and 0.4 μM.

3. The counted, washed and resuspended cells (200,000 cells/well) in 130 μL are added to the wells.

4. Incubation is for 45 minutes to one hour at 37° C. in 5% CO$_2$ in a water saturated container.

5. R-10 (65 μL)containing 160 ng/mL PMA (Sigma) is added to each well. 6. The test system is incubated at 37° C. in 5% CO$_2$ overnight (18–20 hours) under 100% humidity.

7. Supernatant, 150 μL, is carefully removed from each well for use in the ELISA assay.

8. For toxicity, a 50 μL aliquot of working solution containing 5 mL R-10, 5 mL MTS solution [CellTiter 96 AQueous One Solution Cell Proliferation Assay Cat.#G358/ 0,1 (Promega Biotech)] and 250 μL PMS solution are added to each well containing the remaining supernatant and cells and the cells incubated at 37° C. in 5% CO$_2$ until the color develops.

The system is excited at 570 nm and read at 630 nm.

TNFα ELISA Assay

Coat Immulon® 2 plates with 0.1 mL/well of 1 ug/mL Genzyme mAb in 0.1 M NaHCO$_3$ pH 8.0 buffer overnight (about 18–20 hours) at 4° C., wrapped tightly in Saran® wrap.

Flick out coating solution and block plates with 0.3 mL/well blocking buffer overnight at 4° C., wrapped in Saran® wrap.

Wash wells thoroughly 4× with wash buffer and completely remove all wash buffer. Add 0.1 mL/well of either samples or rhTNFα standards. Dilute samples if necessary in appropriate diluent (e.g. tissue culture medium). Dilute standard in same diluent. Standards and samples should be in triplicates.

Incubate at 37° C. for 1 hour in humidified container.

Wash plates as above. Add 0.1 mL/well of 1:200 dilution of Genzyme rabbit anti-hTNFα.

Repeat incubation.

Repeat wash. Add 0.1 mL/well of 1 μg/mL Jackson goat anti-rabbit IgG (H+L)-peroxidase.

Incubate at 37° C. for 30 minutes.

Repeat wash. Add 0.1 mL/well of peroxide-ABTS solution.

Incubate at room temperature for 5–20 minutes.

Read OD at 405 nm.

12 Reagents are:

Genzyme mouse anti-human TNF monoclonal (Cat.# 80-3399-01)

Genzyme rabbit anti-human TNF polyclonal (Cat. #IP-300)

Genzyme recombinant human TNF (Cat.#TNF-H).

Jackson Immunoresearch peroxide-conjugated goat anti-rabbit IgG (H+L) (Cat.#111-035-144).

Kirkegaard/Perry peroxide ABTS solution (Cat#50-66-01).

Immulon 2 96-well microtiter plates.

Blocking solution is 1 mg/mL gelatin in PBS with 1×thimerasol.

Wash buffer is 0.5 mL Tween 20 in 1 liter of PBS.

Results:

TABLE 2

Inhibition of TNF? Release

| Example Number | Per Cent Inhibition of TNF? Release in Micromolar (μM) or IC$_{50}$ (μM) [average] |
|---|---|
| 3 | 3.72% @ 10 μM (n = 5) |
| 7 | IC$_{50}$ = >50 μM |
| 4 | -3.8% @10 (n = 3) |
|   | IC$_{50}$ = >50 μM |
| 8 | IC$_{50}$ = >50 μM |
| 22 | IC$_{50}$ = >29 μM |
| 5 | -10.8% @ 10 (n = 3) |
|   | IC$_{50}$ = >50 μM |
| 23 | IC$_{50}$ = >50 μM |
| 24 | IC$_{50}$ = >50 μM |
| 25 | IC$_{50}$ = 14.0 μM |

From the foregoing, it will be observed that numerous modifications and variations can be effectuated without departing from the true spirit and scope of the novel concepts of the present invention. It is to be understood that no limitation with respect to the specific example presented is intended or should be inferred. The disclosure is intended to cover by the appended claims all such modifications as fall within the scope of the claims.

What is claimed:

1. A compound or pharmaceutically acceptable salt thereof, the compound corresponding in structure to a formula selected from the group consisting of:

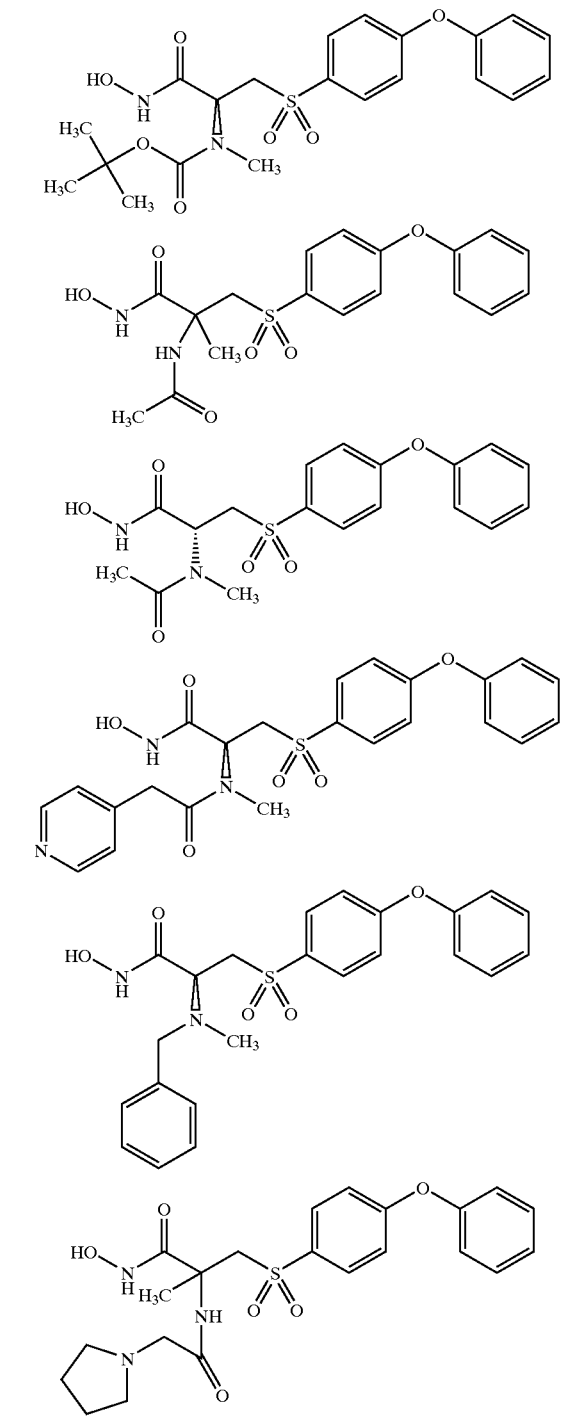

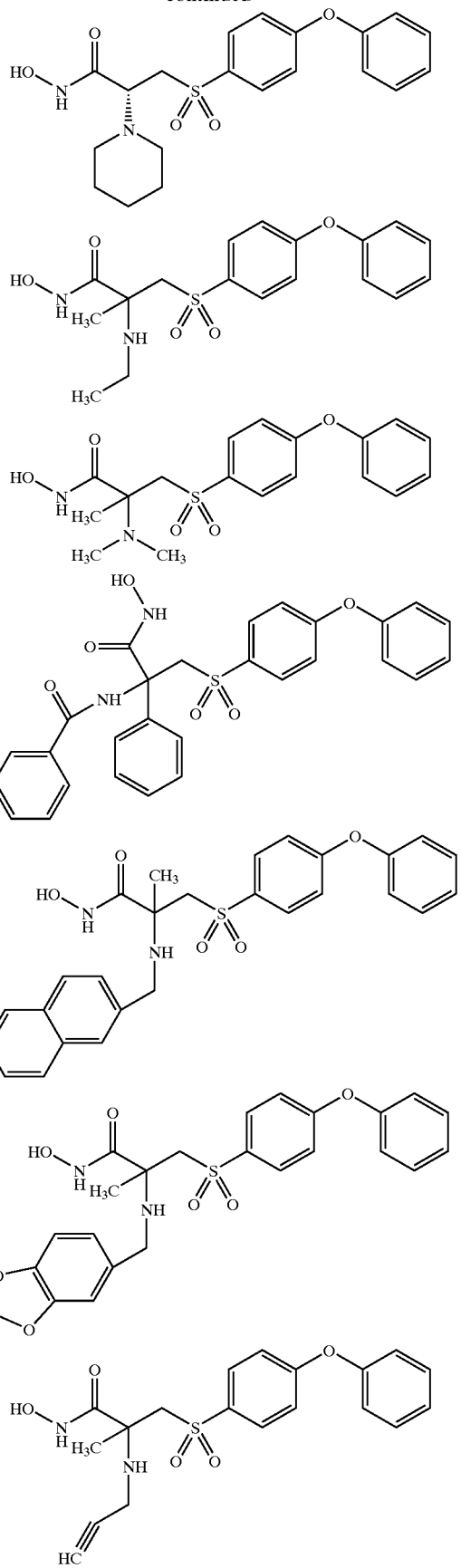

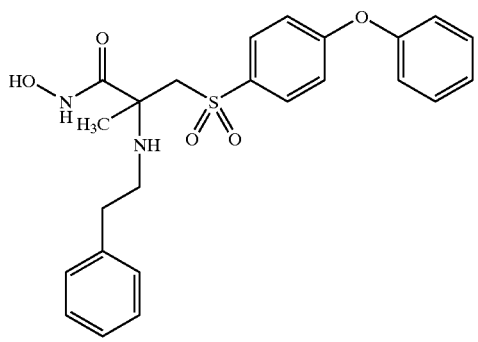

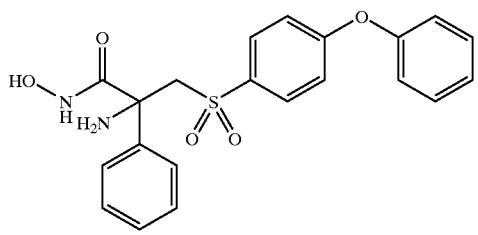

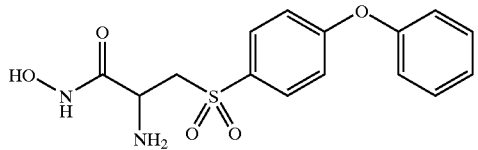

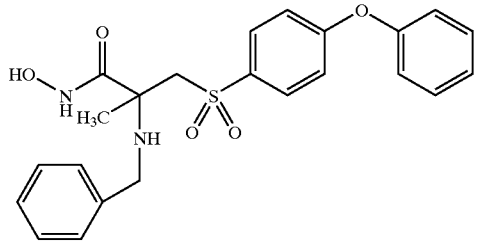

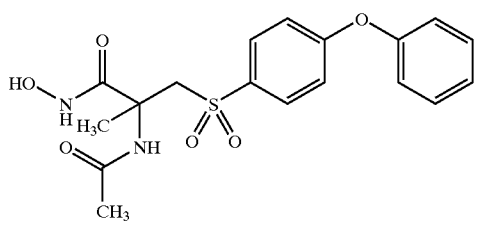

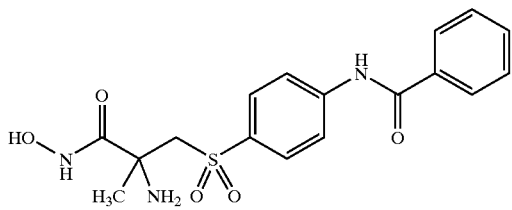

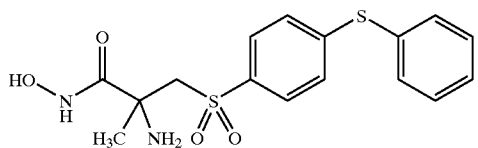

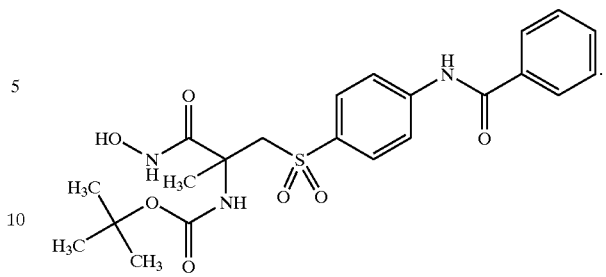

2. The compound or salt according to claim 1 wherein said compound corresponds in structure to the formula below

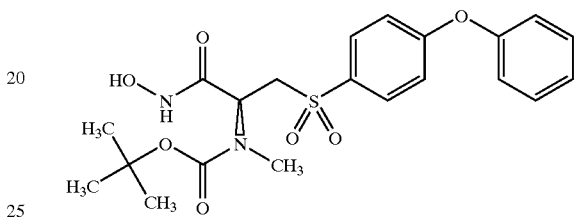

3. The compound or salt according to claim 1 wherein said compound corresponds in structure to the formula below

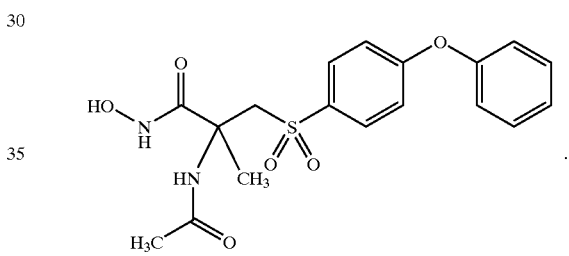

4. The compound or salt according to claim 1 wherein said compound corresponds in structure to the formula below

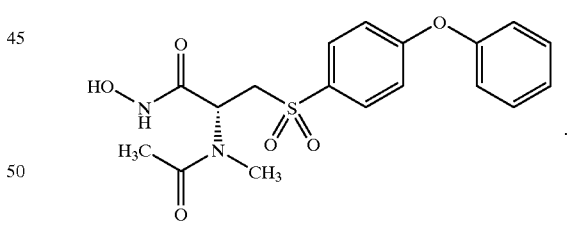

5. The compound or salt according to claim 1 wherein said compound corresponds in structure to the formula below

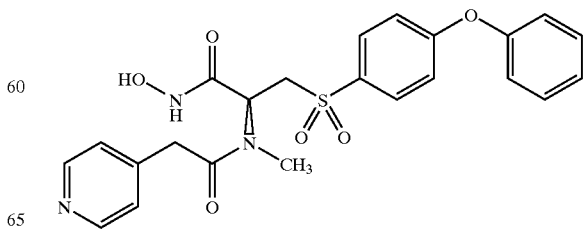

6. The compound or salt according to claim 1 wherein said compound corresponds in structure to the formula below

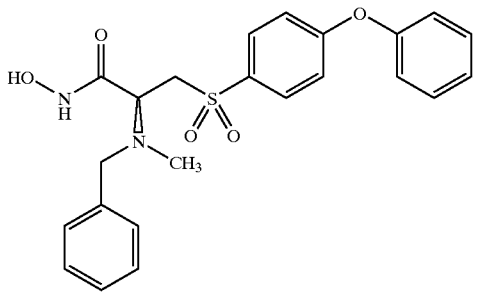

7. The compound or salt according to claim 1 wherein said compound corresponds in structure to the formula below

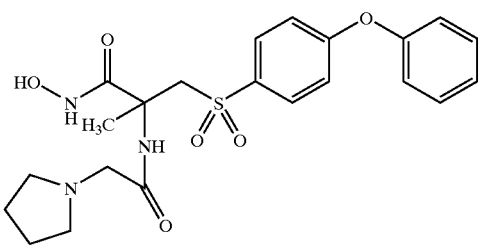

8. The compound or salt according to claim 1 wherein said compound corresponds in structure to the formula below

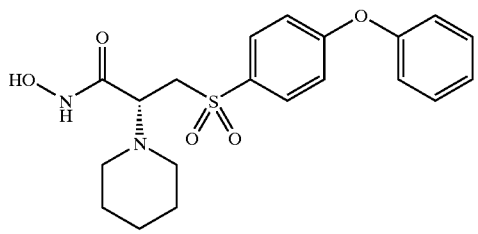

9. The compound or salt according to claim 1 wherein said compound corresponds in structure to the formula below

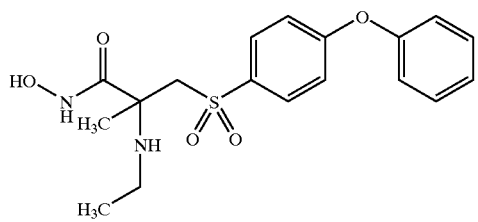

10. The compound or salt according to claim 1 wherein said compound corresponds in structure to the formula below

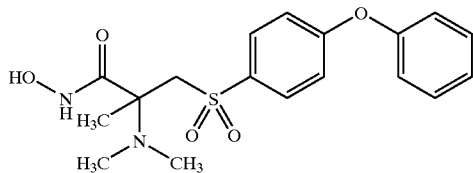

11. The compound or salt according to claim 1 wherein said compound corresponds in structure to the formula below

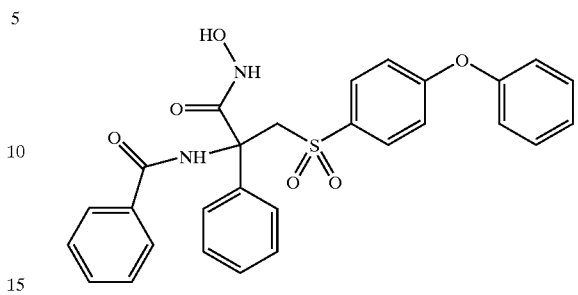

12. The compound or salt according to claim 1 wherein said compound corresponds in structure to the formula below

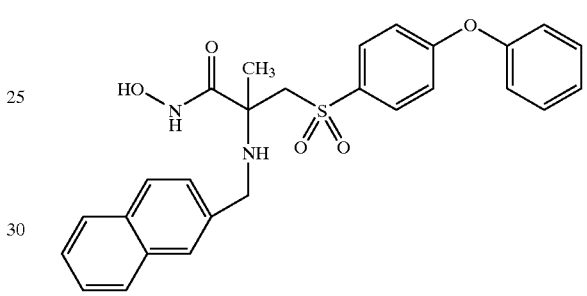

13. The compound or salt according to claim 1 wherein said compound corresponds in structure to the formula below

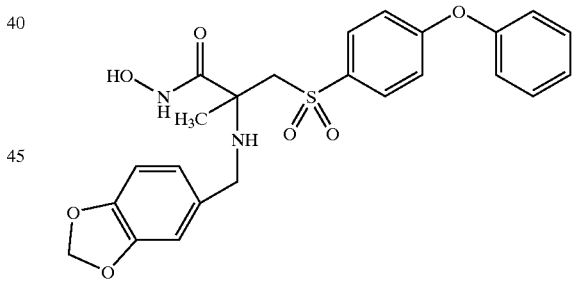

14. The compound or salt according to claim 1 wherein said compound corresponds in structure to the formula below

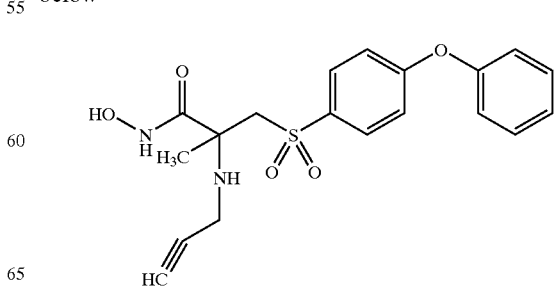

15. The compound or salt according to claim 1 wherein said compound corresponds in structure to the formula below

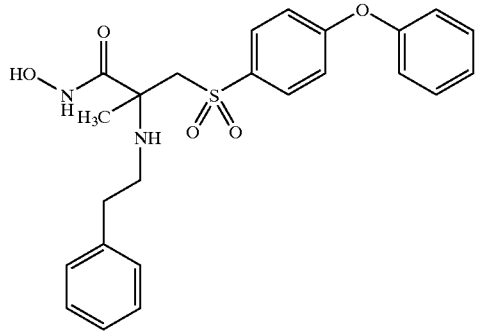

16. The compound or salt according to claim 1 wherein said compound corresponds in structure to the formula below

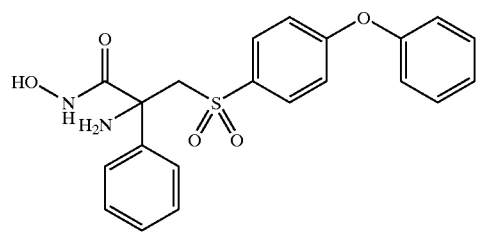

17. The compound or salt according to claim 1 wherein said compound corresponds in structure to the formula below

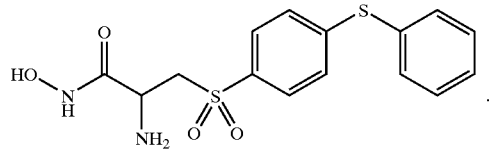

18. The compound or salt according to claim 1 wherein said compound corresponds in structure to the formula below

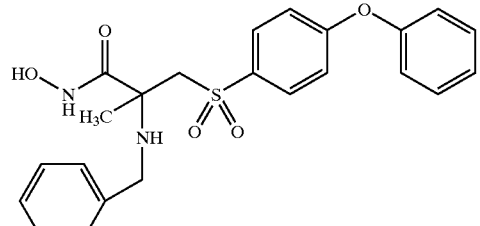

19. The compound or salt according to claim 1 wherein said compound corresponds in structure to the formula below

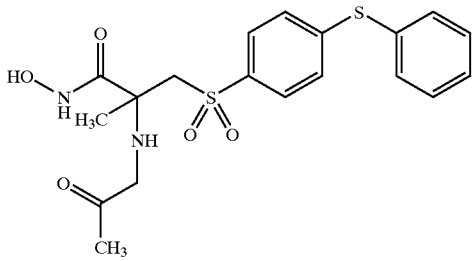

20. The compound or salt according to claim 1 wherein said compound corresponds in structure to the formula below

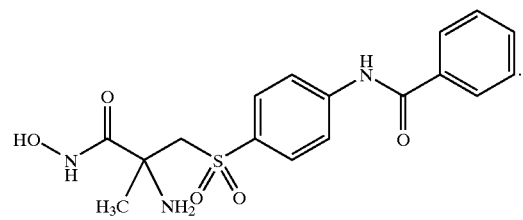

21. The compound or salt according to claim 1 wherein said compound corresponds in structure to the formula below

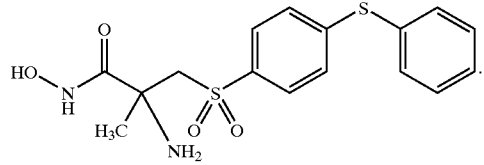

22. The compound or salt according to claim 1 wherein said compound corresponds in structure to the formula below

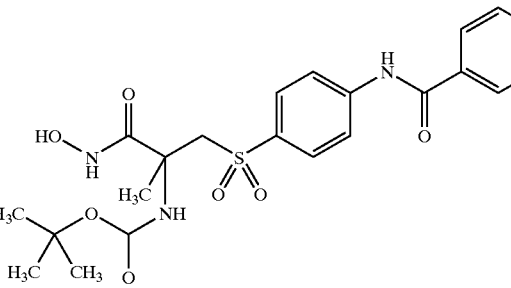

23. A compound or pharmaceutically acceptable salt thereof, the compound corresponding in structure to a formula selected from the group consisting of:
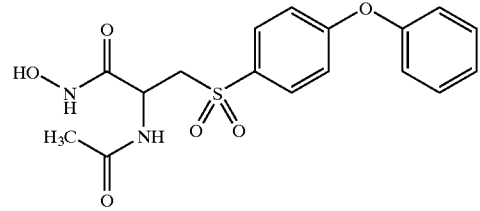
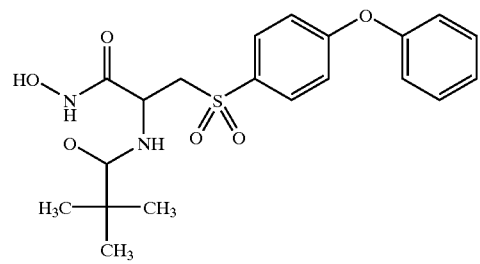
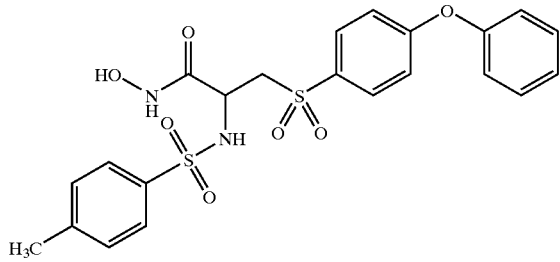
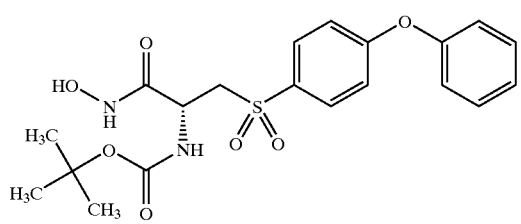
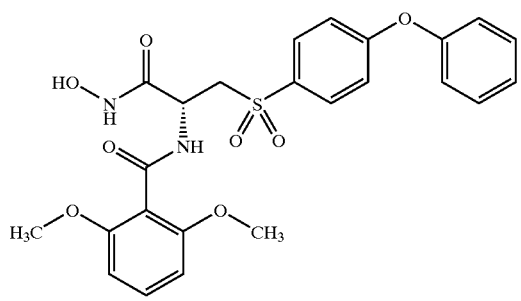
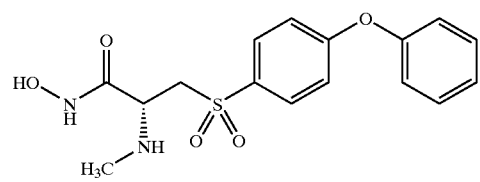
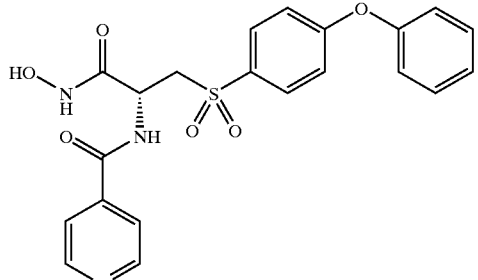
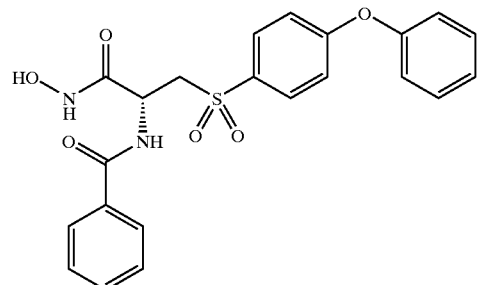
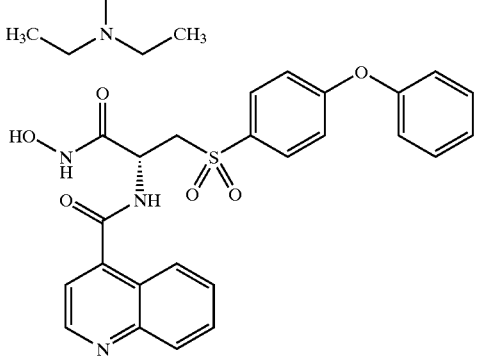
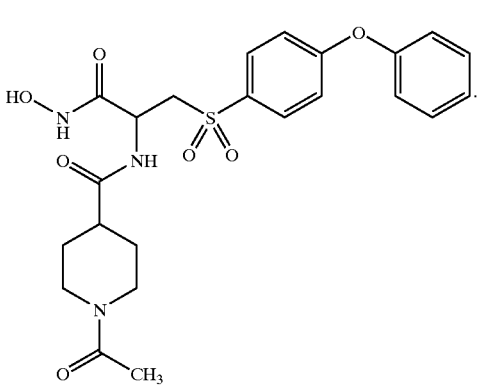
24. The compound or salt according to claim 23 wherein said compound corresponds in structure to the formula below
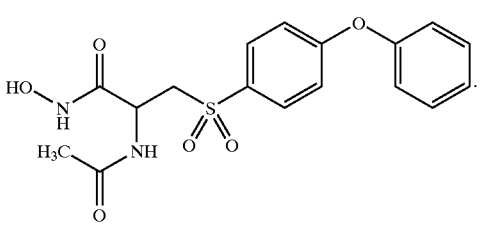

25. The compound or salt according to claim 23 wherein said compound corresponds in structure to the formula below

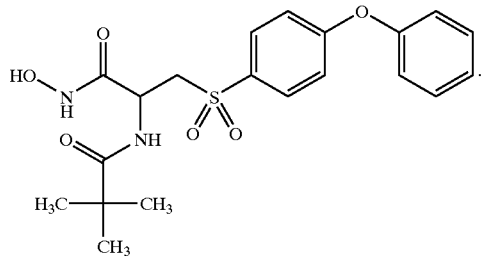

26. The compound or salt according to claim 23 wherein said compound corresponds in structure to the formula below

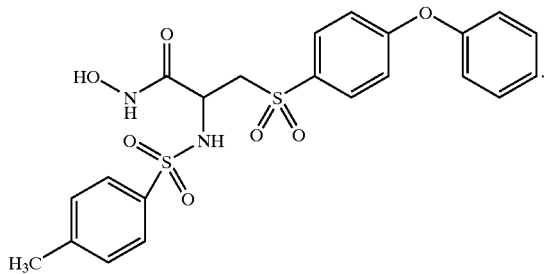

27. The compound or salt according to claim 23 wherein said compound corresponds in structure to the formula below

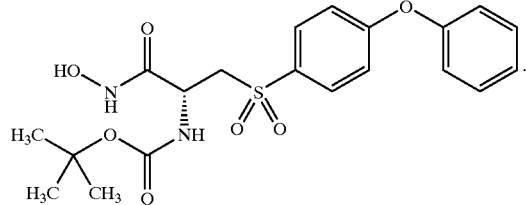

28. The compound or salt according to claim 23 wherein said compound corresponds in structure to the formula below

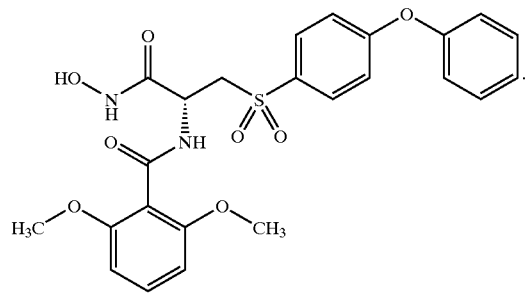

29. The compound or salt according to claim 23 wherein said compound corresponds in structure to the formula below

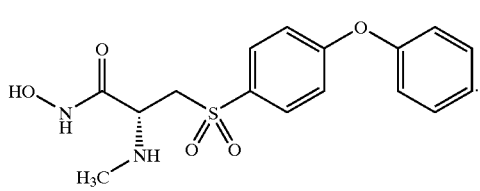

30. The compound or salt according to claim 23 wherein said compound corresponds in structure to the formula below

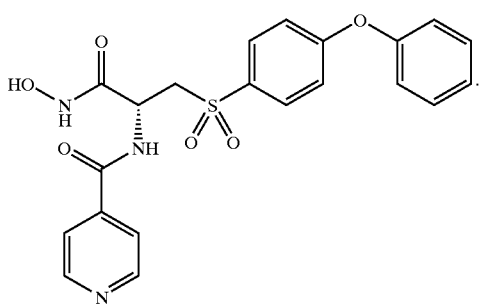

31. The compound or salt according to claim 23 wherein said compound corresponds in structure to the formula below

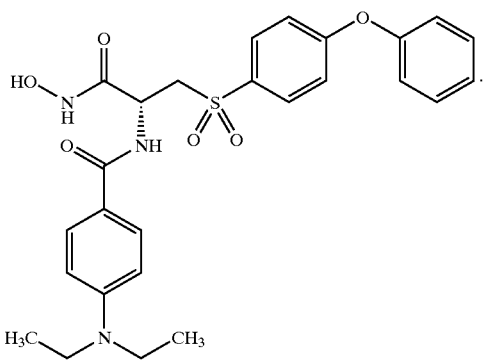

32. The compound or salt according to claim 23 wherein said compound corresponds in structure to the formula below

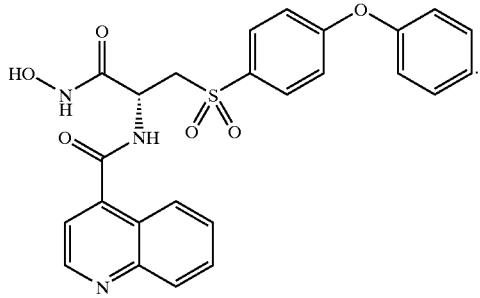

33. The compound or salt according to claim 23 wherein said compound corresponds in structure to the formula below

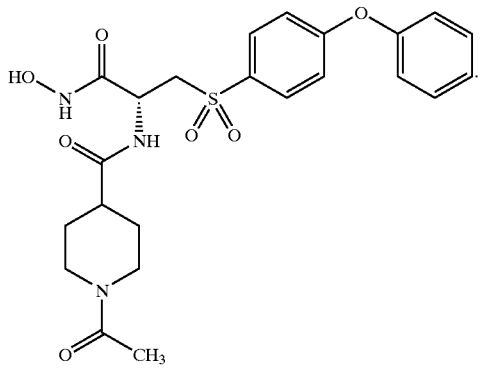

34. A compound or pharmaceutically acceptable salt thereof, wherein said compound corresponds in structure to the formula below:

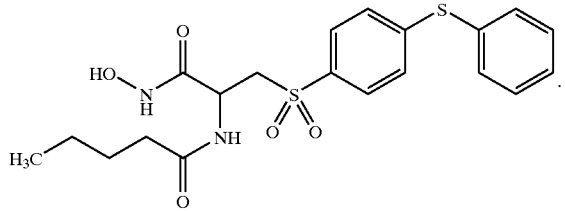

35. A compound or pharmaceutically acceptable salt thereof, wherein said compound corresponds in structure to the formula below:

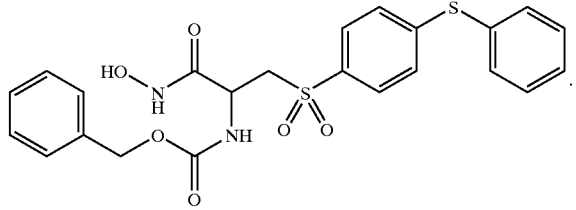

36. A compound or pharmaceutically acceptable salt thereof, wherein said compound corresponds in structure to the formula below:

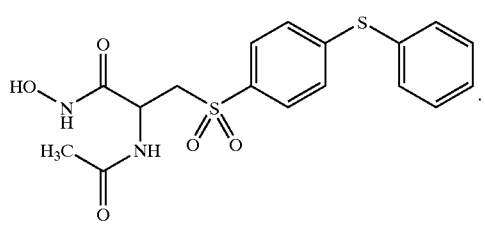

37. A compound or pharmaceutically acceptable salt thereof, wherein said compound corresponds in structure to the formula below:

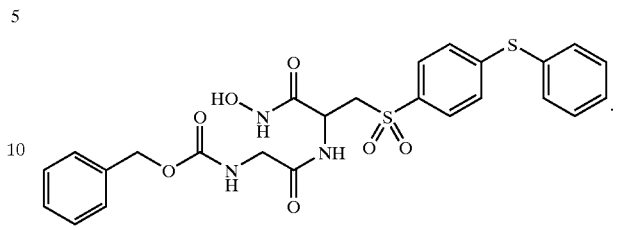

38. A compound or pharmaceutically acceptable salt thereof, wherein said compound corresponds in structure to the formula below:

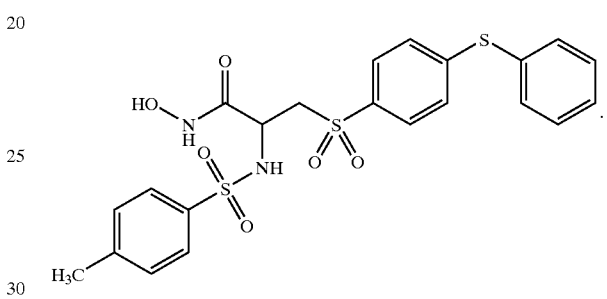

39. A compound or pharmaceutically acceptable salt thereof, wherein said compound corresponds in structure to the formula below:

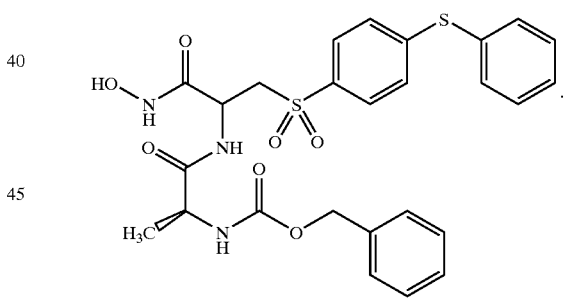

40. A compound or pharmaceutically acceptable salt thereof, wherein said compound corresponds in structure to the formula below:

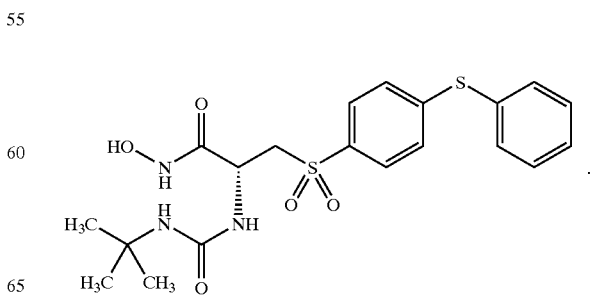

41. A compound or pharmaceutically acceptable salt thereof, wherein said compound corresponds in structure to the formula below:

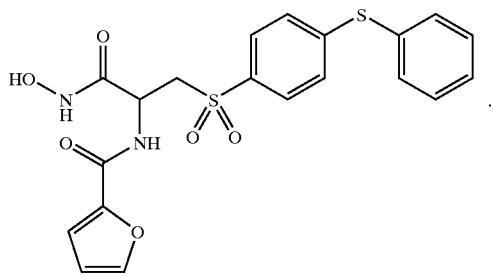

42. A compound or pharmaceutically acceptable salt thereof, wherein said compound corresponds in structure to the formula below:

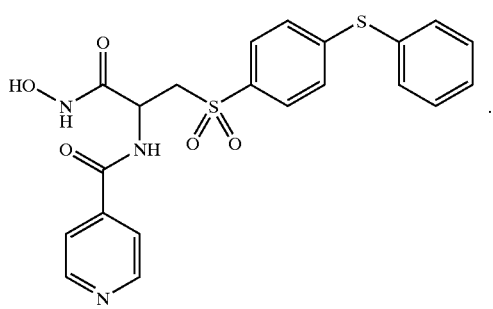

43. A compound or pharmaceutically acceptable salt thereof, wherein said compound corresponds in structure to the formula below:

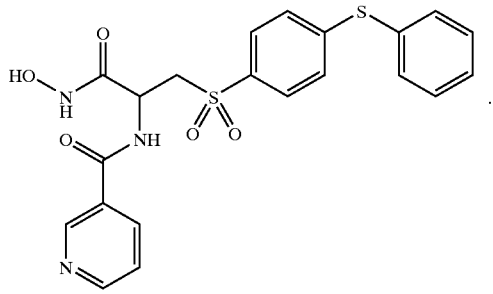

44. A compound or pharmaceutically acceptable salt thereof, wherein said compound corresponds in structure to the formula below:

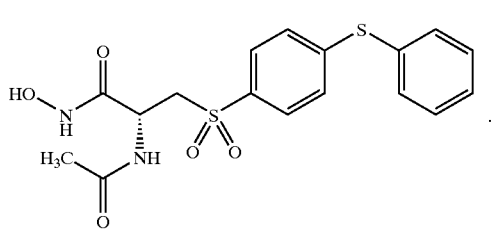

45. A compound or pharmaceutically acceptable salt thereof, wherein said compound corresponds in structure to the formula below:

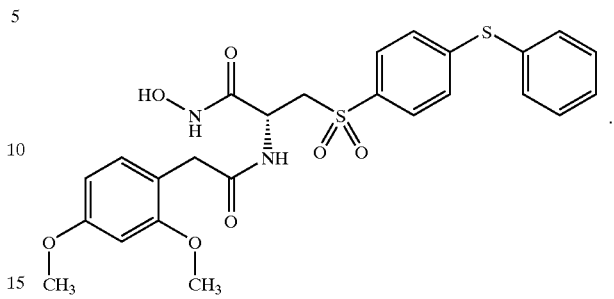

46. A compound or pharmaceutically acceptable salt thereof, wherein said compound corresponds in structure to the formula below:

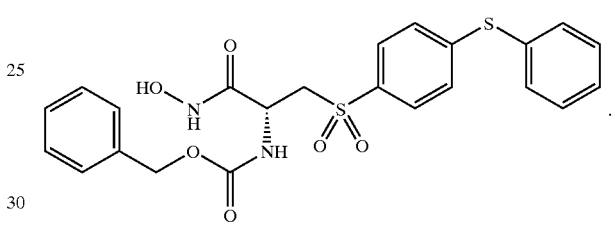

47. A compound or pharmaceutically acceptable salt thereof, wherein said compound corresponds in structure to the formula below:

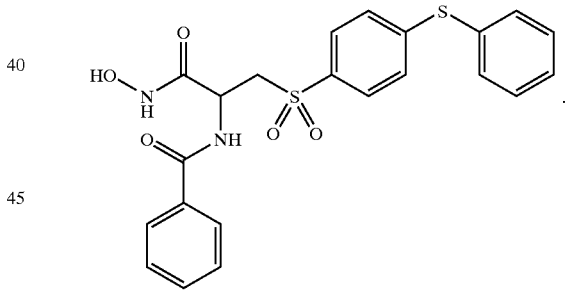

48. A compound or pharmaceutically acceptable salt thereof, wherein said compound corresponds in structure to the formula below:

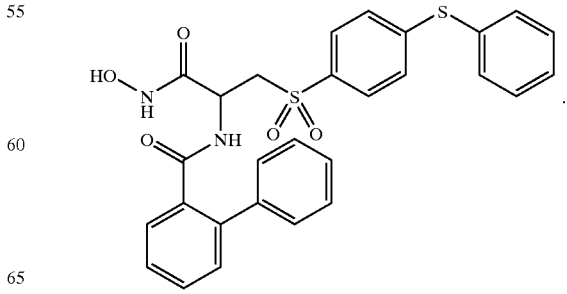

49. A compound or pharmaceutically acceptable salt thereof, wherein said compound corresponds in structure to the formula below:

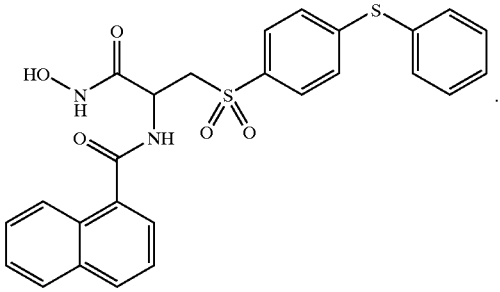

50. A compound or pharmaceutically acceptable salt thereof, wherein said compound corresponds in structure to the formula below:

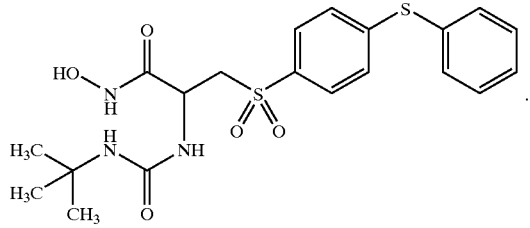

51. A compound or pharmaceutically acceptable salt thereof, wherein said compound corresponds in structure to the formula below:

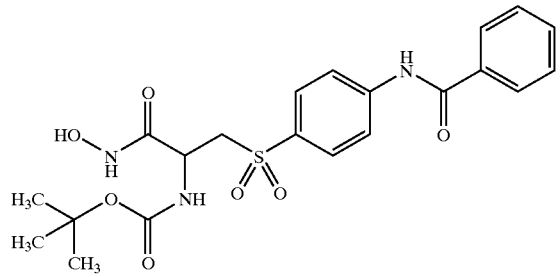

52. A compound or pharmaceutically acceptable salt thereof, wherein said compound corresponds in structure to the formula below:

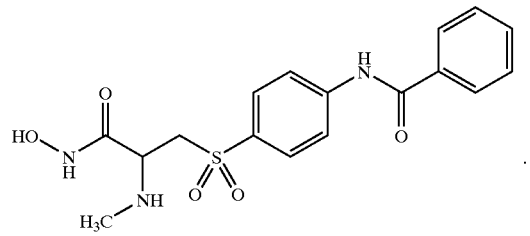

53. A compound or pharmaceutically acceptable salt thereof, the compound corresponding in structure to a formula selected from the group consisting of:

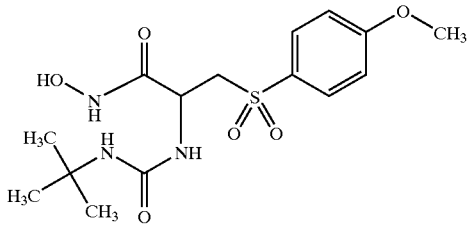

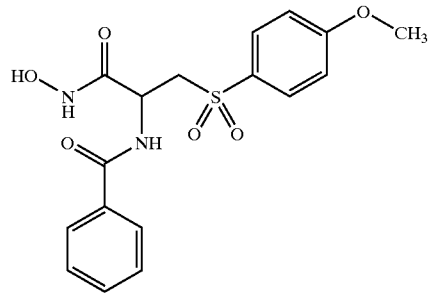

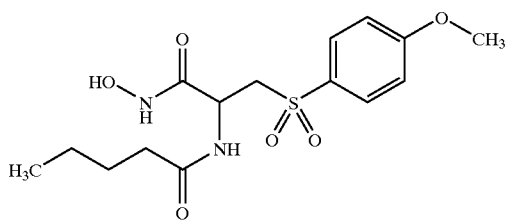

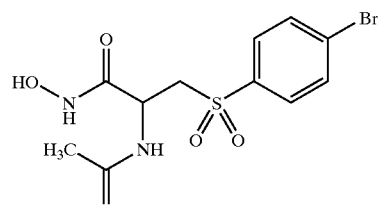

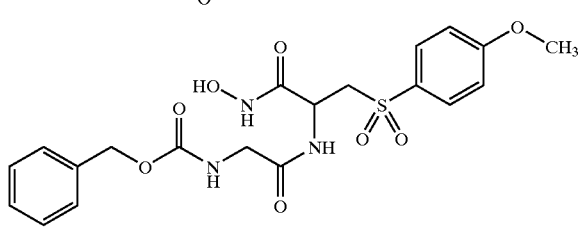

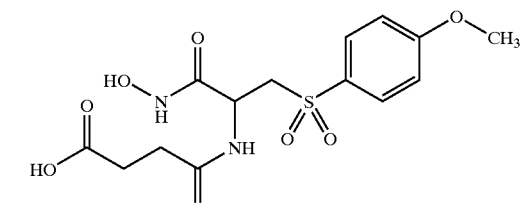

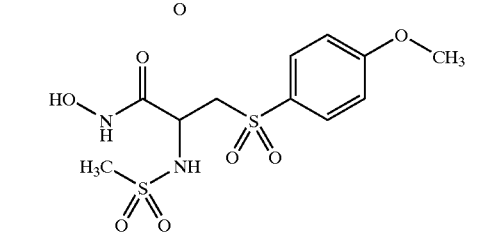

-continued
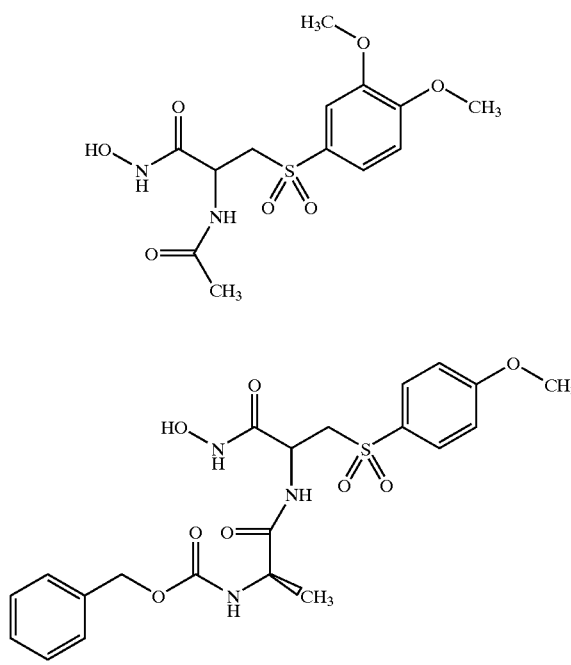
54. A compound corresponding in structure to a formula selected from the group consisting of:
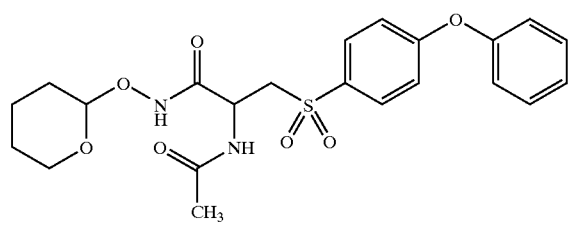
-continued
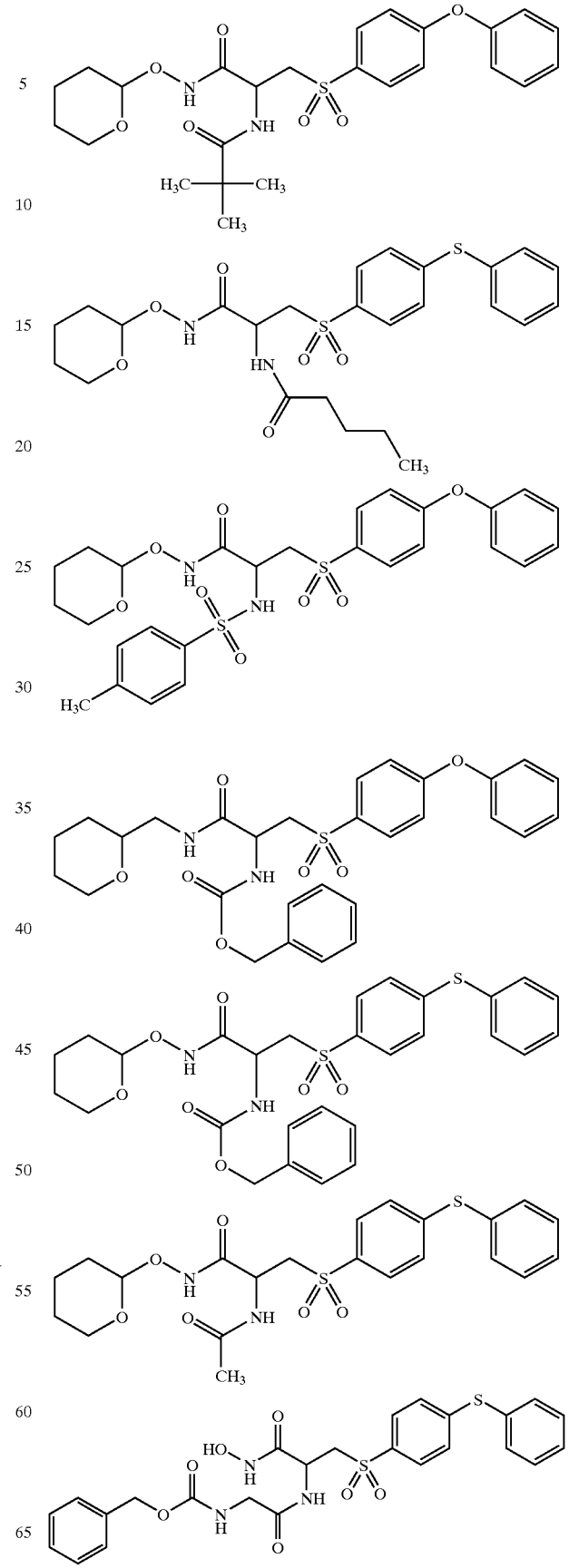

-continued

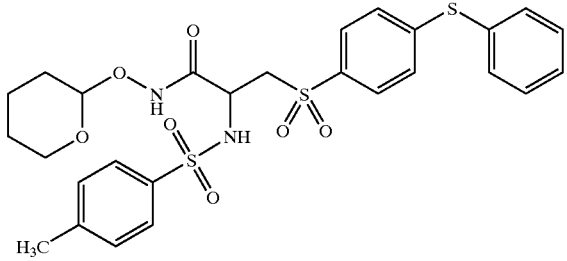

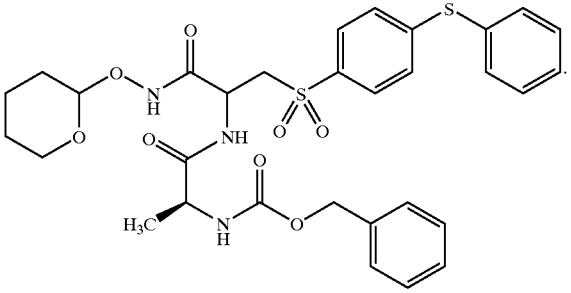

55. The compound or salt according to claim 53 wherein said compound corresponds in structure to the formula below

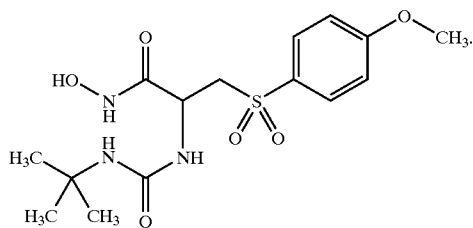

56. The compound or salt according to claim 53 wherein said compound corresponds in structure to the formula below

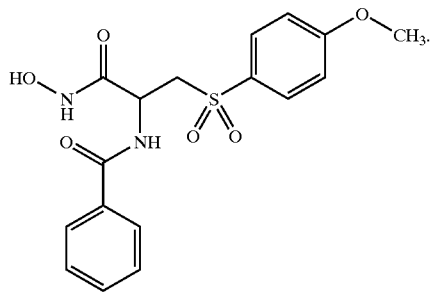

57. The compound or salt according to claim 53 wherein said compound corresponds in structure to the formula below

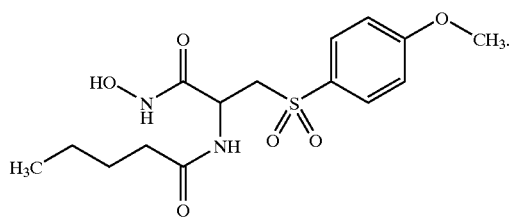

58. The compound or salt according to claim 53 wherein said compound corresponds in structure to the formula below

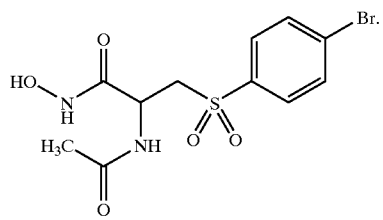

59. The compound or salt according to claim 53 wherein said compound corresponds in structure to the formula below

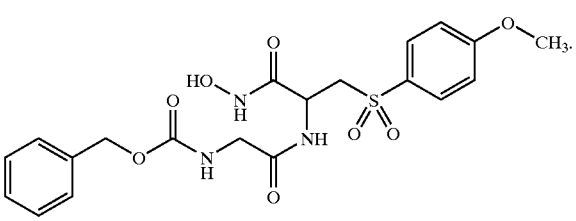

60. The compound or salt according to claim 53 wherein said compound corresponds in structure to the formula below

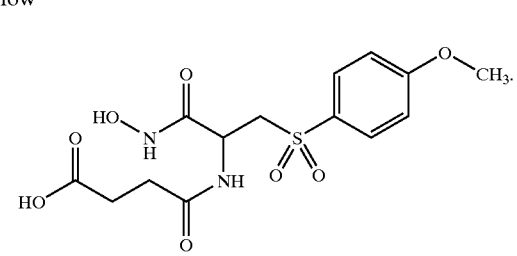

61. The compound or salt according to claim 53 wherein said compound corresponds in structure to the formula below

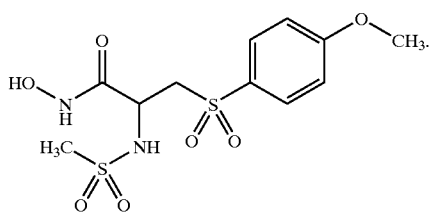

62. The compound or salt according to claim 53 wherein said compound corresponds in structure to the formula below

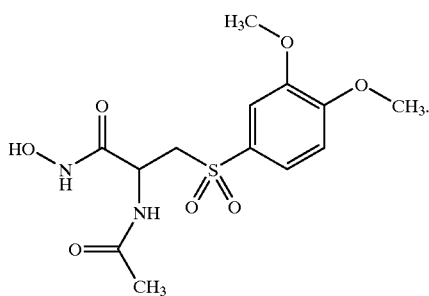

63. The compound or salt according to claim 53 wherein said compound corresponds in structure to the formula below

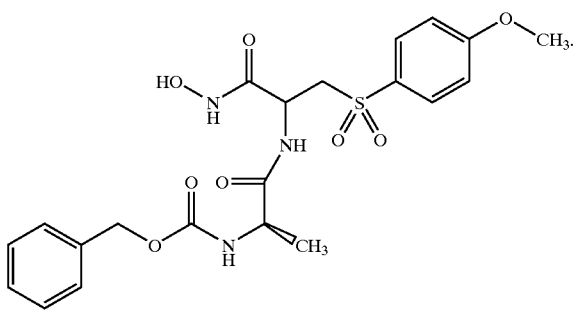

64. The compound or salt according to claim 53 wherein said compound corresponds in structure to the formula below

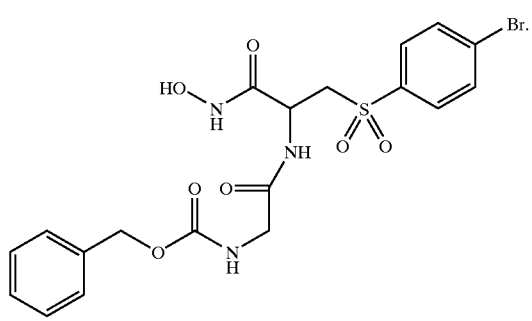

65. The compound or salt according to claim 53 wherein said compound corresponds in structure to the formula below

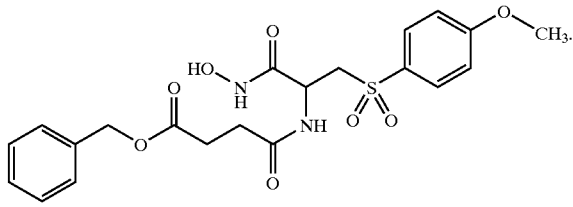

66. The compound according to claim 54 wherein said compound corresponds in structure to the formula below

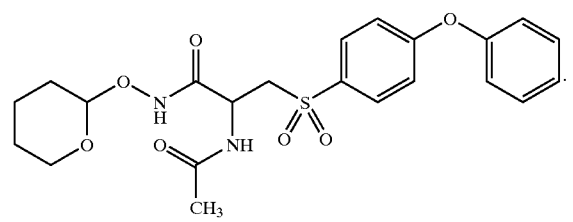

67. The compound according to claim 54 wherein said compound corresponds in structure to the formula below

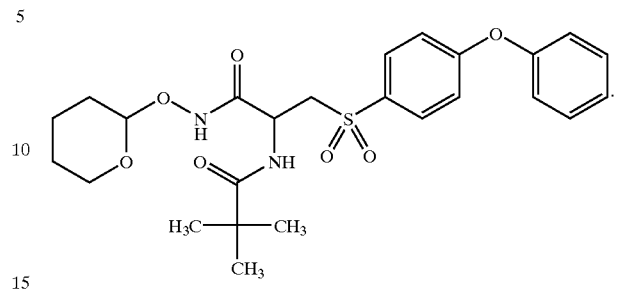

68. The compound according to claim 54 wherein said compound corresponds in structure to the formula below

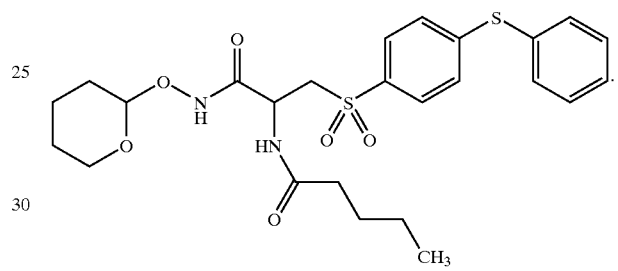

69. The compound according to claim 54 wherein said compound corresponds in structure to the formula below

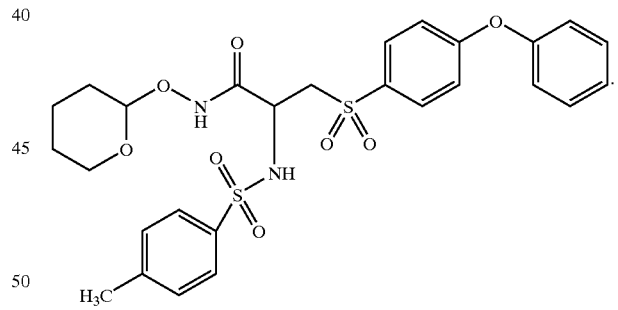

70. The compound according to claim 54 wherein said compound corresponds in structure to the formula below

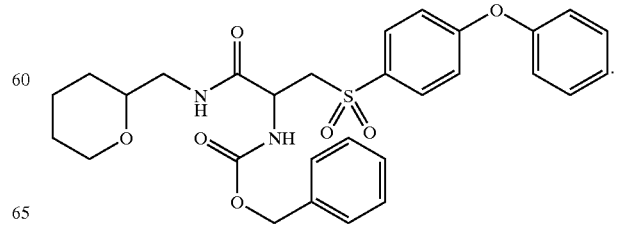

71. The compound according to claim 54 wherein said compound corresponds in structure to the formula below

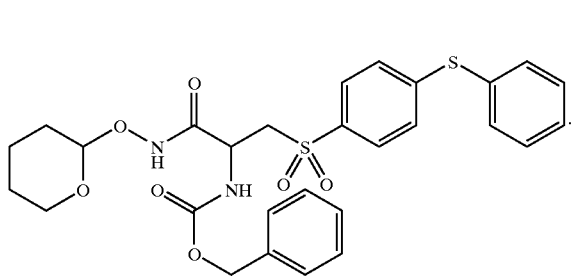

72. The compound according to claim 54 wherein said compound corresponds in structure to the formula below

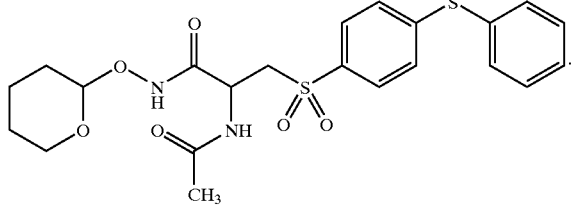

73. The compound according to claim 54 wherein said compound corresponds in structure to the formula below

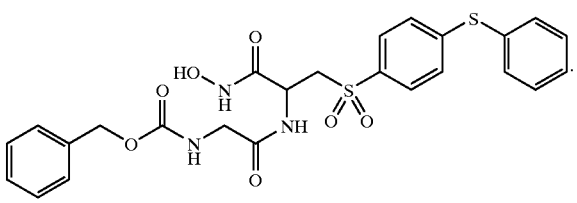

74. The compound according to claim 54 wherein said compound corresponds in structure to the formula below

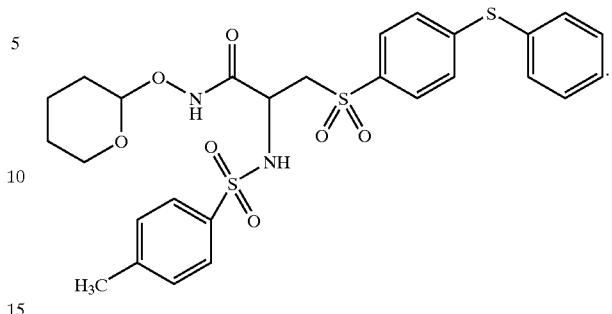

75. The compound according to claim 54 wherein said compound corresponds in structure to the formula below

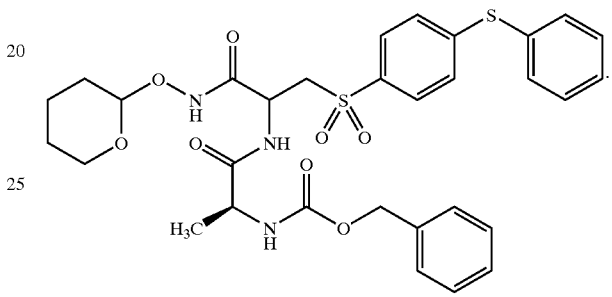

76. A compound or a pharmaceutically acceptable salt thereof, wherein the compound corresponds in structure to the formula below:

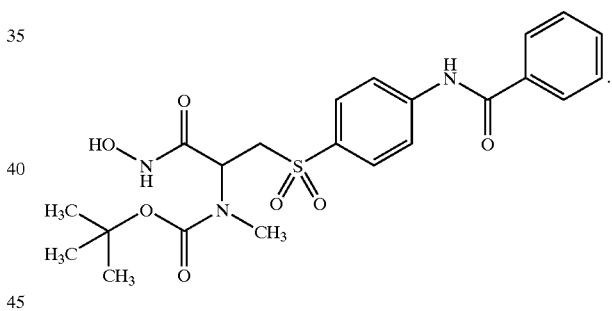

* * * * *

UNITED STATES PATENT AND TRADEMARK OFFICE
CERTIFICATE OF CORRECTION

PATENT NO. : 6,583,299 B1
DATED : June 24, 2003
INVENTOR(S) : Susan L. Hockerman et al.

It is certified that error appears in the above-identified patent and that said Letters Patent is hereby corrected as shown below:

Column 83,
Line 25, replace

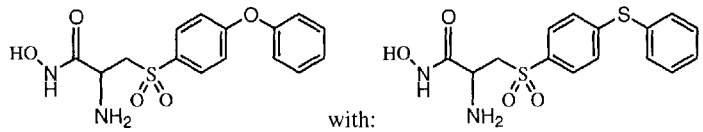

with:

Line 43, replace

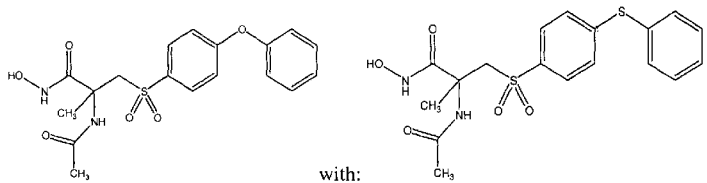

with:

Column 88,
Line 65, replace

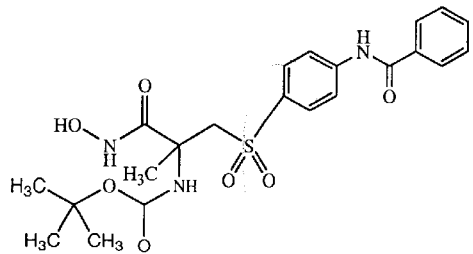

with:

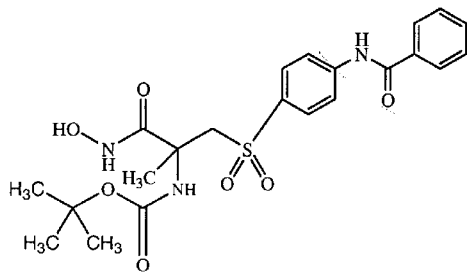

UNITED STATES PATENT AND TRADEMARK OFFICE
CERTIFICATE OF CORRECTION

PATENT NO. : 6,583,299 B1
DATED : June 24, 2003
INVENTOR(S) : Susan L. Hockerman et al.

It is certified that error appears in the above-identified patent and that said Letters Patent is hereby corrected as shown below:

Column 89,
Line 20, replace

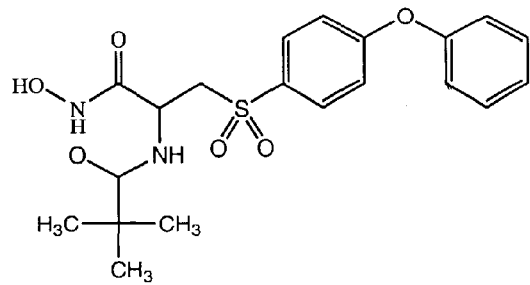

with:

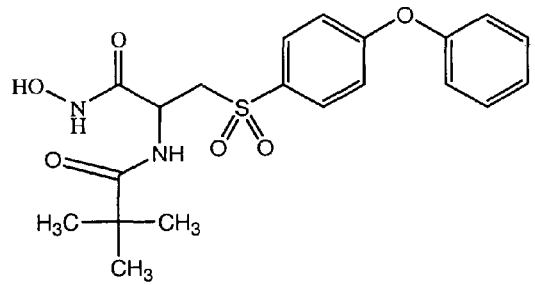

UNITED STATES PATENT AND TRADEMARK OFFICE
CERTIFICATE OF CORRECTION

PATENT NO. : 6,583,299 B1
DATED : June 24, 2003
INVENTOR(S) : Susan L. Hockerman et al.

It is certified that error appears in the above-identified patent and that said Letters Patent is hereby corrected as shown below:

Column 96,
Line 10, replace

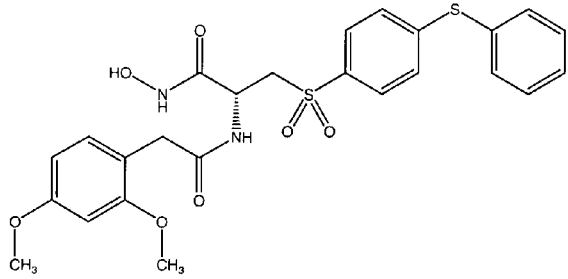

with:

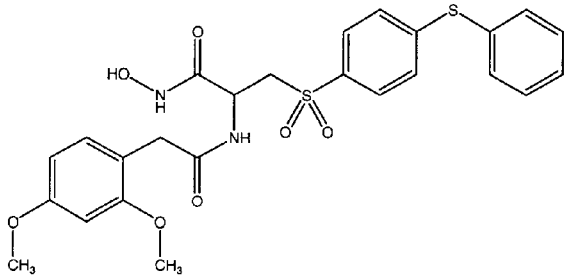

Signed and Sealed this

Twenty-seventh Day of January, 2004

JON W. DUDAS
*Acting Director of the United States Patent and Trademark Office*